US012807686B2

(12) United States Patent
Achkar et al.

(10) Patent No.: US 12,807,686 B2
(45) Date of Patent: Nov. 24, 2026

(54) **HIGH-AFFINITY *Mycobacterium tuberculosis* CAPSULE-SPECIFIC HUMAN MONOCLONAL ANTIBODY**

(71) Applicant: Albert Einstein College of Medicine, Bronx, NY (US)

(72) Inventors: Jacqueline M. Achkar, Brooklyn, NY (US); Elise Ishida, Aiea, HI (US); Yanyan Liu, Bronx, NY (US); Tingting Chen, Bronx, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 742 days.

(21) Appl. No.: 18/256,556

(22) PCT Filed: Dec. 15, 2021

(86) PCT No.: PCT/US2021/063461

§ 371 (c)(1),
(2) Date: Jun. 8, 2023

(87) PCT Pub. No.: WO2022/132868

PCT Pub. Date: Jun. 23, 2022

(65) Prior Publication Data

US 2024/0101650 A1 Mar. 28, 2024

Related U.S. Application Data

(60) Provisional application No. 63/199,235, filed on Dec. 15, 2020.

(51) Int. Cl.

| | |
|---|---|
| ***C07K 16/1289*** | (2026.01) |
| ***A61P 31/06*** | (2006.01) |
| ***G01N 33/543*** | (2006.01) |
| ***G01N 33/569*** | (2006.01) |

(52) U.S. Cl.

CPC .......... *C07K 16/1289* (2013.01); *A61P 31/06* (2018.01); *G01N 33/54386* (2013.01); *G01N 33/5695* (2013.01); *C07K 2317/21* (2013.01); *C07K 2317/77* (2013.01); *C07K 2317/92* (2013.01); *G01N 2333/35* (2013.01)

(58) Field of Classification Search

CPC .................................................. C07K 16/1289
USPC ...................................................... 424/137.1
See application file for complete search history.

(56) References Cited

U.S. PATENT DOCUMENTS

| | | | |
|---|---|---|---|
| 5,739,277 | A | 4/1998 | Presta et al. |
| 5,939,598 | A | 8/1999 | Kucherlapati et al. |
| 6,075,181 | A | 6/2000 | Kucherlapati et al. |
| 6,114,598 | A | 9/2000 | Kucherlapati et al. |
| 6,150,584 | A | 11/2000 | Kucherlapati et al. |
| 6,162,963 | A | 12/2000 | Kucherlapati et al. |
| 6,194,222 | B1 | 2/2001 | Buechler |
| 2016/0083458 | A1 | 3/2016 | Katsuragi et al. |

FOREIGN PATENT DOCUMENTS

| | | | |
|---|---|---|---|
| WO | 00/42072 | A2 | 7/2000 |
| WO | 02/43478 | A2 | 6/2002 |
| WO | 02/060919 | A2 | 8/2002 |
| WO | 2017139153 | A1 | 8/2017 |
| WO | 201900255 | A1 | 1/2019 |
| WO | 2020089380 | A1 | 5/2020 |
| WO | 2020160560 | A2 | 8/2020 |

OTHER PUBLICATIONS

Chen et al (JCI, 2020, 130(4): 1808-1822).*
Zheng, R. et al., Insights into Interactions of Mycobacteria with the Host Innate Immune System from a Novel Array of Synthetic Mycobacterial Glycans, ACS Chem. Biol. 2017, 12, 2990-3002.
International Search Report and Written Opinion for PCT/US21/63461 dated Apr. 18, 2022, 19 pages.
Kabat et al., Sequences of Proteins of Immunological Interest, 5th Ed. Public Health Service, National Institutes of Health, Bethesda, Md. (1987, 1991)) (abstract).
Chothia & Lesk 196 J. Mo!. Biol. 901 (1987))(abstract).
Lefranc, M.-P. et al., Dev. Comp. Immunol., 27, 55-77 (2003).
Devereux et al., Nucleic Acids Research 12: 387, 1984.
Altschul et al., J. Mo!. Biol. 215:403 (1990)(abstract).
BLAST Manual, Altschul, et al., NCBI NLM NIH, Bethesda, Md. 20894; BLAST 2.0 at http://www.ncbi.nlm.nih.gov/blast/.
Hoogenboom and Winter, J. Mol. Biol., 227:381 (1991); Marks et al., J. Mol. Biol., 222:581 (1991)(abstract).
Cole et al., Monoclonal Antibodies and Cancer Therapy, Alan R. Liss, p. 77 (1985).
Boemer et al., J. Immunol., 147(1 ):86-95 (1991)(abstract).
Van Dijk and van de Winkel, Curr. Opin. Pharmacol., 5: 368-74 (2001)(abstract).
Li et al., Proc. Natl. Acad. Sci. USA, I 03:3557-3562 (2006).
Tomizuka et al. (2000) Proc. Natl. Acad. Sci. USA 97:722-727.
Abbas AK, Lichtman AH, Pober JS. Cellular and Molecular Immunology, 4th edition, W.B. Saunders Co., Philadelphia, 2000 (abstract).
Wang et al. Protein Cell (2018), 9(1):63-73.
Karlsson, R. Roos, H. Fagerstam, L. Petersson, B. (1994). Methods Enzymology 6. 99-110 (abstract).
Ghetie et al., 18 Ann. Rev. Immunol. 739 (2000) (abstract).
Shields et al., 276 J. Biol. Chem. 6591 (2001).
Hinton, 279 J. Biol. Chem. 6213-6216 (2004).
Scopes, Protein Purification (Springer-Verlag, N.Y., (1982)(table of contents).

(Continued)

*Primary Examiner* — Sean E Aeder
(74) *Attorney, Agent, or Firm* — Fox Rothschild LLP

(57) ABSTRACT

Provided are high affinity *Mycobacterium tuberculosis* arabinomannan-specific antibodies and antigen-binding fragments thereof. Also provided are methods of use and devices employing such *Mycobacterium tuberculosis* arabinomannan-specific antibodies and antigen-binding fragments thereof.

19 Claims, 15 Drawing Sheets

Specification includes a Sequence Listing.

(56) References Cited

OTHER PUBLICATIONS

Choudhary et al., "Characterization of the Antigenic Heterogeneity of Lipoarabinomannan, the Major Surface Glycolipid of *Mycobacterium tuberculosis* and Complexity of Antibody Specificities Toward This Antigen," J Immunol (Apr. 2, 2018), 200(9): 3053-66.
Sigal, et al., "A Novel Sensitive Immunoassay Targeting the 5-Methylthio-d-Xylofuranose-Lipoarabinomannan Epitope Meets the WHO's Performance Target for Tuberculosis Diagnosis," J. Clin. Microbiol. (Sep. 26, 2018), 56(12):e01338-18 (17 pp).
Ishida et al., "Monoclonal antibodies from humans with *Mycobacterium tuberculosis* exposure or latent infection recognize distintinct arabinomannan epitopes," Commun. Biol. (Oct. 12, 2021), 4(1): 13 pp.
Moser et al., Clinical applications of capillary electrophoresis based immunoassays, 2014, Electrophoresis, vol. 35, p. 937-955.
Singhal et al. "Microfluidic Measurement of Antibody-Antigen Binding Kinetics from Low-Abundance Samples and Single Cells", Oct. 15, 2010, Analytical Chemistry, vol. 82, No. 20, p. 8671-8679.

* cited by examiner

B.

HIGH-AFFINITY *Mycobacterium tuberculosis* CAPSULE-SPECIFIC HUMAN MONOCLONAL ANTIBODY

STATEMENT OF GOVERNMENT SUPPORT

This invention was made with government support under grant number 1 R01 AI146329 awarded by National Institutes of Health/National Institute of Allergy and Infectious Diseases. The government has certain rights in the invention.

FIELD

This disclosure relates generally to antibodies against *Mycobacterium tuberculosis* surface polysaccharide arabinomannan (AM) and methods of use thereof.

BACKGROUND

With over 10 million cases per year and one million associated deaths, active tuberculosis (TB), caused by the facultative intracellular *Mycobacterium tuberculosis* (Mtb), is, after COVID-19, the leading cause of death from a single infectious agent. While an estimated quarter of the world is latently infected with Mtb, TB is caused by uncontrolled infection leading to a predominantly respiratory and transmissible disease.

The capsule of microorganisms, including Mtb, is an important virulence factor. Antibodies (Abs) to capsular and surface polysaccharides are protective against infections with encapsulated extra- and intracellular pathogens. Some successful vaccines are based on inducing Abs to capsular polysaccharides. The mechanisms by which Abs protect against *Mycobacterium tuberculosis* (Mtb) have been insufficiently studied because of the general belief that Mtb, a predominantly intracellular organism, is outside the reach of extracellular located Abs. However, Abs contribute to the defense against many intracellular pathogens, including Mtb, through various functions, including interactions with Fc receptors (FcR) and the modulation of innate and other immune responses.

The majority of the mycobacterial capsule is composed of polysaccharides and proteins; lipids are a minor component of the capsule. The three major capsular polysaccharides are α-glucan, arabinomannan (AM), and mannan. The 13-20 kDa, immunogenic polysaccharide AM can be isolated from the capsule of Mtb.

The cell walls and membranes of mycobacteria comprise lipoarabinomannan (LAM), a glycolipid that comprises AM. Both AM and LAM are very immunogenic. Some but not all murine monoclonal antibodies (mAbs) to AM/LAM show protective in vivo efficacy, and immunization with AM/LAM-protein conjugates improves the outcome of Mtb infected mice. However, these studies are limited in capturing the tremendous complexity and heterogeneity of potentially Mtb protective antibodies in humans. Nevertheless, they are consistent with the data that not all 'anti-AM' mAbs have the same binding specificity or protective ability. Several recent studies provide compelling data suggesting that Mtb specific antibodies have a role in controlling Mtb infection in humans and could be protective but very little is known about the functions of antigen-specific human mAbs in Mtb infection.

Accordingly, to combat the major global public health problem caused by TB, ongoing development of additional tools for both research and clinical care is critical to meet the continuing urgent need for the rapid detection, treatment, and prevention of Mtb infection. Beyond their potential to inform vaccine and immunotherapy development, antibodies are versatile and indispensable tools in a plethora of applications in medicine and research, including the detection of pathogens and their antigens.

Additionally, there is an urgent need for a simple, yet highly sensitive non-sputum-based point-of-care (POC) test. To have an impact on global TB control, a non-sputum-based POC needs to be all—accurate, robust, and suitable for the use of community health care providers in resource-limited settings. The most promising approach to achieve these criteria is the detection of the *M. tuberculosis* (Mtb) surface glycolipid lipoarabinomannan (LAM) in urine via a lateral flow format. The AlereLAM dipstick test, however, has a sensitivity <50% in HIV-associated TB (<20% in non-HIV TB) with an inverse correlation between sensitivity and CD4 cells, and relies on polyclonal rabbit sera for LAM capture and detection. The recently developed next generation FujiLAM test uses two new anti-LAM monoclonal antibodies (mAbs) and has higher sensitivity. However, it is less simple, requires an extra silver amplification step, and its sensitivity for TB is <50% in PLHIV with >200 CD4 cells (~50% in non-HIV TB). Therefore, additional tools such as high-affinity mAbs that bind to AM/LAM for simple POC diagnosis TB are urgently needed.

BRIEF SUMMARY

In one aspect, provided is an anti-*Mycobacterium tuberculosis* arabinomannan (anti-Mtb AM) antibody, or *Mycobacterium tuberculosis* arabinomannan-binding fragment (Mtb AM-binding fragment) thereof, wherein the anti-Mtb AM antibody, or Mtb AM-binding fragment thereof, comprises a heavy chain variable region and a light chain variable region, wherein each of the heavy chain and the light chain variable regions comprises a CDR1, CDR2, and CDR3; and wherein CDR1H comprises SEQ ID NO:1, CDR2H comprises SEQ ID NO:2, CDR3H comprises SEQ ID NO: 4, CDR1L comprises SEQ ID NO:3, CDR2L comprises SEQ ID NO: 5, and CDR3L comprises SEQ ID NO:6.

In one aspect, provided is anti-Mtb AM antibody, or Mtb AM-binding fragment thereof, wherein the anti-Mtb AM antibody, or Mtb AM-binding fragment thereof, comprises a heavy chain variable region and a light chain variable region, wherein each of the heavy chain and the light chain variable regions comprises a CDR1, CDR2, and CDR3; and wherein CDR1H comprises SEQ ID NO:26, CDR2H comprises SEQ ID NO:27, CDR3H comprises SEQ ID NO:28, CDR1L comprises SEQ ID NO:29, CDR2L comprises SEQ ID NO:30, and CDR3L comprises SEQ ID NO:31.

In one embodiment, the anti-Mtb AM antibody, or Mtb AM-binding fragment thereof, comprises a heavy chain variable region that is at least 80% identical to SEQ ID NO:7 and a light chain variable region that is at least 80% identical to SEQ ID NO:8.

In one embodiment, the anti-Mtb AM antibody, or Mtb AM-binding fragment thereof, comprises a heavy chain variable region that is at least 80% identical to SEQ ID NO:32 and a light chain variable region that is at least 80%, identical to SEQ ID NO:34.

In one embodiment, the anti-Mtb AM antibody, or Mtb AM-binding fragment thereof, comprises a heavy chain variable region that comprises SEQ ID NO:7 and a light chain variable region that comprises SEQ ID NO:8.

In one embodiment, the anti-Mtb AM antibody, or Mtb AM-binding fragment thereof, comprises a heavy chain variable region that comprises SEQ ID NO:32 and a light chain variable region that comprises SEQ ID NO:34.

In one embodiment, the anti-Mtb AM antibody, or Mtb AM-binding fragment thereof, is a monoclonal antibody.

In one embodiment, the anti-Mtb AM antibody, or Mtb AM-binding fragment thereof, comprises (i) a VH framework comprising the framework sequence of human germline VH 3-23*01; and/or (ii) a VK framework comprising the framework sequence of human germline 2-24*01.

In one embodiment, the anti-Mtb AM antibody, or Mtb AM-binding fragment thereof, comprises (i) a VH framework comprising the framework sequence of human germline VH 4-59*08; and/or (ii) a VL framework comprising the framework sequence of human germline VL 1-51*02.

In one embodiment, the anti-Mtb AM antibody, or Mtb AM-binding fragment thereof, is a recombinant antibody.

In one embodiment, the anti-Mtb AM antibody, or Mtb AM-binding fragment thereof, comprises a human framework region or a modified human framework region.

In one embodiment, the anti-Mtb AM antibody, or Mtb AM-binding fragment thereof, comprises a human constant region or a modified human constant region.

In one embodiment, the Mtb AM-binding fragment is an scFv, Fv, Fab', Fab, $F(ab')_2$, or diabody.

In one embodiment, the anti-Mtb AM antibody, or Mtb AM-binding fragment thereof, is deglycosylated.

In one embodiment, the anti-Mtb AM antibody, or Mtb AM-binding fragment thereof, is conjugated to one or more of a cytotoxin, a fluorescent label, and an imaging agent.

Provided herein is a nucleic acid molecule encoding an anti-Mtb AM antibody, or Mtb AM-binding fragment thereof, disclosed herein. In one embodiment, nucleic acid molecule is an isolated nucleic acid molecule.

In one embodiment, the nucleic acid molecule comprises SEQ ID NO:9 and/or SEQ ID NO: 10. In one embodiment, the nucleic acid molecule comprises SEQ ID NO:33 and/or SEQ ID NO:35.

Provided herein is a vector or set of vectors comprising one or more nucleic acid molecules disclosed herein. Provided herein is a vector or set of vectors comprising a nucleic acid molecule encoding an anti-Mtb AM antibody, or Mtb AM-binding fragment thereof, disclosed herein.

Provided herein is a host cell comprising a nucleic acid molecule or a vector disclosed herein. Provided herein is a host cell comprising a nucleic acid molecule encoding an anti-Mtb AM antibody, or Mtb AM-binding fragment thereof, disclosed herein. Provided herein is a host cell comprising vector comprising a nucleic acid molecule encoding an anti-Mtb AM antibody, or Mtb AM-binding fragment thereof, disclosed herein. The cell may be isolated.

In one aspect, provided is a method of producing an anti-Mtb AM antibody, or Mtb AM-binding fragment thereof, comprising culturing a host cell comprising vector comprising a nucleic acid molecule encoding an anti-Mtb AM antibody, or Mtb AM-binding fragment thereof, disclosed herein, under conditions wherein the anti-Mtb AM antibody, or Mtb AM-binding fragment thereof, is produced by the host cell.

In one embodiment, provided is a pharmaceutical composition comprising an anti-Mtb AM antibody, or Mtb AM-binding fragment thereof, disclosed herein, and a pharmaceutically acceptable excipient.

In one aspect, provided is a method of reducing an activity of *Mycobacterium tuberculosis* AM in a subject in need thereof, the method comprising administering to said subject a therapeutically effective amount of an anti-Mtb AM antibody, or Mtb AM-binding fragment thereof, disclosed herein.

In one aspect, provided is a method of reducing an activity of *Mycobacterium tuberculosis* AM in a subject in need thereof, the method comprising administering to said subject a therapeutically effective amount of a pharmaceutical composition, wherein the pharmaceutical composition comprises an anti-Mtb AM antibody, or Mtb AM-binding fragment thereof, disclosed herein, and a pharmaceutically acceptable excipient.

In one aspect, provided is a method of treating a *Mycobacterium tuberculosis* infection in a subject, the method comprising administering to the subject an amount of an anti-Mtb AM antibody, or Mtb AM-binding fragment thereof, disclosed herein, wherein the amount is effective to treat a *Mycobacterium tuberculosis* infection.

In one aspect, provided is a method of treating a *Mycobacterium tuberculosis* infection in a subject, the method comprising administering to the subject an amount of a pharmaceutical composition, wherein the amount is effective to treat a *Mycobacterium tuberculosis* infection, and wherein the pharmaceutical composition comprises an anti-Mtb AM antibody, or Mtb AM-binding fragment thereof, disclosed herein, and a pharmaceutically acceptable excipient.

In one aspect, provided is a method of reducing the likelihood of a *Mycobacterium tuberculosis* infection in a subject, the method comprising administering to the subject who does not have a *Mycobacterium tuberculosis* infection an amount of an anti-Mtb AM antibody, or Mtb AM-binding fragment thereof, disclosed herein, wherein the amount is effective to reduce the likelihood of a *Mycobacterium tuberculosis* infection.

In one aspect, provided is a method of reducing the likelihood of a *Mycobacterium tuberculosis* infection in a subject, the method comprising administering to the subject who does not have a *Mycobacterium tuberculosis* infection an amount of a pharmaceutical composition, wherein the pharmaceutical composition comprises an anti-Mtb AM antibody, or Mtb AM-binding fragment thereof, disclosed herein, and a pharmaceutically acceptable excipient, and wherein the amount is effective to reduce the likelihood of a *Mycobacterium tuberculosis* infection.

In one aspect, provided is a method of treating a disease, disorder, or condition mediated by, or related to increased activity of *Mycobacterium tuberculosis* in a subject, the method comprising administering to said subject a therapeutically effective amount of an anti-Mtb AM antibody, or Mtb AM-binding fragment thereof, disclosed herein.

In one aspect, provided is a method of treating a disease, disorder, or condition mediated by, or related to increased activity of *Mycobacterium tuberculosis* in a subject, the method comprising administering to said subject a therapeutically effective amount of a pharmaceutical composition, wherein the pharmaceutical composition comprises an anti-Mtb AM antibody, or Mtb AM-binding fragment thereof, disclosed herein, and a pharmaceutically acceptable excipient.

An assay device is provided for selectively detecting one or more bacteria from the *Mycobacterium tuberculosis* complex (MTC) group in a biological sample comprising: a first portion comprising a first plurality of anti-Mtb AM-antibodies, or Mtb AM-binding fragments thereof, as described herein, or anti-mycobacterial AM-antibodies, wherein the antibodies or fragments are each attached to their own reporting entity; and a second portion comprising a second plurality of anti-Mtb AM-antibodies, or Mtb AM-binding fragments thereof, or anti-mycobacterial AM-antibodies.

In some embodiments, the second plurality of anti-*Mycobacterium tuberculosis* antibodies, comprises antibodies comprising a heavy chain variable region and a light chain variable region, wherein the heavy chain and the light chain variable regions comprises a CDR1, CDR2, and CDR3; and wherein CDR1H comprises SEQ ID NO:17, CDR2H comprises SEQ ID NO:18, CDR3H comprises SEQ ID NO:19, CDR1L comprises SEQ ID NO:20, CDR2L comprises SEQ ID NO:21, and CDR3L comprises SEQ ID NO:22.

Provided herein is an assay device for selectively detecting one or more bacteria from the *Mycobacterium tuberculosis* complex (MTC) group in a biological sample comprising:

(a) a first portion comprising a first plurality of anti-Mtb AM antibodies, or Mtb AM-binding fragments thereof, wherein the anti-Mtb AM antibodies, or Mtb AM-binding fragments thereof, are attached to a reporting entity and wherein anti-Mtb AM antibodies, or Mtb AM-binding fragments thereof, comprise a heavy chain variable region and a light chain variable region, wherein the heavy chain and the light chain variable regions comprises a CDR1, CDR2, and CDR3; and wherein:
   a. CDR1H comprises SEQ ID NO:17, CDR2H comprises SEQ ID NO:18, CDR3H comprises SEQ ID NO:19, CDR1L comprises SEQ ID NO:20, CDR2L comprises SEQ ID NO:21, and CDR3L comprises SEQ ID NO:22,
   b. CDR1H comprises SEQ ID NO:1, CDR2H comprises SEQ ID NO:2, CDR3H comprises SEQ ID NO:3, CDR1L comprises SEQ ID NO:4, CDR2L comprises SEQ ID NO:5, and CDR3L comprises SEQ ID NO:6; or
   c. CDR1H comprises SEQ ID NO:26, CDR2H comprises SEQ ID NO:27, CDR3H comprises SEQ ID NO:28, CDR1L comprises SEQ ID NO:29, CDR2L comprises SEQ ID NO:30, and CDR3L comprises SEQ ID NO:31; and (b) a second portion comprising a second plurality of anti-Mtb AM antibodies, or Mtb AM-binding fragments thereof, disclosed herein.

Provided herein is an assay device for selectively detecting AM or LAM from the *Mycobacterium tuberculosis* complex (MTC) group in a biological sample comprising:

(a) a first portion comprising a first plurality of anti-Mtb AM antibodies, or Mtb AM-binding fragments thereof, wherein the anti-Mtb AM antibodies, or Mtb AM-binding fragments thereof, are attached to a reporting entity and wherein anti-Mtb AM antibodies, or Mtb AM-binding fragments thereof, comprise a heavy chain variable region and a light chain variable region, wherein the heavy chain and the light chain variable regions comprises a CDR1, CDR2, and CDR3; and wherein:
   a. CDR1H comprises SEQ ID NO:17, CDR2H comprises SEQ ID NO:18, CDR3H comprises SEQ ID NO:19, CDR1L comprises SEQ ID NO: 20, CDR2L comprises SEQ ID NO:21, and CDR3L comprises SEQ ID NO:22,
   b. CDR1H comprises SEQ ID NO:1, CDR2H comprises SEQ ID NO:2, CDR3H comprises SEQ ID NO:3, CDR1L comprises SEQ ID NO:4, CDR2L comprises SEQ ID NO:5, and CDR3L comprises SEQ ID NO:6; or
   c. CDR1H comprises SEQ ID NO:26, CDR2H comprises SEQ ID NO:27, CDR3H comprises SEQ ID NO:28, CDR1L comprises SEQ ID NO:29, CDR2L comprises SEQ ID NO:30, and CDR3L comprises SEQ ID NO:31; and (b) a second portion comprising a second plurality of anti-Mtb AM antibodies, or Mtb AM-binding fragments thereof, disclosed herein.

In one embodiment, the reporting entity comprises a gold nanoparticle. In one embodiment, the reporting entity comprises an enzyme. In some embodiments, the enzyme is horseradish peroxidase (HRP) or alkaline phosphatase (AP).

In some embodiments, the second plurality of anti-Mtb AM-antibodies, or Mtb AM-binding fragments thereof, or anti-mycobacterial AM-antibodies is affixed to a solid support of the device.

In some embodiments, the first plurality of second plurality of anti-Mtb AM-antibodies, or Mtb AM-binding fragments thereof, or anti-mycobacterial AM-antibodies is not affixed to a solid support of the device.

In some embodiments, the solid support comprises nitrocellulose.

In some embodiments, the assay device further comprises a fluid sample pad prior in sequential order to the first and second portions. In some embodiments, the assay device further comprises a control portion subsequent in sequential order to the first and second portions.

In some embodiments, the control portion comprises a third plurality of antibodies, immobilized on a solid support of the device, and which third plurality of antibodies are capable of binding the first plurality of anti-Mtb AM-antibodies, or Mtb AM-binding fragments thereof, or anti-mycobacterial AM-antibodies each attached to their own reporting molecule.

In some embodiments, assay device further comprises a fluid-absorbent wicking pad subsequent in sequential order to the first and second portions, and third portion if present.

In some embodiments, the assay device is a lateral flow assay device.

In one aspect, provided is a method of detecting one or more bacteria from the MTC group in a biological sample comprising: (a) contacting an assay device disclosed herein with the sample; and (b) observing if one or more bacteria from the MTC group bind to the second plurality of anti-Mtb AM antibodies, or Mtb AM-binding fragments thereof, or anti-mycobacterial AM-antibodies; wherein if one or more bacteria from the MTC group bind to the second plurality of anti-Mtb AM antibodies, or Mtb AM-binding fragments thereof, or anti-mycobacterial AM-antibodies, then one or more bacteria from the MTC group bind have been detected in the biological sample; and wherein if no bacteria from the MTC group bind to the second plurality of anti-Mtb AM antibodies, or Mtb AM-binding fragments thereof, or anti-mycobacterial AM-antibodies, then bacteria from the MTC group have not been detected in the biological sample. In some embodiments, the method further comprises obtaining the sample from a subject.

In some embodiments, the sample is urine, cerebrospinal fluid, pleural fluid, peritoneal fluid, sputum, saliva, a tissue sample, or a fine-needle aspirate.

In some embodiments, the subject is human.

BRIEF DESCRIPTION OF THE DRAWINGS

FIGS. 2A and 2B use the same labeling scheme. FIGS. 2C and 2D use the same labeling scheme.

FIG. 5A Detection of serial dilutions of LAM and AM generated from the clinical Mtb strain CDC1551 and spiked into urine by L1AM04 (10 μg/ml) as a capture and T1AM09 (250 ng/ml) as a detection mAb. FIG. 5B. Combination of murine mAb CS-35 (10 μg/ml) as a capture and human mAb A194 (250 ng/ml) as a reference.

FIG. 6C. Binding of positive (sera from T1 and L1) and negative (isotype matched mAb to a flavivirus) controls to H37Rv.

FIG. 7C shows staining for Acid-Fast Bacilli (AFB). FIG. 7D shows staining of intracellular LAM in Mtb (CDC1551) infected lungs (arrows indicate LAM within macrophages) by T1AM09. FIG. 7E shows staining of intracellular LAM and single bacilli in Mtb Erdman infected lungs (arrow indicates LAM within macrophages) by L1AM04. FIG. 7F shows lack of positive AFB staining of Mtb (Erdman) in approximately the same Mtb infected lung section as shown in the other figure panels. Overall lack of staining of non-infected murine tissue (scale bar 100 μm) by T1AM09 (FIG. 7G) and L1AM04 (FIG. 7H). FIG. 7I shows lack of staining of Mtb (CDC1551) infected lung tissue by isotype-matched control mAb to a flavivirus (scale bar 100 μm). All mAbs were tested at 2 μg/mL.

FIGS. 9A and 9B show enhanced *M. tuberculosis* phagocytosis by human monocyte cell lines (U937R3a: FIG. 9A; THP1 cells: FIG. 9B) in the presence of antibody P1AM25 and L1AM04. 5M16 is an irrelevant isotype matched human mAb, V10 and V29 are reference sera with low and moderate-high anti-AM IgG, respectively. PMA differentiated THP-1 cells seeded at $1\times10^5$ per well in a 96-well plate. The cells were infected with H37Ra-FITC at MOI of 20 in the presence of different AM mAbs at indicated concentrations for 3 hours.

FIG. 10A. Median Fluorescent Intensity (MFI) of binding to 63 mycobacterial oligosaccharide fragments is shown. Arabinomannan/lipoarabinomannan (AM/LAM) specific fragments (S #1-12, 15-22, 25, 44, 45, 49, 50, 56-59) are marked by the side bar. Six other glycans on the array are: α-glucan (S #13, 14, 24, 46, 48, 52), trehalose mycolates and lipooligosachharides (LOSs; S #38, 39, 54, 55), phenolic glycolipids (PGLs; S #26-37, 40-43, 50, 53), phosphatidyl-myo-inositol mannosides (PIMs, S #23) and glycopepitdolipids (GPLs; S #47, 60, 61). The glycan fingerprint of control antibody CS-35 is shown for comparison. FIG. 10B. Symbol representation of the mycobacterial glycans on the array. The degree of conjugation of each glycan to bovine serum albumin, in moles per mole, is indicated in parentheses below the glycan number.

DETAILED DESCRIPTION

Figure 1:
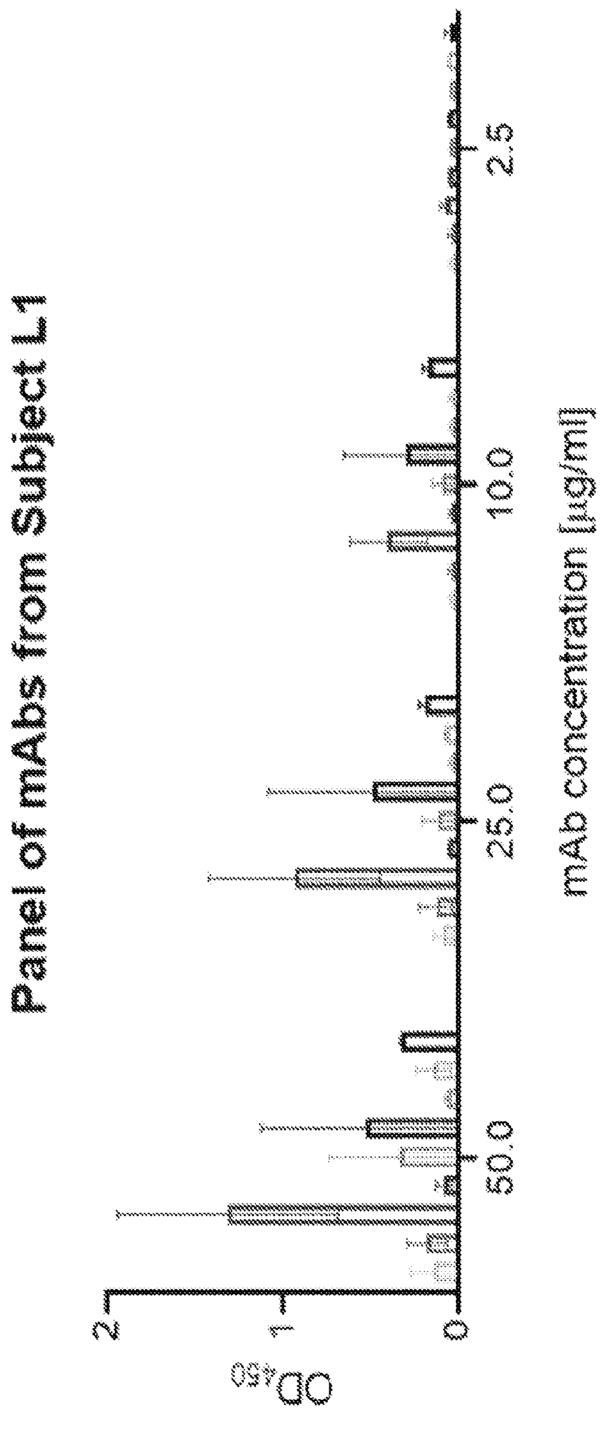
FIG. 1 shows that an asymptomatic donor produced antibodies with heterogeneous reactivities to arabinomannan (AM). Binding of mAbs generated from donor L1 to H37Rv AM as determined by ELISA. Bars from left to right: L1AM01, L1AM03, L1AM04, L1AM05, L1AM08, L1AM10, L1AM13, L1AM14, and L1AM16.

The disclosure provides antibodies and an antigen-binding fragments thereof that bind to *Mycobacterium tuberculosis* arabinomannan (AM) and the AM portion of lipoarabinomannan (LAM), as well as methods of using such antibodies and an antigen-binding fragments thereof. In embodiments, the antibodies or antigen-binding fragments thereof disclosed herein bind to bacteria from the *Mycobacterium tuberculosis* complex (MTC) group or AM/LAM from bacteria from MTC.

The term "antibody" is used in the broadest sense and includes monoclonal antibodies (including full length or intact monoclonal antibodies), polyclonal antibodies, multivalent antibodies, multispecific antibodies (e.g., bispecific antibodies).

As used herein, "antibody variable domain" refers to the portions of the light and heavy chains of antibody molecules that include amino acid sequences of complementarity determining regions (CDRs; i.e., CDR1, CDR2, and CDR3), and framework regions. $V_H$ refers to the variable domain of the heavy chain. $V_L$ refers to the variable domain of the light chain. The term "framework regions" refers to those variable domain residues other than the CDR residues. Further, the "light chains" of antibodies (immunoglobulins) from any vertebrate species can be assigned to one of two clearly distinct types, called kappa (κ) and lambda (λ), based on the amino acid sequences of their constant domains.

As used herein, the term "complementarity determining regions" refers to portions of an antibody variable domain that are (typically, but not always) involved in antigen binding. Each variable domain typically has three CDR regions identified as CDR1, CDR2 and CDR3. Each CDR can comprise amino acid residues from a CDR as defined by e.g. Kabat (Kabat et al., Sequences of Proteins of Immunological Interest, 5th Ed. Public Health Service, National Institutes of Health, Bethesda, Md. (1987, 1991)). Each CDR can also comprise amino acid residues from a "hypervariable loop" as defined by Chothia (Chothia & Lesk 196 J. Mol. Biol. 901 (1987)). In some instances, a CDR can include amino acids from both a CDR region defined according to Kabat and a hypervariable loop. The Kabat residue designations do not always correspond directly with the linear numbering of the amino acid residues (primary amino acid sequence). The actual linear amino acid sequence may contain fewer or additional amino acids than in the strict Kabat numbering corresponding to a shortening of, or insertion into, a structural component, whether framework or CDR, of the basic variable domain structure. The correct Kabat numbering of residues may be determined for a given antibody or antigen-binding fragment thereof by alignment of residues of homology in the sequence of the antibody or antigen-binding fragment thereof with a "standard" Kabat numbered sequence. Alternatively, a CDR may be defined according to the ImMunoGeneTics (IMGT) system (Lefranc, M.-P. et al., Dev. Comp. Immunol., 27, 55-77 (2003)).

Provided herein is an anti-*Mycobacterium tuberculosis* arabinomannan (anti-Mtb AM) antibody, or *Mycobacterium tuberculosis* arabinomannan-binding fragment (Mtb AM-binding fragment) thereof, wherein said antibody or fragment thereof comprises a heavy chain variable region and a light chain variable region, wherein each of the heavy chain and the light chain variable regions comprises a CDR1, CDR2, and CDR3; and wherein CDR1H comprises SEQ ID NO:1, CDR2H comprises SEQ ID NO:2, CDR3H comprises SEQ ID NO:3, CDR1L comprises SEQ ID NO:4, CDR2L comprises SEQ ID NO:5, and CDR3L comprises SEQ ID NO:6.

Provided herein is an anti-*Mycobacterium tuberculosis* arabinomannan (anti-Mtb AM) antibody, or *Mycobacterium tuberculosis* arabinomannan-binding fragment (Mtb AM-binding fragment) thereof, wherein said antibody or fragment thereof comprises a heavy chain variable region and a light chain variable region, wherein each of the heavy chain and the light chain variable regions comprises a CDR1, CDR2, and CDR3; and wherein CDR1H comprises SEQ ID NO:11, CDR2H comprises SEQ ID NO:12, CDR3H comprises SEQ ID NO: 13, CDR1L comprises SEQ ID NO:14, CDR2L comprises SEQ ID NO:15, and CDR3L comprises SEQ ID NO:16.

Provided herein is an anti-*Mycobacterium tuberculosis* arabinomannan (anti-Mtb AM) antibody, or *Mycobacterium tuberculosis* arabinomannan-binding fragment (Mtb AM-binding fragment) thereof, wherein said antibody or fragment thereof comprises a heavy chain variable region and a light chain variable region, wherein each of the heavy chain and the light chain variable regions comprises a CDR1, CDR2, and CDR3; and wherein CDR1H comprises SEQ ID NO:26, CDR2H comprises SEQ ID NO:27, CDR3H comprises SEQ ID NO:28, CDR1L comprises SEQ ID NO:29, CDR2L comprises SEQ ID NO:30, and CDR3L comprises SEQ ID NO:31.

Provided herein is an anti-Mtb AM antibody, or Mtb AM-binding fragment thereof, that comprises a heavy chain variable region that is at least 80%, at least 85%, at least 90%, at least 95%, at least 96%, at least 97%, at least 98%, or at least 99% identical to SEQ ID NO:7.

Provided herein is an anti-Mtb AM antibody, or Mtb AM-binding fragment thereof, that comprises a light chain variable region that is at least 80%, at least 85%, at least 90%, at least 95%, at least 96%, at least 97%, at least 98%, or at least 99% identical to SEQ ID NO:8.

Provided herein is an anti-Mtb AM antibody, or Mtb AM-binding fragment thereof, that comprises (1) a heavy chain variable region that is at least 80%, at least 85%, at least 90%, at least 95%, at least 96%, at least 97%, at least 98%, or at least 99% identical to SEQ ID NO:7 and (2) a light chain variable region that is at least 80%, at least 85%, at least 90%, at least 95%, at least 96%, at least 97%, at least 98%, or at least 99% identical to SEQ ID NO:8.

Provided herein is an anti-Mtb AM antibody, or Mtb AM-binding fragment thereof, that comprises (1) a heavy chain variable region that is at least 95% identical to SEQ ID NO:7 and (2) a light chain variable region that is at least 95% identical to SEQ ID NO:8.

Provided herein is an anti-Mtb AM antibody, or Mtb AM-binding fragment thereof, that comprises (1) a heavy chain variable region that is at least 96% identical to SEQ ID NO:7 and (2) a light chain variable region that is at least 96% identical to SEQ ID NO:8

Provided herein is an anti-Mtb AM antibody, or Mtb AM-binding fragment thereof, that comprises (1) a heavy chain variable region that is at least 97% identical to SEQ ID NO:7 and (2) a light chain variable region that is at least 97% identical to SEQ ID NO: 8.

Provided herein is an anti-Mtb AM antibody, or Mtb AM-binding fragment thereof, that comprises (1) a heavy chain variable region that is at least 98% identical to SEQ ID NO:7 and (2) a light chain variable region that is at least 98% identical to SEQ ID NO:8.

Provided herein is an anti-Mtb AM antibody, or Mtb AM-binding fragment thereof, that comprises (1) a heavy chain variable region that is at least 99% identical to SEQ ID NO:7 and (2) a light chain variable region that is at least 99% identical to SEQ ID NO:8

Provided herein is an anti-Mtb AM antibody, or Mtb AM-binding fragment thereof, that comprises (1) a heavy chain variable region comprising SEQ ID NO:7 and (2) a light chain variable region comprising SEQ ID NO:8

Provided herein is an anti-Mtb AM antibody, or Mtb AM-binding fragment thereof, that comprises a heavy chain variable region that is at least 80%, at least 85%, at least 90%, at least 95%, at least 96%, at least 97%, at least 98%, or at least 99% identical to SEQ ID NO:32.

Provided herein is an anti-Mtb AM antibody, or Mtb AM-binding fragment thereof, that comprises a light chain variable region that is at least 80%, at least 85%, at least 90%, at least 95%, at least 96%, at least 97%, at least 98%, or at least 99% identical to SEQ ID NO:34.

Provided herein is an anti-Mtb AM antibody, or Mtb AM-binding fragment thereof, that comprises (1) a heavy chain variable region that is at least 80%, at least 85%, at least 90%, at least 95%, at least 96%, at least 97%, at least 98%, or at least 99% identical to SEQ ID NO:32 and (2) a light chain variable region that is at least 80%, at least 85%, at least 90%, at least 95%, at least 96%, at least 97%, at least 98%, or at least 99% identical to SEQ ID NO:34.

Provided herein is an anti-Mtb AM antibody, or Mtb AM-binding fragment thereof, that comprises (1) a heavy chain variable region that is at least 95% identical to SEQ ID NO:32 and (2) a light chain variable region that is at least 95% identical to SEQ ID NO:34.

Provided herein is an anti-Mtb AM antibody, or Mtb AM-binding fragment thereof, that comprises (1) a heavy chain variable region that is at least 96% identical to SEQ ID NO:32 and (2) a light chain variable region that is at least 96% identical to SEQ ID NO:34

Provided herein is an anti-Mtb AM antibody, or Mtb AM-binding fragment thereof, that comprises (1) a heavy chain variable region that is at least 97% identical to SEQ ID NO:32 and (2) a light chain variable region that is at least 97% identical to SEQ ID NO:34.

Provided herein is an anti-Mtb AM antibody, or Mtb AM-binding fragment thereof, that comprises (1) a heavy chain variable region that is at least 98% identical to SEQ ID NO:32 and (2) a light chain variable region that is at least 98% identical to SEQ ID NO:34.

Provided herein is an anti-Mtb AM antibody, or Mtb AM-binding fragment thereof, that comprises (1) a heavy chain variable region that is at least 99% identical to SEQ ID NO:32 and (2) a light chain variable region that is at least 99% identical to SEQ ID NO:34

Provided herein is an anti-Mtb AM antibody, or Mtb AM-binding fragment thereof, that comprises (1) a heavy chain variable region comprising SEQ ID NO:32 and (2) a light chain variable region comprising SEQ ID NO:34

Provided herein is an anti-*Mycobacterium tuberculosis* arabinomannan (anti-Mtb AM) antibody, or *Mycobacterium tuberculosis* arabinomannan-binding fragment (Mtb AM-binding fragment) thereof, wherein said antibody or fragment thereof comprises a heavy chain variable region and a light chain variable region, wherein each of the heavy chain and the light chain variable regions comprises a CDR1, CDR2, and CDR3; and wherein:

(a) CDR1H comprises SEQ ID NO:1, CDR2H comprises SEQ ID NO:2, CDR3H comprises SEQ ID NO:3, CDR1L comprises SEQ ID NO:4, CDR2L comprises SEQ ID NO:5, and CDR3L comprises SEQ ID NO:6;
(b) the heavy chain variable region comprises a sequence that is at least 80%, at least 85%, at least 90%, at least 95%, at least 96%, at least 97%, at least 98%, or at least 99% identical to SEQ ID NO:7; and
(c) the light chain variable region comprises a sequence that is at least 80%, at least 85%, at least 90%, at least 95%, at least 96%, at least 97%, at least 98%, or at least 99% identical to SEQ ID NO:8.

Provided herein is an anti-*Mycobacterium tuberculosis* arabinomannan (anti-Mtb AM) antibody, or *Mycobacterium tuberculosis* arabinomannan-binding fragment (Mtb AM-binding fragment) thereof, wherein said antibody or fragment thereof comprises a heavy chain variable region and a light chain variable region, wherein each of the heavy chain and the light chain variable regions comprises a CDR1, CDR2, and CDR3; and wherein:

(a) CDR1H comprises SEQ ID NO:11, CDR2H comprises SEQ ID NO:12, CDR3H comprises SEQ ID NO:13, CDR1L comprises SEQ ID NO:14, CDR2L comprises SEQ ID NO:15, and CDR3L comprises SEQ ID NO:16;
(b) the heavy chain variable region comprises a sequence that is at least 80%, at least 85%, at least 90%, at least 95%, at least 96%, at least 97%, at least 98%, or at least 99% identical to SEQ ID NO:7; and
(c) the light chain variable region comprises a sequence that is at least 80%, at least 85%, at least 90%, at least 95%, at least 96%, at least 97%, at least 98%, or at least 99% identical to SEQ ID NO:8.

Provided herein is an anti-*Mycobacterium tuberculosis* arabinomannan (anti-Mtb AM) antibody, or *Mycobacterium tuberculosis* arabinomannan-binding fragment (Mtb AM-binding fragment) thereof, wherein said antibody or fragment thereof comprises a heavy chain variable region and a light chain variable region, wherein each of the heavy chain and the light chain variable regions comprises a CDR1, CDR2, and CDR3; and wherein:

(a) CDR1H comprises SEQ ID NO:26, CDR2H comprises SEQ ID NO:27, CDR3H comprises SEQ ID NO:28, CDR1L comprises SEQ ID NO:29, CDR2L comprises SEQ ID NO:30, and CDR3L comprises SEQ ID NO:31;
(b) the heavy chain variable region comprises a sequence that is at least 80%, at least 85%, at least 90%, at least 95%, at least 96%, at least 97%, at least 98%, or at least 99% identical to SEQ ID NO:32; and
(c) the light chain variable region comprises a sequence that is at least 80%, at least 85%, at least 90%, at least 95%, at least 96%, at least 97%, at least 98%, or at least 99% identical to SEQ ID NO:34.

As used herein, the term "identity" refers to sequence identity between two nucleic acid molecules or polypeptides. Identity can be determined by comparing a position in each sequence, which may be aligned for purposes of comparison. For example, when a position in the compared nucleotide sequence is occupied by the same base, then the molecules are identical at that position. A degree identity between nucleic acid or amino acid sequences is a function of the number of identical or matching nucleotides or amino acids at shared positions. For example, polypeptides having at least 85%, at least 90%, at least 95%, at least 96%, at least 97%, at least 98%, or at least 99% identity to specific polypeptides described herein and preferably exhibiting substantially the same functions, as well as polynucleotides encoding such polypeptides, are contemplated. Methods and computer programs for determining both sequence identity and similarity are publicly available, including, but not limited to, the GCG program package (Devereux et al., Nucleic Acids Research 12: 387, 1984), BLASTP, BLASTN, FASTA (Altschul et al., J. Mol. Biol. 215:403 (1990), and the ALIGN program (version 2.0). The well-known Smith Waterman algorithm may also be used to determine similarity. The BLAST program is publicly available from NCBI and other sources (BLAST Manual, Altschul, et al., NCBI NLM NIH, Bethesda, Md. 20894; BLAST 2.0 at http://www.ncbi.nlm.nih.gov/blast/). In comparing sequences, these methods account for various substitutions, deletions, and other modifications.

The antibodies disclosed herein may comprises modifications in their variable and their constant regions. For example, provides herein are antibodies comprising modified, but functionally equivalent variable regions and/or CDRs. In some embodiments, the modification does not significantly affect the properties of the antibody or antigen-binding fragment thereof. In some embodiments, the modification leads to enhanced or decreased activity and/or affinity. For example, the amino acid sequence may be mutated to obtain an antibody with the desired binding affinity to Mtb AM. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody or antigen-binding fragment thereof with an enzyme or a polypeptide which increases the half-life of the antibody in the blood circulation.

Substitution variants of the antibodies and antigen-binding fragments thereof have at least one amino acid residue in the antibody molecule removed and a different residue inserted in its place. Substitutional mutagenesis may be directed to the hypervariable regions, but framework alterations are also contemplated. Examples of conservative substitutions are shown in Table 1.

TABLE 1

Conservative amino acid substitutions.

| Original Residue | Conservative Substitutions |
|---|---|
| Ala (A) | Val |
| Arg (R) | Lys |
| Asn (N) | Gln |
| Asp (D) | Glu |
| Cys (C) | Ser |
| Gln (Q) | Asn |
| Glu (E) | Asp |
| Gly (G) | Ala |
| His (H) | Arg |
| Ile (I) | Leu |
| Leu (L) | Ile |
| Lys (K) | Arg |
| Met (M) | Leu |
| Phe (F) | Tyr |
| Pro (P) | Ala |
| Ser (S) | Thr |
| Thr (T) | Ser |
| Trp (W) | Tyr |
| Tyr (Y) | Phe |
| Val (V) | Leu |

Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Conservative substitutions can also be made by exchanging a member of one of these classes for another member of the class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

In embodiments, the anti-Mtb AM antibody is a monoclonal antibody or the anti-Mtb AM-binding fragment thereof is a fragment of a monoclonal antibody. The term "monoclonal antibody" as used herein refers to an antibody member of a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target an Mtb capsular AM, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. Thus, an identified monoclonal antibody can be produced by non-hybridoma techniques, e.g., by appropriate recombinant means once the sequence thereof is identified.

In some embodiments, the anti-Mtb AM antibody is a human antibody and/or the anti-Mtb AM-binding fragment thereof is a fragment of a human antibody. As used herein, a "human antibody" is one whose sequences correspond to (i.e., are identical in sequence to) an antibody that could be produced by a human and/or has been made using any of the techniques for making human antibodies as disclosed herein, but not one which has been made in a human. A "human antibody" as used herein can be produced using various techniques known in the art, including phage-display libraries (Hoogenboom and Winter, J. Mol. Biol., 227:381 (1991); Marks et al., J. Mol. Biol., 222:581 (1991), hereby incorporated by reference in their entireties, by methods described in Cole et al., Monoclonal Antibodies and Cancer Therapy, Alan R. Liss, p. 77 (1985) hereby incorporated by reference in its entirety; Boemer et al., J. Immunol., 147(1): 86-95 (1991) hereby incorporated by reference in its entirety, van Dijk and van de Winkel, Curr. Opin. Pharmacol., 5: 368-74 (2001) hereby incorporated by reference in its entirety, and by administering the antigen (e.g., Mtb capsular AM or an entity comprising such) to a transgenic animal that has been modified to produce such antibodies in response to antigenic challenge, but whose endogenous loci have been disabled, e.g., immunized xenomice (see, e.g., U.S. Pat. Nos. 5,939,598; 6,075,181; 6,114,598; 6,150,584 and 6,162,963 to Kucherlapati et al. regarding XENOM- OUSE™ technology, each of which patents are hereby incorporated by reference in their entireties), e.g., VelocImmune® (Regeneron, Tarrytown, NY), e.g., UltiMab® platform (Medarex, now Bristol Myers Squibb, Princeton, NJ). See also, for example, Li et al., Proc. Natl. Acad. Sci. USA, 103:3557-3562 (2006) regarding human antibodies generated via a human B-cell hybridoma technology. See also KM Mouse® system, described in PCT Publication WO 02/43478 by Ishida et al., in which the mouse carries a human heavy chain transchromosome and a human light chain transgene, and the TC mouse system, described in Tomizuka et al. (2000) Proc. Natl. Acad. Sci. USA 97:722-727, in which the mouse carries both a human heavy chain transchromosome and a human light chain transchromosome, both of which are hereby incorporated by reference in their entireties. In each of these systems, the transgenes and/or transchromosomes carried by the mice comprise human immunoglobulin variable and constant region sequences. The term "human antibody", as used herein, is intended to include antibodies having variable regions in which both the framework and CDR regions are sequences of human origin or identical thereto other than antibodies naturally occurring in a human or made in a human. Furthermore, if the antibody (e.g., an intact antibody rather than, for example, a Fab fragment) contains a constant region, the constant region also is derived from such human sequences, e.g., human germline sequences, or mutated versions of human germline sequences. The human antibodies disclosed herein may include amino acid residues not encoded by human sequences (e.g., mutations introduced by random or site-specific mutagenesis in vitro or by somatic mutation in vivo). In one non-limiting embodiment, where the human antibodies are human monoclonal antibodies, such antibodies can be produced by a hybridoma which includes a B cell obtained from a transgenic nonhuman animal, e.g., a transgenic mouse, having a genome comprising a human heavy chain transgene and a light chain transgene fused to an immortalized cell.

In embodiments, the anti-Mtb AM antibody, or Mtb AM-binding fragment thereof, has a human framework region. In embodiments, the anti-Mtb AM antibody, or Mtb AM-binding fragment thereof, comprises (i) a VH framework comprising the framework sequence of germline VH3-23*01 and/or (ii) a VK framework comprising the framework sequence of human germline 2-24*01. In embodiments, the anti-Mtb AM antibody, or Mtb AM-binding fragment thereof, comprises (i) a VH framework comprising the framework sequence of human germline VH 4-59*08; and/or (ii) a VL framework comprising the framework sequence of human germline VL 1-51*02.

In embodiments, the anti-Mtb AM antibody, or Mtb AM-binding fragment thereof, is a recombinant antibody. The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created, or isolated by any other means that involve splicing of all or a portion of a human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

In some embodiments, the anti-Mtb AM antibody, or Mtb AM-binding fragment thereof is isolated. As used herein, the term "isolated antibody" refers to an antibody that by virtue of its origin or source of derivation meets one, two, three or four of the following criteria: (1) is not substantially associated with naturally associated components that accompany it in its native state, (2) is substantially free of other proteins from the same species, (3) is expressed by a cell from a different species, and (4) does not occur in nature.

In embodiments, the anti-Mtb AM antibody, or Mtb AM-binding fragment thereof, comprises a human constant region or modified constant region. In some embodiments, the anti-Mtb AM antibody or Mtb AM-binding fragment thereof has a non-human constant region or a modified non-human constant region. In one embodiment, the anti-Mtb AM antibody or Mtb AM-binding fragment thereof has murine constant region or modified murine constant region. In one embodiment, the anti-Mtb AM antibody or Mtb AM-binding fragment thereof has a non-human primate constant region or modified non-human primate constant region. In some embodiments, the anti-Mtb AM antibody or Mtb AM-binding fragment thereof has a non-human constant region or a modified non-human constant region. In some embodiments, constant region is from a non-human primate, a mouse, a rat, a sheep, a goat, or a rabbit.

In embodiments, the antibody comprises an Fe domain. The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine of the Fc region may be removed, for example, during production or purification of the antibody, or by recombinantly engineering the nucleic acid encoding a heavy chain of the antibody. Accordingly, an intact antibody as used herein may be an antibody with or without the otherwise C-terminal lysine.

Depending on the amino acid sequences of the constant domains of their heavy chains, antibodies (immunoglobulins) can be assigned to different classes. The antibody or antigen-binding fragment can be, e.g., any of an IgG, IgD, IgE, IgA or IgM antibody or fragment thereof, respectively. In an embodiment the antibody is an immunoglobulin G. In an embodiment the antibody fragment is a fragment of an immunoglobulin G. In an embodiment the antibody is an IgG1, IgG2, IgG2a, IgG2b, IgG3 or IgG4. In an embodiment the antibody comprises sequences from a human IgG1, human IgG2, human IgG3 or human IgG4. A combination of any of these antibodies subtypes can also be used. One consideration in selecting the type of antibody to be used is the desired serum half-life of the antibody. For example, an IgG generally has a serum half-life of 23 days, IgA 6 days, IgM 5 days, IgD 3 days, and IgE 2 days. (Abbas A K, Lichtman A H, Pober J S. Cellular and Molecular Immunology, 4th edition, W.B. Saunders Co., Philadelphia, 2000, hereby incorporated by reference in its entirety).

In an embodiment, anti-Mtb AM antibody, or Mtb AM-binding fragment thereof, comprises an Fe domain that has the same sequence or 99% or greater sequence similarity with a human IgG1 Fc domain. In an embodiment, the anti-Mtb AM antibody, or Mtb AM-binding fragment thereof, comprises an Fe domain that has the same sequence or 99% or greater sequence similarity with a human IgG2 Fc domain. In an embodiment, the anti-Mtb AM antibody, or Mtb AM-binding fragment thereof, comprises an Fc domain that has the same sequence or 99% or greater sequence similarity with a human IgG3 Fc domain. In an embodiment, the anti-Mtb AM antibody, or Mtb AM-binding fragment thereof, comprises an Fc domain that has the same sequence or 99% or greater sequence similarity with a human IgG4 Fc domain. In an embodiment, the Fc domain is not mutated.

In an embodiment, the Fc domain is mutated at the CH2-CH3 domain interface to increase the affinity of IgG for FcRn at acidic but not neutral pH. In an embodiment, the anti-Mtb AM antibody, or Mtb AM-binding fragment thereof, comprises an Fc domain that has the same sequence as a human IgG1 Fe domain.

In some embodiment, the anti-Mtb AM antibody, or Mtb AM-binding fragment thereof, has a modified IgG Fc region. Modified IgG Fc regions are well known in the art. For example, see any of the mutations listed in Table 1 of Wang et al. Protein Cell (2018), 9(1):63-73. In embodiments, the modified Fc region, relative to the unmodified Fc region, has enhanced complement-based effector function, increased or decreased FcγR-based effector function, reduced effector function, enhanced coengagement of antigen and FcγRs, and/or increased serum half-life.

Non-limiting examples of Fc modifications to modulate antibody effector function for IgG1 (see Wang et al. Protein Cell (2018), 9(1):63-73) include are:

- (a) Increased FcγRIIIa binding: F243L/R292P/Y300L/V305I/P396L
- (b) Increased FcγRIIIa binding: S239D/1332E
- (c) Increased FcγRIIIa binding: decreased FcγRIIb binding S239D/I332E/A330L
- (d) Increased FcγRIIIa binding: S298A/E333A/K334A.
  - i. For example, in one heavy chain: L234Y/L235Q/G236W/S239M/H268D/D270E/S298A
  - ii. For example, in the opposing heavy chain: D270E/K326D/A330M/K334E
- (e) Increased FcγRIIa binding, increased FcγRIIIa binding: G236A/S239D/1332E
- (f) Enhanced CDC, increased C1q binding: K326W/E333S
- (g) Increased C1q binding: S267E/1H268F/S324T
- (h) Increased C1q binding, IgG1/IgG3 cross subclass Hexamerization: E345R/E430G/S440Y
- (i) Reduced effector function: Aglycosylated N297A or N297Q or N297G
- (j) Reduced FcγR and C1q binding: L235E
- (k) Reduced FcγR and C1q binding
  - i. IgG1: L234A/L235A
  - ii. IgG4: F234A/L235A
- (l) Reduced FcγR and C1q binding, IgG2/IgG4 cross isotype
- (m) Reduced FcγR and C1q binding IgG2: H268Q/V309L/A330S/P331S
- (n) Reduced FcγR and C1q binding IgG2: V234A/G237A/P238S/H268A/V309L/A330S/P331S
- (o) Increased FcRn binding at pH 6.0: M252Y/S254T/T256E
- (p) Increased FcRn binding at pH 6.0: M428L/N434S
- (q) Increased FcγRIIb binding: S267E/L328F
- (r) Increased FcγRIIa binding, decreased FcγRIIIa binding: N325S/L328F.

In embodiments, the anti-Mtb AM antibody, or Mtb AM-binding fragment thereof, binds Mtb AM with a binding affinity ($K_D$) of from about $1\times10^{-6}$ M to about $1\times10^{-10}$ M, from about $1\times10^{-7}$ M to about $1\times10^{-10}$ M, from about $1\times10^{-8}$ M to about $1\times10^{-10}$ M, from about $1\times10^{-8}$ M to about $1\times10^{-1}$ M. In embodiments, the anti-Mtb AM antibody, or Mtb AM-binding fragment thereof, binds Mtb AM with a binding affinity ($K_D$) of about $1\times10^{-7}$ M, about $1\times10^{-8}$ M, about $1\times10^{-9}$ M, or about $1\times10^{-10}$ M.

The term "$K_D$", as used herein, is intended to refer to the dissociation constant of an antibody-antigen interaction. One way of determining the $K_D$ or binding affinity of antibodies to Mtb capsular AM is by measuring binding affinity Using a Dip and Read assay using an immobilized antigen and monoclonal antibodies (Octet Red96 ForteBio, Fremont, CA). (The affinity constant is the inverted dissociation constant). Biotinylated Mtb capsular AM can be diluted into PBS+0.1% BSA, 0.02% Tween20 and 0.05% sodium azide (Kinetics Buffer, ForteBio) and dipped into wells containing serial diluted mAbs starting from 37.75 nM. The concentrations of the Fab proteins are determined by ELISA and/or SDS-PAGE electrophoresis using an IgG1 standard monoclonal antibody of known concentration as a standard. Kinetic association rates ($k_{on}$) and dissociation rates ($k_{off}$) are obtained simultaneously by fitting the data to a 1:1 Langmuir binding model (Karlsson, R. Roos, H. Fagerstam, L. Petersson, B. (1994). Methods Enzymology 6. 99-110, the content of which is hereby incorporated in its entirety) using the BIA evaluation program. Equilibrium dissociation constant ($K_D$) values are calculated as $k_{off}/k_{on}$. This protocol is suitable for use in determining binding affinity of an antibody or fragment to any Mtb capsular AM. Other protocols known in the art may also be used. For example, ELISA of Mtb capsular AM with mAb can be used to determine the $K_D$ values.

In an embodiment, the Mtb capsular AM antibody described herein is capable of specifically binding or specifically binds an Mtb capsular AM. As used herein, the terms "is capable of specifically binding" or "specifically binds" refers to the property of an antibody or fragment of binding to the specified antigen with a dissociation constant that is <1 μM, preferably <1 nM and most preferably <10 μM. In an embodiment, the $K_D$ of the antibody (or antigen-binding fragment thereof) for Mtb capsular AM is less than 100 nM. In an embodiment, the $K_D$ of the antibody (or antigen-binding fragment thereof) for Mtb capsular AM is less than 10 nM. In an embodiment, the $K_D$ of the antibody (or antigen-binding fragment thereof) for Mtb capsular AM is less than 1.0 nM. In an embodiment, the $K_D$ of the antibody (or fragment) for avirulent Mtb capsular AM is a lower affinity than its $K_D$ for virulent Mtb capsular AM. An epitope that "specifically binds" to an antibody or a polypeptide is a term well understood in the art. A molecular entity is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an Mtb capsular AM conformational epitope is an antibody that binds this epitope with greater affinity, avidity, more readily, and/or with greater duration than it binds to other Mtb capsular AM epitopes or non-Mtb capsular AM epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require, although it can include, exclusive binding.

In embodiments, the antibody, or antigen-binding fragment thereof, binds to a linear epitope. In embodiments, the antibody, or antigen-binding fragment thereof, binds to a linear oligosaccharide epitope.

In one embodiment, an anti-Mtb AM antibody or Mtb AM-binding fragment thereof disclosed herein binds to its antigen with one, two, three four, five, or six CDRs.

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are disclosed herein. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

As used herein, the term "antigen-binding portion" or "antigen-binding fragment" may be a fragment comprising a Fab, Fab', $F(ab')_2$, Fd, Fv, domain antibodies (dAbs such as shark and camel antibodies), ScFv, a maxibody, a minibody, a nanobody, an intrabody, a diabody, a triabody, a tetrabody, a v-NAR and a bis-scFv, or a polypeptide that contain at least certain portions of an immunoglobulin sufficient to confer specific antigen-binding to the polypeptide.

Antibody fragments can be prepared, for example, by cleaving an intact antibody or by recombinant means. See generally, Fundamental Immunology, Ch. 7 (Paul, W., ed., 2nd ed. Raven Press, N.Y. (1989), hereby incorporated by reference in its entirety). Antigen-binding fragments may be produced by recombinant DNA techniques or by enzymatic or chemical cleavage of intact antibodies or by molecular biology techniques.

The antibody may be any class of antibody, such as IgG, IgA, or IgM (or a subclass thereof), and the antibody need not be of any particular class, and any of the immunoglobulin molecules comprising the antigen recognition site of the required specificity, other modified configurations (including glycosylation variants of antibodies, amino acid sequence variants of antibodies, and covalently modified antibodies) can be encompassed. Modified versions of each of these classes and isotypes are known to a person skilled in the art, accordingly, are within the scope of the instant disclosure.

In some embodiments of the aspects described herein, the anti-Mtb AM antibody disclosed herein is a Fab fragment, which comprises or consist essentially of a variable (VL) and constant (CL) domain of the light chain and a variable domain (VH) and the first constant domain (CH1) of the heavy chain.

In some embodiments of the aspects described herein, the anti-Mtb AM antibody fragment is a Fab' fragment, which refers to a Fab fragment having one or more cysteine residues at the C-terminus of the CH1 domain.

In some embodiments of the aspects described herein, the anti-Mtb AM antibody fragment is an Fd fragment comprising or consisting essentially of VH and CH1 domains.

In some embodiments of the aspects described herein, the anti-Mtb AM antibody fragment is an Fd' fragment comprising VH and CH domains and one or more cysteine residues at the C-terminus of the CH1 domain.

Single-chain Fv or scFv antibody fragments comprise or consist essentially of the VH and VL domains of an antibody, such that these domains are present in a single polypeptide chain. Generally, an Fv polypeptide further comprises a polypeptide linker between the VH and VL domains, which allows the scFv to form the desired structure for antigen-binding. Accordingly, in some embodiments of the aspects described herein, the anti-Mtb AM antibody fragment is a Fv fragment comprising or consisting essentially of the VL and VH domains of a single arm of an antibody.

In some embodiments of the aspects described herein, the anti-Mtb AM antibody fragment is a diabody comprising two antigen-binding sites, comprising a heavy chain variable domain (VH) connected to a light chain variable domain (VL) in the same polypeptide chain.

In some embodiments of the aspects described herein, the anti-Mtb AM antibody fragment is a dAb fragment comprising or consisting essentially of a VH domain.

In some embodiments of the aspects described herein, the anti-Mtb AM antibody fragment is a F(ab')2 fragment, which comprises a bivalent fragment comprising two Fab' fragments linked by a disulfide bridge at the hinge region.

In some embodiments of the aspects described herein, the anti-Mtb AM antibody fragment is a linear antibody comprising a pair of tandem Fd segments (VH-CH1-VH-CH1) which, together with complementary light chain polypeptides, form a pair of antigen-binding regions.

A person skilled in the arts can use various techniques that have been developed and are available for the production of antibody fragments. Traditionally, these fragments were derived via proteolytic digestion of intact antibodies. However, F(ab')2 fragments can be isolated directly from recombinant host cell culture. Other techniques for the production of antibody fragments will be apparent to the skilled practitioner. In other embodiments, the antibody fragment of choice is a single chain Fv fragment (scFv). See, for example, WO 93/16185. Alternatively, these fragments can also be produced directly by recombinant host cells. For example, antibody fragments can be isolated from the antibody phage libraries discussed herein. In another approach, Fab'-SH fragments can be directly recovered from *E. coli* and chemically coupled to form $F(ab')_2$ fragments (Carter et al., 1992).

Contemplated antibodies or antigen-binding fragments may have all types of constant regions, including IgM, IgG, IgD, and IgE, and any isotype, including IgG1, IgG2, IgG3, and IgG4. In one embodiment, the isotype is human IgG1. In another embodiment, the human isotype IgG4 is used. Light chain constant regions can be λ or κ. The antibody, or antigen-binding fragment thereof, may comprise sequences from more than one class or isotype.

In some embodiments, the anti-Mtb AM antibody, or antigen-binding fragment thereof, may include a modification, including, but not limited to glycosylation, acetylation, pegylation, phosphorylation, phosphorylation, amidation, derivatization by known protecting/blocking groups, proteolytic cleavage, linkage to a cellular ligand or other protein, etc. The process of making chemical modifications is known in the art, and may include, but are not limited to, specific chemical cleavage, acetylation, formylation, metabolic synthesis of tunicamycin, etc. Additionally, the molecules may contain one or more non-classical amino acids.

In some embodiments of the aspects described herein, the anti-Mtb AM antibody, or antigen-binding fragment thereof, is conjugated to a functional moiety. Examples of useful functional moieties include, but are not limited to, a blocking moiety, a detectable moiety, a diagnostic moiety, a targeting moiety, and a therapeutic moiety.

Exemplary blocking moieties include moieties of sufficient steric bulk and/or charge such that reduced glycosylation occurs, for example, by blocking the ability of a glycosidase to glycosylate the antibody or antigen-binding fragment thereof. The blocking moiety may, additionally or alternatively, reduce effector function, for example, by inhibiting the ability of the Fc region to bind a receptor or complement protein. Preferred blocking moieties include cysteine adducts and PEG moieties.

In one embodiment, the blocking moiety is a cysteine, preferably a cysteine that has associated with a free cysteine, e.g., during or subsequent to the translation of the Fc containing polypeptide, e.g., in cell culture. Other blocking cysteine adducts include cystine, mixed disulfide adducts, or disulfide linkages.

In another embodiment, the blocking moiety is a polyalkylene glycol moiety, for example, a PEG moiety and preferably a PEG-maleimide moiety. Preferred pegylation moieties (or related polymers) can be, for example, polyethylene glycol ("PEG"), polypropylene glycol ("PPG"), polyoxyethylated glycerol ("POG") and other polyoxyethylated polyols, polyvinyl alcohol ("PVA") and other polyalkylene oxides, polyoxyethylated sorbitol, or polyoxyethylated glu-cose. The polymer can be a homopolymer, a random or block copolymer, a terpolymer based on the monomers listed above, straight chain or branched, substituted or unsubstituted as long as it has at least one active sulfone moiety. The polymeric portion can be of any length or molecular weight but these characteristics can affect the biological properties. Polymer average molecular weights particularly useful for decreasing clearance rates in pharmaceutical applications are in the range of 2,000 to 35,000 Daltons. In addition, if two groups are linked to the polymer, one at each end, the length of the polymer can impact upon the effective distance, and other spatial relationships, between the two groups. Thus, one skilled in the art can vary the length of the polymer to optimize or confer the desired biological activity. PEG is useful in biological applications for several reasons. PEG typically is clear, colorless, odorless, soluble in water, stable to heat, inert to many chemical agents, does not hydrolyze, and is nontoxic. Pegylation can im-prove pharmacokinetic performance of a molecule by increasing the molecule's apparent molecular weight. The increased apparent molecular weight reduces the rate of clearance from the body following subcutaneous or systemic administration. In many cases, pegylation can de-crease antigenicity and immunogenicity. In addition, pegylation can increase the solubility of a biologically-active molecule.

Examples of detectable moieties for the detection of the anti-Mtb AM antibodies and Mtb AM-binding fragments thereof contemplated by the disclosure include fluorescent moieties or labels, imaging agents, radioisotopic moieties, radiopaque moieties, and the like, e.g. detectable labels such as biotin, fluorophores, chromophores, spin resonance probes, or radiolabels. Exemplary fluorophores include fluorescent dyes (e.g. fluorescein, rhodamine, and the like) and other luminescent molecules (e.g. luminol). A fluorophore may be environmentally-sensitive such that its fluorescence changes if it is located close to one or more residues in the modified protein that undergo structural changes upon binding a substrate (e.g. dansyl probes). Exemplary radiolabels include small molecules containing atoms with one or more low sensitivity nuclei ($^{13}C$, $^{15}N$, $^{2}H$, $^{125}I$, $^{123}I$, $^{99}Tc$, $^{43}K$, $^{52}Fe$, $^{67}Ga$, $^{68}Ga$, $^{111}In$ and the like). Other useful moieties are known in the art.

Examples of therapeutic moieties include anti-tuberculosis agents. Anti-tuberculosis agents include, but are not limited to, ethambutol, pyrazinamide, streptomycin, isoniazid, moxifloxacin rifampicin, levofloxacin, moxifloxacin, clofazimine, bedaquiline, cycloserine, terizidone, delamanid, linezolid, pyrazinamide, imipenem-cilastatin (Ipm-Cln) or Meropenem, amikacin, streptomycin, ethionamide, Prothionamide, and p-aminosalicylic acid.

The functional moiety may also have one or more of the above-mentioned functions.

To increase the half-life of the antibodies or polypeptides containing the amino acid sequences described herein, one can attach a salvage receptor binding epitope to the anti-Mtb AM antibody or Mtb AM-binding fragment thereof (especially an antibody fragment), as described, e.g., in U.S. Pat. No. 5,739,277. The term "salvage receptor binding epitope" may refer to an epitope of the Fc region of an IgG molecule (e.g., IgG1, IgG2, IgG3, or IgG4) that is responsible for in-creasing the in vivo serum half-life of the IgG molecule (e.g., Ghetie et al., 18 Ann. Rev. Immunol. 739 (2000). Antibodies with substitutions in an Fc region thereof and increased serum half-lives are also described in WO 00/42072, WO 02/060919; Shields et al., 276 J. Biol. Chem. 6591 (2001); Hinton, 279 J. Biol. Chem. 6213-6216 (2004). For example, a nucleic acid molecule encoding the salvage receptor binding epitope can be linked in frame to a nucleic acid encoding a polypeptide sequence described herein so that the fusion protein expressed by the engineered nucleic acid molecule comprises the salvage receptor binding epitope and a polypeptide sequence described herein. In another embodiment, the serum half-life can also be increased, for example, by attaching other polypeptide sequences.

Other types of functional moieties are known in the art and can be readily used in the methods and compositions of the present disclosure based on the teachings contained herein.

Also provided herein are nucleic acids encoding the anti-Mtb AM antibody, or Mtb AM-binding fragment thereof, as well as vectors, host cells, and expression systems. The term "nucleic acid" as used herein refers to a polymeric form of nucleotides of any length, either ribonucleotides or desoxyribonucleotides. Thus, this term includes, but is not limited to, single-double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases.

In some embodiments, provided is a nucleic acid sequence comprising a sequence that is at least 80%, at least 85%, at least 90%, at least 95%, at least 96%, at least 97%, at least 98%, or at least 99% identical to SEQ ID NO:9. In some embodiments, provided is a nucleic acid sequence comprising a sequence that is at least 80%, at least 85%, at least 90%, at least 95%, at least 96%, at least 97%, at least 98%, or at least 99% identical to SEQ ID NO:10. In some embodiments, provided is a nucleic acid sequence comprising a sequence that is at least 80%, at least 85%, at least 90%, at least 95%, at least 96%, at least 97%, at least 98%, or at least 99% identical to SEQ ID NO:9 and a sequence that is at least 80%, at least 85%, at least 90%, at least 95%, at least 96%, at least 97%, at least 98%, or at least 99% identical to SEQ ID NO:10.

In some embodiments, provided is a nucleic acid sequence comprising a sequence that is at least 80%, at least 85%, at least 90%, at least 95%, at least 96%, at least 97%, at least 98%, or at least 99% identical to SEQ ID NO:33. In some embodiments, provided is a nucleic acid sequence comprising a sequence that is at least 80%, at least 85%, at least 90%, at least 95%, at least 96%, at least 97%, at least 98%, or at least 99% identical to SEQ ID NO:35. In some embodiments, provided is a nucleic acid sequence comprising a sequence that is at least 80%, at least 85%, at least 90%, at least 95%, at least 96%, at least 97%, at least 98%, or at least 99% identical to SEQ ID NO:33 and a sequence that is at least 80%, at least 85%, at least 90%, at least 95%, at least 96%, at least 97%, at least 98%, or at least 99% identical to SEQ ID NO:35.

In one embodiment, a nucleic acid provided herein encoding an anti-Mtb AM antibody, or Mtb AM-binding fragment thereof is codon-optimized.

The nucleic acids encoding the anti-Mtb AM antibody, or Mtb AM-binding fragment thereof, may be, e.g., DNA, cDNA, RNA, synthetically produced DNA or RNA, or a recombinantly produced chimeric nucleic acid molecule comprising any of those polynucleotides either alone or in combination. For example, provided is an expression vector or set of expression vectors comprising a polynucleotide sequence encoding an anti-Mtb AM antibody, or Mtb AM-binding fragment thereof, described herein operably linked to expression control sequences suitable for expression in a eukaryotic and/or prokaryotic host cell.

The term "vector" refers to a nucleic acid molecule capable of transporting another nucleic acid to which it has been linked. A "vector" includes, but is not limited to, a viral vector, a plasmid, an RNA vector or a linear or circular DNA or RNA molecule which may consists of a chromosomal, non-chromosomal, semi-synthetic or synthetic nucleic acids. In some embodiments, the employed vectors are those capable of autonomous replication (episomal vector) and/or expression of nucleic acids to which they are linked (expression vectors). Large numbers of suitable vectors are known to those of skill in the art and commercially available. Viral vectors include retrovirus, adenovirus, parvovirus (e.g., adeno associated viruses, AAV), coronavirus, negative strand RNA viruses such as orthomyxovirus (e.g., influenza virus), rhabdovirus (e. g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, and spumavirus.

n some embodiments, provided is a vector comprising a nucleic acid sequence comprising a sequence that is at least 80%, at least 85%, at least 90%, at least 95%, at least 96%, at least 97%, at least 98%, or at least 99% identical to SEQ ID NO:9. In some embodiments, provided is a vector comprising a nucleic acid sequence comprising a sequence that is at least 80%, at least 85%, at least 90%, at least 95%, at least 96%, at least 97%, at least 98%, or at least 99% identical to SEQ ID NO:10. In some embodiments, provided is a vector or a set of vectors comprising (1) a nucleic acid sequence comprising a sequence that is at least 80%, at least 85%, at least 90%, at least 95%, at least 96%, at least 97%, at least 98%, or at least 99% identical to SEQ ID NO:9 and (2) a nucleic acid sequence comprising a sequence that is at least 80%, at least 85%, at least 90%, at least 95%, at least 96%, at least 97%, at least 98%, or at least 99% identical to SEQ ID NO:10. In some embodiments, provided is a vector or a set of vectors comprising SEQ ID NO:9 and SEQ ID NO:10.

In some embodiments, provided is a vector comprising a nucleic acid sequence comprising a sequence that is at least 80%, at least 85%, at least 90%, at least 95%, at least 96%, at least 97%, at least 98%, or at least 99% identical to SEQ ID NO:33. In some embodiments, provided is a vector comprising a nucleic acid sequence comprising a sequence that is at least 80%, at least 85%, at least 90%, at least 95%, at least 96%, at least 97%, at least 98%, or at least 99% identical to SEQ ID NO:35. In some embodiments, provided is a vector or a set of vectors comprising (1) a nucleic acid sequence comprising a sequence that is at least 80%, at least 85%, at least 90%, at least 95%, at least 96%, at least 97%, at least 98%, or at least 99% identical to SEQ ID NO:33 and (2) a nucleic acid sequence comprising a sequence that is at least 80%, at least 85%, at least 90%, at least 95%, at least 96%, at least 97%, at least 98%, or at least 99% identical to SEQ ID NO:35. In some embodiments, provided is a vector or a set of vectors comprising SEQ ID NO:33 and SEQ ID NO:35.

A variety of expression vectors have been developed for the efficient synthesis of the anti-Mtb AM antibody, or Mtb AM-binding fragment thereof, in prokaryotic cells such as bacteria and in eukaryotic systems, including but not limited to yeast and mammalian cell culture systems have been developed. The vectors can comprise segments of chromosomal, non-chromosomal and synthetic DNA sequences. Also provided are cells comprising expression vectors for the expression of the disclosed the anti-Mtb AM antibody, or Mtb AM-binding fragment thereof.

In an embodiment, a host cell comprising a nucleic acid molecule described herein, or a vector described herein, is provided.

In an embodiment, provided is a method of producing an anti-Mtb AM antibody, or Mtb AM-binding fragment thereof, disclosed herein comprising culturing a cell comprising one or more nucleic acid molecules encoding for an anti-Mtb AM antibody, or Mtb AM-binding fragment thereof, disclosed herein under conditions whereby the anti-Mtb AM antibody, or Mtb AM-binding fragment thereof, is produced by the host cell.

Provided herein is a method of making an anti-Mtb AM antibody, or Mtb AM-binding fragment thereof, disclosed herein, the method comprising:

(a) cultivating a cell comprising one or more nucleic acid molecules encoding an anti-Mtb AM antibody, or Mtb AM-binding fragment thereof, under conditions whereby the anti-Mtb AM antibody, or Mtb AM-binding fragment thereof, is produced by the host cell, wherein the anti-Mtb AM antibody, or Mtb AM-binding fragment thereof, comprises a heavy chain variable region and a light chain variable region, wherein each of the heavy chain and the light chain variable regions comprises a CDR1, CDR2, and CDR3; and wherein CDR1H comprises SEQ ID NO:1, CDR2H comprises SEQ ID NO:2, CDR3H comprises SEQ ID NO:3, CDR1L comprises SEQ ID NO:4, CDR2L comprises SEQ ID NO:5, and CDR3L comprises SEQ ID NO:6, and (b) optionally, substantially isolating the an anti-Mtb AM antibody, or Mtb AM-binding fragment thereof.

Provided herein is a method of making an anti-Mtb AM antibody, or Mtb AM-binding fragment thereof, disclosed herein, the method comprising:

(a) cultivating a cell comprising one or more nucleic acid molecules encoding an anti-Mtb AM antibody, or Mtb AM-binding fragment thereof, under conditions whereby the anti-Mtb AM antibody, or Mtb AM-binding fragment thereof, is produced by the host cell, wherein the anti-Mtb AM antibody, or Mtb AM-binding fragment thereof, comprises a heavy chain variable region and a light chain variable region, wherein each of the heavy chain and the light chain variable regions comprises a CDR1, CDR2, and CDR3; and wherein CDR1H comprises SEQ ID NO:11, CDR2H comprises SEQ ID NO:12, CDR3H comprises SEQ ID NO:13, CDR1L comprises SEQ ID NO:14, CDR2L comprises SEQ ID NO:15, and CDR3L comprises SEQ ID NO:16, and (b) optionally, substantially isolating the an anti-Mtb AM antibody, or Mtb AM-binding fragment thereof.

Provided herein is a method of making an anti-Mtb AM antibody, or Mtb AM-binding fragment thereof, disclosed herein, the method comprising:

(a) cultivating a cell comprising one or more nucleic acid molecules encoding an anti-Mtb AM antibody, or Mtb AM-binding fragment thereof, under conditions whereby the anti-Mtb AM antibody, or Mtb AM-binding fragment thereof, is produced by the host cell, wherein the anti-Mtb AM antibody, or Mtb AM-binding fragment thereof, comprises a heavy chain variable region and a light chain variable region, wherein each of the heavy chain and the light chain variable regions comprises a CDR1, CDR2, and CDR3; and wherein CDR1H comprises SEQ ID NO:26, CDR2H comprises SEQ ID NO:27, CDR3H comprises SEQ ID NO:28, CDR1L comprises SEQ ID NO:29, CDR2L comprises SEQ ID NO:30, and CDR3L comprises SEQ ID NO:31, and (b) optionally, substantially isolating the an anti-Mtb AM antibody, or Mtb AM-binding fragment thereof.

Provided herein is a method of making an anti-Mtb AM antibody, or Mtb AM-binding fragment thereof, disclosed herein, the method comprising:

(a) cultivating a cell comprising one or more nucleic acid molecules encoding an anti-Mtb AM antibody, or Mtb AM-binding fragment thereof, under conditions whereby the anti-Mtb AM antibody, or Mtb AM-binding fragment thereof, is produced by the host cell, wherein the anti-Mtb AM antibody, or Mtb AM-binding fragment thereof, comprises a heavy chain variable region and a light chain variable region, wherein the heavy chain variable region comprises a sequence that is at least 80%, at least 85%, at least 90%, at least 95%, at least 96%, at least 97%, at least 98%, or at least 99% identical to SEQ ID NO:7 and wherein the light chain variable region comprises a sequence that is at least 80%, at least 85%, at least 90%, at least 95%, at least 96%, at least 97%, at least 98%, or at least 99% identical to SEQ ID NO:8, and (b) optionally, substantially isolating the an anti-Mtb AM antibody, or Mtb AM-binding fragment thereof.

Provided herein is a method of making an anti-Mtb AM antibody, or Mtb AM-binding fragment thereof, disclosed herein, the method comprising:

(a) cultivating a cell comprising one or more nucleic acid molecules encoding an anti-Mtb AM antibody, or Mtb AM-binding fragment thereof, under conditions whereby the anti-Mtb AM antibody, or Mtb AM-binding fragment thereof, is produced by the host cell, wherein the anti-Mtb AM antibody, or Mtb AM-binding fragment thereof, comprises a heavy chain variable region and a light chain variable region, wherein the heavy chain variable region comprises a sequence that is at least 80%, at least 85%, at least 90%, at least 95%, at least 96%, at least 97%, at least 98%, or at least 99% identical to SEQ ID NO:32 and wherein the light chain variable region comprises a sequence that is at least 80%, at least 85%, at least 90%, at least 95%, at least 96%, at least 97%, at least 98%, or at least 99% identical to SEQ ID NO:34, and (b) optionally, substantially isolating the an anti-Mtb AM antibody, or Mtb AM-binding fragment thereof.

Provided herein is a method of making an anti-Mtb AM antibody, or Mtb AM-binding fragment thereof, disclosed herein, the method comprising:

(a) cultivating a cell comprising one or more nucleic acid molecules encoding an anti-Mtb AM antibody, or Mtb AM-binding fragment thereof, under conditions whereby the anti-Mtb AM antibody, or Mtb AM-binding fragment thereof, is produced by the host cell, wherein the anti-Mtb AM antibody, or Mtb AM-binding fragment thereof, comprises a heavy chain variable region and a light chain variable region, wherein the heavy chain variable region comprises SEQ ID NO:7 and wherein the light chain variable region comprises SEQ ID NO:8, and (b) optionally, substantially isolating the an anti-Mtb AM antibody, or Mtb AM-binding fragment thereof.

Provided herein is a method of making an anti-Mtb AM antibody, or Mtb AM-binding fragment thereof, disclosed herein, the method comprising:

(a) cultivating a cell comprising one or more nucleic acid molecules encoding an anti-Mtb AM antibody, or Mtb AM-binding fragment thereof, under conditions whereby the anti-Mtb AM antibody, or Mtb AM-binding fragment thereof, is produced by the host cell, wherein the anti-Mtb AM antibody, or Mtb AM-binding fragment thereof, comprises a heavy chain variable region and a light chain variable region, wherein the heavy chain variable region comprises SEQ ID NO:32 and wherein the light chain variable region comprises SEQ ID NO:34, and (b) optionally, substantially isolating the an anti-Mtb AM antibody, or Mtb AM-binding fragment thereof.

The anti-Mtb AM antibodies, or Mtb AM-binding fragments thereof, disclosed herein are typically produced by recombinant expression. Nucleic acids encoding light and heavy chain variable regions, optionally linked to constant regions, may be inserted into the same expression vectors. Alternatively, the nucleic acids encoding light and heavy chain variable regions, optionally linked to constant regions, are inserted into different expression vectors. The expression vector may further comprise one or more expression control sequences, which include, but are not limited to, promoters (e.g., homologous or heterologous promoters), signal sequences, enhancer elements, and transcription termination sequences. Preferably, the expression control sequences are eukaryotic promoter systems in vectors capable of transforming or transfecting eukaryotic host cells. Typically, the host is maintained under conditions suitable for high-level expression of the nucleotide sequences, and the collection and purification of the cross-reacting antibodies after the vector is incorporated into the appropriate host.

Commonly, expression vectors contain selection markers (e.g., ampicillin-resistance, hygromycin-resistance, tetracycline resistance or neomycin resistance) to permit detection of those cells transformed with the desired DNA sequences.

The host used to express the anti-Mtb AM antibodies, or Mtb AM-binding fragments thereof, disclosed herein can be a prokaryotic or eukaryotic host. Examples of suitable hosts include bacterial or eukaryotic hosts, including yeast, insects, fungi, bird and mammalian cells either in vivo, or in situ, or host cells of mammalian, insect, bird, or yeast origin. The mammalian cell or tissue can be of human, primate, hamster, rabbit, rodent, cow, pig, sheep, horse, goat, dog, or cat origin, but any other mammalian cell may be used.

Examples of bacterial hosts that can be used to express the antibodies, antigen-binding fragments or the fusion protein disclosed herein can be *E. coli*, bacilli, such as *Bacillus subtilis*, and other enterobacteriaceae, such as *Salmonella, Serratia*, and various *Pseudomonas* species.

Yeasts may also be used as hosts for expressing the express the antibodies, antigen-binding fragments or the fusion protein disclosed herein. *Saccharomyces* and *Pichia* are exemplary yeast hosts, with suitable vectors having expression control sequences (e.g., promoters), an origin of replication, termination sequences, and the like as desired. Typical promoters include 3-phosphoglycerate kinase and other glycolytic enzymes. Inducible yeast promoters include, among others, promoters from alcohol dehydrogenase, isocytochrome C, and enzymes responsible for methanol, maltose, and galactose utilization.

Mammalian cells in culture may also be used as host cells for expressing the antibodies, antigen-binding fragments or the fusion proteins disclosed herein. Examples of suitable host cell lines capable of secreting heterologous proteins (e.g., intact immunoglobulins) which are well known in the art, include CHO cell lines, various COS cell lines, HeLa cells, 293 cells, myeloma cell lines, transformed B-cells, and hybridomas. Expression vectors for these cells can include expression control sequences, such as an origin of replication, a promoter, an enhancer and necessary processing information sites such as ribosome binding site, RNA splice site and/or transcriptional terminator sequences. Examples of expression control sequences include SV40, adenovirus, bovine papilloma virus, cytomegalovirus and the like.

The anti-Mtb AM antibodies, or Mtb AM-binding fragments thereof, disclosed herein can be expressed using a single expression construct or vector or multiple expression constructs or vectors (e.g., two or three expression constructs). When the antibody heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms disclosed herein can be purified according to standard procedures of the art, including ammonium sulfate precipitation, affinity columns, column chromatography, HPLC purification, gel electrophoresis, and the like (see generally Scopes, Protein Purification (Springer-Verlag, N.Y., (1982)). Substantially pure immunoglobulins of at least about 90 to 95% homogeneity are preferred, and 98 to 99% or more homogeneity most preferred, for pharmaceutical uses.

The anti-Mtb AM antibodies, or Mtb AM-binding fragments thereof, disclosed herein can be made by any method known in the art.

In an embodiment, a pharmaceutical composition is provided comprising an anti-Mtb AM antibody, or Mtb AM-binding fragment thereof as described herein.

In an embodiment, a pharmaceutical composition comprising an anti-Mtb AM antibody, or Mtb AM-binding fragment thereof, described herein, and a pharmaceutically acceptable excipient, is provided. The pharmaceutically acceptable excipient can be a pharmaceutically-acceptable material, composition or vehicle, such as a liquid or solid filler, diluent, manufacturing aid (e.g., lubricant, talc magnesium, calcium or zinc stearate, or steric acid), solvent or encapsulating material, involved in carrying or transporting the therapeutic compound for administration to the subject, bulking agent, salt, surfactant and/or a preservative. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations.

Compositions or pharmaceutical compositions comprising the anti-Mtb AM antibody, or Mtb AM-binding fragment thereof, disclosed herein comprise stabilizers to prevent loss of activity or structural integrity of the protein due to the effects of denaturation, oxidation, or aggregation over a period of time during storage and transportation prior to use. The compositions or pharmaceutical compositions can comprise one or more of any combination of salts, surfactants, pH and tonicity agents such as sugars that contribute to overcoming aggregation problems. Where a composition or pharmaceutical composition disclosed herein is used as an injection, the composition may have a pH value in an approximately neutral pH range. In some embodiments, surfactant levels are minimized to avoid bubbles in the formulation which are detrimental for injection into subjects. In an embodiment, the composition or pharmaceutical composition is in liquid form and stably supports high concentrations of bioactive antibody in solution and is suitable for inhalational or parenteral administration. In an embodiment, the composition or pharmaceutical composition is suitable for intravenous, intramuscular, intraperitoneal, intradermal and/or subcutaneous injection. In an embodiment, the composition or pharmaceutical composition is in liquid form and has minimized risk of bubble formation and a naphylactoid side effects. In an embodiment, the composition or pharmaceutical composition is isotonic. In an embodiment, the composition or pharmaceutical composition has a pH or 6.8 to 7.4.

In one embodiment, the anti-Mtb AM antibody, or Mtb AM-binding fragment thereof, disclosed herein is lyophilized and/or freeze dried and is reconstituted for use.

The antibodies, or fragments of antibodies, or compositions, or pharmaceutical compositions described herein can also be lyophilized or provided in any suitable forms including, but not limited to, injectable solutions or inhalable solutions, gel forms, and tablet forms.

Provided herein is a method of reducing the activity of Mtb AM in a subject in need thereof, the method comprising administering to said subject a therapeutically effective amount of (1) an anti-Mtb AM antibody, or Mtb AM-binding fragment thereof, disclosed herein or (2) a pharmaceutical composition comprising an anti-Mtb AM antibody, or Mtb AM-binding fragment thereof, disclosed herein. Provided herein is (1) an anti-Mtb AM antibody, or Mtb AM-binding fragment thereof, disclosed herein or (2) a pharmaceutical composition comprising an anti-Mtb AM antibody, or Mtb AM-binding fragment thereof, for use in reducing the activity of Mtb AM in a subject in need thereof. Provided herein is the use of an anti-Mtb AM antibody, or Mtb AM-binding fragment thereof, disclosed herein in the manufacture of a medicament for reducing the activity of Mtb AM in a subject in need thereof.

Provided herein is a method of treating a *Mycobacterium tuberculosis* infection in a subject in need thereof, the method comprising administering to said subject a therapeutically effective amount of (1) an anti-Mtb AM antibody, or Mtb AM-binding fragment thereof, disclosed herein or (2) a pharmaceutical composition comprising an anti-Mtb AM antibody, or Mtb AM-binding fragment thereof, disclosed herein. Provided herein is (1) an anti-Mtb AM antibody, or Mtb AM-binding fragment thereof, disclosed herein or (2) a pharmaceutical composition comprising an anti-Mtb AM antibody, or Mtb AM-binding fragment thereof, for use in treating a *Mycobacterium tuberculosis* infection in a subject in need thereof. Provided herein is the use of an anti-Mtb AM antibody, or Mtb AM-binding fragment thereof, disclosed herein in the manufacture of a medicament for treating a *Mycobacterium tuberculosis* infection in a subject in need thereof.

In an embodiment, the disclosure provides a method of reducing the likelihood of a *Mycobacterium tuberculosis* infection in a subject in need thereof, the method comprising administering to the subject who does not have a *Mycobacterium tuberculosis* infection a prophylactically effective amount of (1) an anti-Mtb AM antibody, or Mtb AM-binding fragment thereof, disclosed herein or (2) a pharmaceutical composition comprising an anti-Mtb AM antibody, or Mtb AM-binding fragment thereof, disclosed herein. Provided herein is (1) an anti-Mtb AM antibody, or Mtb AM-binding fragment thereof, disclosed herein or (2) a pharmaceutical composition comprising an anti-Mtb AM antibody, or Mtb AM-binding fragment thereof, for use in reducing the likelihood of a *Mycobacterium tuberculosis* infection in a subject in need thereof. Provided herein is the use of an anti-Mtb AM antibody, or Mtb AM-binding fragment thereof, disclosed herein in the manufacture of a medicament for reducing the likelihood of a *Mycobacterium tuberculosis* infection in a subject in need thereof.

In an embodiment, the disclosure provides a method of treating a disease, disorder, or condition mediated by, or related to increased activity of *Mycobacterium tuberculosis* in a subject in need thereof, the method comprising administering to said subject a therapeutically effective amount of (1) an anti-Mtb AM antibody, or Mtb AM-binding fragment thereof, disclosed herein or (2) a pharmaceutical composition comprising an anti-Mtb AM antibody, or Mtb AM-binding fragment thereof, disclosed herein. Provided herein is (1) an anti-Mtb AM antibody, or Mtb AM-binding fragment thereof, disclosed herein or (2) a pharmaceutical composition comprising an anti-Mtb AM antibody, or Mtb AM-binding fragment thereof, for use in treating a disease, disorder, or condition mediated by, or related to increased activity of *Mycobacterium tuberculosis* in a subject in need thereof. Provided herein is the use of an anti-Mtb AM antibody, or Mtb AM-binding fragment thereof, disclosed herein in the manufacture of a medicament for treating a disease, disorder, or condition mediated by, or related to increased activity of *Mycobacterium tuberculosis* in a subject in need thereof.

In embodiments, the "subject" is a mammal. In embodiment, the subject is a non-primate (e.g., cows, pigs, horses, cats, dogs, rats, mouse, etc.) or a primate (e.g., monkey and human). Individuals and patients are also subjects herein.

The anti-Mtb AM antibodies, or Mtb AM-binding fragments thereof, disclosed herein can be administered with to one or more additional therapeutic agents. Suitable additional therapeutic agents in this regard include, but are not limited to, drugs, toxins, and derivatives thereof. Non-limiting examples of additional therapeutic agents include isoniazid, rifampin, ethambutol, pyrazinamide, bedaquiline, linezolid, and pretomanid.

In an embodiment, an assay device is provided for selectively detecting a one or more bacteria from the MTC group in a biological sample comprising: a first portion comprising a first plurality of anti-Mtb AM antibodies, or Mtb AM-binding fragments thereof, as described herein, or anti-mycobacterial AM-antibodies, wherein the antibodies or fragments are each attached to their own reporting entity; and a second portion comprising a second plurality of anti-Mtb AM antibodies, or Mtb AM-binding fragments thereof, as described herein, or anti-mycobacterial AM-antibodies.

In an embodiment, an assay device is provided for selectively detecting AM and/or LAM in a biological sample comprising: a first portion comprising a first plurality of anti-Mtb AM antibodies, or Mtb AM-binding fragments thereof, as described herein, or anti-mycobacterial AM-antibodies, wherein the antibodies or fragments are each attached to their own reporting entity; and a second portion comprising a second plurality of anti-Mtb AM antibodies, or Mtb AM-binding fragments thereof, as described herein, or anti-mycobacterial AM-antibodies.

In an embodiment, an assay device is provided for selectively detecting AM and/or LAM from MTC in a biological sample comprising: a first portion comprising a first plurality of anti-Mtb AM antibodies, or Mtb AM-binding fragments thereof, as described herein, or anti-mycobacterial AM-antibodies, wherein the antibodies or fragments are each attached to their own reporting entity; and a second portion comprising a second plurality of anti-Mtb AM antibodies, or Mtb AM-binding fragments thereof, as described herein, or anti-mycobacterial AM-antibodies.

MTC is a genetically related group of *Mycobacterium* species that can cause tuberculosis in humans or other animals and includes *Mycobacterium tuberculosis, M. africanum, M. canettii, M. bovis, M. microti, M. orygis, M. caprae, M. pinnipedii, M. suricattae*, and *M. mungi.*

In an embodiment, the reporting entity comprises an enzyme. In an embodiment, the enzyme is horseradish peroxidase (HRP) or alkaline phosphatase (AP).

In one embodiment, the reporting entity comprises a gold nanoparticle.

In embodiments, the second plurality of anti-Mtb AM-antibodies, or Mtb AM-binding fragments thereof, or anti-mycobacterial AM-antibodies, is affixed to a solid support of the device.

In embodiments, the first plurality of anti-Mtb AM-antibodies, or Mtb AM-binding fragments thereof, or anti-mycobacterial AM-antibodies, is not affixed to a solid support of the device.

In embodiments, the solid support comprises nitrocellulose.

In embodiments, the device further comprises a fluid sample pad prior in sequential order to the first and second portions.

In embodiments, the device further comprises a control portion subsequent in sequential order to the first and second portions.

In embodiments, the control portion comprises a third plurality of antibodies, immobilized on a solid support of the device, and which third plurality of antibodies are capable of binding the first plurality of anti-Mtb AM-antibodies, or Mtb AM-binding fragments thereof, or anti-mycobacterial AM-antibodies each attached to their own reporting molecule.

In embodiments, the device further comprises a fluid-absorbent wicking pad subsequent in sequential order to the first and second portions, and third portion if present.

In embodiments, the second plurality of anti-Mtb AM-antibodies, or Mtb AM-binding fragments thereof, as described herein, or anti-mycobacterial AM-antibodies.

Provided is a lateral flow assay device for detecting a *Mycobacterium tuberculosis* in a biological sample comprising:

(a) a first portion comprising a first plurality of anti-Mtb AM-antibodies, or Mtb AM-binding fragments thereof, as disclosed herein, wherein the antibodies or fragments are each attached to their own reporting entity; and (b) a second plurality of anti-Mtb AM-antibodies, or Mtb AM-binding fragments thereof, or anti-mycobacterial AM-antibodies.

Provided is a lateral flow assay device for detecting AM and/or LAM in a biological sample comprising:

(a) a first portion comprising a first plurality of anti-Mtb AM-antibodies, or Mtb AM-binding fragments thereof, as disclosed herein, wherein the antibodies or fragments are each attached to their own reporting entity; and (b) a second plurality of anti-Mtb AM-antibodies, or Mtb AM-binding fragments thereof, or anti-mycobacterial AM-antibodies.

In some embodiments, the first plurality of anti-Mtb AM antibodies, or Mtb AM-binding fragments thereof, comprises anti-Mtb AM antibodies, or Mtb AM-binding fragments thereof, comprising a heavy chain variable region and a light chain variable region, wherein the heavy chain and the light chain variable regions comprise a CDR1, CDR2, and CDR3; and wherein CDR1H comprises SEQ ID NO:1, CDR2H comprises SEQ ID NO:2, CDR3H comprises SEQ ID NO:3, CDR1L comprises SEQ ID NO:4, CDR2L comprises SEQ ID NO:5, and CDR3L comprises SEQ ID NO:6, In some embodiment, the first plurality of anti-Mtb AM-antibodies, or Mtb AM-binding fragments thereof, comprises anti-Mtb AM-antibodies, or Mtb AM-binding fragments thereof, comprising a heavy variable region comprising SEQ ID NO:7 and a light variable region comprising SEQ ID NO:8. In some embodiments, the first plurality of anti-Mtb AM antibodies, or Mtb AM-binding fragments thereof, comprises anti-Mtb AM antibodies, or Mtb AM-binding fragments thereof, comprising a heavy chain variable region and a light chain variable region, wherein the heavy chain and the light chain variable regions comprise a CDR1, CDR2, and CDR3; and wherein CDR1H comprises SEQ ID NO:26, CDR2H comprises SEQ ID NO:27, CDR3H comprises SEQ ID NO:28, CDR1L comprises SEQ ID NO:29, CDR2L comprises SEQ ID NO:30, and CDR3L comprises SEQ ID NO:31. In some embodiment, the first plurality of anti-Mtb AM-antibodies, or Mtb AM-binding fragments thereof, comprises anti-Mtb AM-antibodies, or Mtb AM-binding fragments thereof, comprising a heavy variable region comprising SEQ ID NO:32 and a light variable region comprising SEQ ID NO:34.

In some embodiments, the second plurality of anti-Mtb AM antibodies, or Mtb AM-binding fragments thereof, comprises anti-Mtb AM antibodies, or Mtb AM-binding fragments thereof, comprising a heavy chain variable region and a light chain variable region, wherein the heavy chain and the light chain variable regions comprise a CDR1, CDR2, and CDR3; and wherein CDR1H comprises SEQ ID NO:17, CDR2H comprises SEQ ID NO:18, CDR3H comprises SEQ ID NO:19, CDR1L comprises SEQ ID NO:20, CDR2L comprises SEQ ID NO:21, and CDR3L comprises SEQ ID NO:22. In some embodiments, the second plurality of anti-Mtb AM antibodies, or Mtb AM-binding fragments thereof, comprises anti-Mtb AM antibodies, or Mtb AM-binding fragments thereof, comprising a heavy chain variable region and a light chain variable region, wherein the heavy chain variable regions comprises a sequence comprising SEQ ID NO: 23 or SEQ ID NO: 24, and wherein the light chain variable region comprises a sequence comprising SEQ ID NO: 25.

In some embodiments, the assay device comprises one or more pluralities of anti-Mtb AM antibodies, or Mtb AM-binding fragments thereof, or anti-mycobacterial AM-antibodies, wherein at least one of the pluralities of anti-Mtb AM antibodies, or Mtb AM-binding fragments thereof, or anti-mycobacterial AM-antibodies, comprises a non-human constant region or a modified non-human constant region. In some embodiments, the assay device comprises one or more pluralities of anti-Mtb AM antibodies, or Mtb AM-binding fragments thereof, or anti-mycobacterial AM-antibodies, wherein at least one of the pluralities of anti-Mtb AM antibodies, or Mtb AM-binding fragments thereof, or anti-mycobacterial AM-antibodies, comprises a murine constant region or a modified murine constant region.

In an embodiment, the reporting entity comprises an enzyme. In an embodiment, the enzyme is horseradish peroxidase (HRP) or alkaline phosphatase (AP). In an embodiment, the reporting entity comprises a gold nanoparticle.

In an embodiment, the second plurality of anti-Mtb AM antibodies, or Mtb AM-binding fragments thereof, or anti-mycobacterial AM-antibodies is affixed to a solid support of the device.

In an embodiment, the first plurality of anti-Mtb AM antibodies, or Mtb AM-binding fragments thereof, or anti-mycobacterial AM-antibodies is not affixed to a solid support of the device.

In an embodiment, the solid support comprises nitrocellulose.

In an embodiment, the device further comprises a fluid sample pad prior in sequential order to the first and second portions.

In an embodiment, the device further comprises a control portion subsequent in sequential order to the first and second portions.

In an embodiment, the control portion comprises a third plurality of antibodies, immobilized on a solid support of the device, and which third plurality of antibodies are capable of binding the first plurality of anti-Mtb AM antibodies, or Mtb AM-binding fragments thereof, or anti-mycobacterial AM-antibodies, each attached to their own reporting molecule.

In an embodiment, the device further comprises a fluid-absorbent wicking pad subsequent in sequential order to the first and second portions, and third portion if present.

In embodiments, the second plurality of anti-Mtb AM antibodies, or Mtb AM-binding fragments thereof, comprises anti-Mtb AM antibodies, or Mtb AM-binding fragments thereof, described herein.

Provided herein is an assay device for selectively detecting one or more bacteria from the MTC group in a biological sample comprising:

(a) a first portion comprising a first plurality of anti-Mtb AM antibodies, or Mtb AM-binding fragments thereof, wherein the anti-Mtb AM antibodies, or Mtb AM-binding fragments thereof, are attached to a reporting entity and wherein anti-Mtb AM antibodies, or Mtb AM-binding fragments thereof, comprise a heavy chain variable region and a light chain variable region, wherein the heavy chain and the light chain variable regions comprises a CDR1, CDR2, and CDR3; and wherein CDR1H comprises SEQ ID NO:17, CDR2H comprises SEQ ID NO:18, CDR3H comprises SEQ ID NO:19. CDR1L comprises SEQ ID NO:20, CDR2L comprises SEQ ID NO:21, and CDR3L comprises SEQ ID NO:22; and (b) a second portion comprising a second plurality of anti-Mtb AM antibodies, or Mtb AM-binding fragments thereof, disclosed herein.

Provided herein is an assay device for selectively detecting one or more bacteria from the MTC group in a biological sample comprising:

(a) a first portion comprising a first plurality of anti-Mtb AM antibodies, or Mtb AM-binding fragments thereof, wherein the anti-Mtb AM antibodies, or Mtb AM-binding fragments thereof, are attached to a reporting entity and wherein anti-Mtb AM antibodies, or Mtb AM-binding fragments thereof, comprise a heavy chain variable region and a light chain variable region, wherein the heavy chain and the light chain variable regions comprises a CDR1, CDR2, and CDR3; and wherein CDR1H comprises SEQ ID NO:1, CDR2H comprises SEQ ID NO:2, CDR3H comprises SEQ ID NO:3, CDR1L comprises SEQ ID NO:4, CDR2L comprises SEQ ID NO:5, and CDR3L comprises SEQ ID NO:6; and (b) a second portion comprising a second plurality of anti-Mtb AM antibodies, or Mtb AM-binding fragments thereof, disclosed herein.

Provided herein is an assay device for selectively detecting one or more bacteria from the MTC group in a biological sample comprising:

(a) a first portion comprising a first plurality of anti-Mtb AM antibodies, or Mtb AM-binding fragments thereof, wherein the anti-Mtb AM antibodies, or Mtb AM-binding fragments thereof, are attached to a reporting entity and wherein anti-Mtb AM antibodies, or Mtb AM-binding fragments thereof, comprise a heavy chain variable region and a light chain variable region, wherein the heavy chain and the light chain variable regions comprises a CDR1, CDR2, and CDR3; and wherein CDR1H comprises SEQ ID NO:26, CDR2H comprises SEQ ID NO:27, CDR3H comprises SEQ ID NO:28, CDR1L comprises SEQ ID NO:29, CDR2L comprises SEQ ID NO:30, and CDR3L comprises SEQ ID NO:31; and (b) a second portion comprising a second plurality of anti-Mtb AM antibodies, or Mtb AM-binding fragments thereof, disclosed herein.

Provided herein is an assay device for selectively detecting AM or LAM from the MTC group in a biological sample comprising:

(a) a first portion comprising a first plurality of anti-Mtb AM antibodies, or Mtb AM-binding fragments thereof, wherein the anti-Mtb AM antibodies, or Mtb AM-binding fragments thereof, are attached to a reporting entity and wherein anti-Mtb AM antibodies, or Mtb AM-binding fragments thereof, comprise a heavy chain variable region and a light chain variable region, wherein the heavy chain and the light chain variable regions comprises a CDR1, CDR2, and CDR3; and wherein CDR1H comprises SEQ ID NO:17, CDR2H comprises SEQ ID NO:18, CDR3H comprises SEQ ID NO:19, CDR1L comprises SEQ ID NO:20, CDR2L comprises SEQ ID NO:21, and CDR3L comprises SEQ ID NO:22; and (b) a second portion comprising a second plurality of anti-Mtb AM antibodies, or Mtb AM-binding fragments thereof, disclosed herein.

Provided herein is an assay device for selectively detecting AM or LAM from the MTC group in a biological sample comprising:

(a) a first portion comprising a first plurality of anti-Mtb AM antibodies, or Mtb AM-binding fragments thereof, wherein the anti-Mtb AM antibodies, or Mtb AM-binding fragments thereof, are attached to a reporting entity and wherein anti-Mtb AM antibodies, or Mtb AM-binding fragments thereof, comprise a heavy chain variable region and a light chain variable region, wherein the heavy chain and the light chain variable regions comprises a CDR1, CDR2, and CDR3; and wherein CDR1H comprises SEQ ID NO:1, CDR2H comprises SEQ ID NO:2, CDR3H comprises SEQ ID NO:3, CDR1L comprises SEQ ID NO:4, CDR2L comprises SEQ ID NO:5, and CDR3L comprises SEQ ID NO:6; and (b) a second portion comprising a second plurality of anti-Mtb AM antibodies, or Mtb AM-binding fragments thereof, disclosed herein.

Provided herein is an assay device for selectively detecting AM or LAM from the MTC group in a biological sample comprising:

(a) a first portion comprising a first plurality of anti-Mtb AM antibodies, or Mtb AM-binding fragments thereof, wherein the anti-Mtb AM antibodies, or Mtb AM-binding fragments thereof, are attached to a reporting entity and wherein anti-Mtb AM antibodies, or Mtb AM-binding fragments thereof, comprise a heavy chain variable region and a light chain variable region, wherein the heavy chain and the light chain variable regions comprises a CDR1, CDR2, and CDR3; and wherein CDR1H comprises SEQ ID NO:26, CDR2H comprises SEQ ID NO:27, CDR3H comprises SEQ ID NO:28. CDR1L comprises SEQ ID NO:29, CDR2L comprises SEQ ID NO:30, and CDR3L comprises SEQ ID NO:31; and (b) a second portion comprising a second plurality of anti-Mtb AM antibodies, or Mtb AM-binding fragments thereof, disclosed herein.

In an embodiment, a method is provided for detecting one or more bacteria from the MTC group in a biological sample comprising:

(a) contacting the device described herein with the sample; and (b) observing if one or more bacteria from the MTC group bind to the second plurality of anti-Mtb AM antibodies, or Mtb AM-binding fragments thereof, or anti-mycobacterial AM-antibodies, wherein if such anti-Mtb AM antibodies, or Mtb AM-binding fragments thereof, or anti-mycobacterial AM-antibodies, bind, then one or more bacteria from the MTC group have been detected in the biological sample; and if no anti-Mtb AM antibodies, or Mtb AM-binding fragments thereof, or anti-mycobacterial AM-antibodies, bind to the second plurality of anti-Mtb AM antibodies, or Mtb AM-binding fragments thereof, or anti-mycobacterial AM-antibodies, then bacteria from the MTC group have not been detected in the biological sample.

Many available anti-Mtb AM antibodies react with mycobacterial strains from both the MTC group and non-tuberculous mycobacteria (NTM). In embodiments, provided herein are antibodies and antigen-binding fragments thereof that bind to MTC and show significantly decreased or no binding to NTM. Accordingly, provided is a method of discriminating between one or more bacteria from the MTC group and NTM using anti-Mtb AM antibodies, or Mtb AM-binding fragments thereof, or anti-mycobacterial AM-antibodies, including anti-Mtb AM antibodies, or Mtb AM-binding fragments thereof, disclosed herein. Diagnostic tests based on such methods that are able to discriminate between virulent and non-virulent *Mycobacterium* infections, or one or more bacteria from the MTC group and NTM, represent a major advance that will greatly reduce wasted effort and consequent costs resulting from further diagnostic tests and/or therapeutic procedures.

In one embodiment, provided is a method of detecting and/or distinguishing one or more bacteria from the MTC group and NTM in a biological sample, the method comprising:

(a) providing a biological sample comprising an Mtb antigen;

(b) contacting the sample with a first anti-Mtb AM antibody, or Mtb AM-binding fragment thereof, or anti-mycobacterial AM-antibody, wherein the first anti-Mtb AM antibody, or Mtb AM-binding fragment thereof, or anti-mycobacterial AM-antibody, binds one or more bacteria from the MTC group, but does not substantially bind to NTM;

(c) observing if the Mtb antigen in the biological sample binds to the first anti-Mtb AM antibody, or Mtb AM-binding fragment thereof, or anti-mycobacterial AM-antibody;

(d) contacting the sample with a second anti-Mtb antibody, or Mtb-binding fragment thereof, or anti-mycobacterial AM-antibody, wherein the second anti-Mtb AM antibody, or Mtb AM-binding fragment thereof or anti-mycobacterial AM-antibody binds to one or more bacteria from the MTC group and to NTM;

(e) observing if the Mtb antigen in the biological sample binds to the second anti-Mtb AM antibody, or Mtb AM-binding fragment thereof, or anti-mycobacterial AM-antibody; wherein if the Mtb antigen in the biological sample binds to the first and the second anti-Mtb AM antibodies, or Mtb AM-binding fragments thereof, or anti-mycobacterial AM-antibody, then one or more bacteria from the MTC group have been detected in the biological sample; and wherein if the Mtb antigen in the biological sample binds to the second, but not the first anti-Mtb AM antibody, or Mtb AM-binding fragment thereof, or anti-mycobacterial AM-antibody, then NTM has been detected in the biological sample.

In embodiments, the method further comprises obtaining the sample from a subject.

In embodiments, the sample is blood, blood plasma, blood serum, cerebrospinal fluid, bile acid, saliva, synovial fluid, pleural fluid, pericardial fluid, peritoneal fluid, feces, nasal fluid, ocular fluid, intracellular fluid, intercellular fluid, lymph fluid, urine, tissue, sputum, bladder washings, oral washings, tissue samples, touch preps, or fine-needle aspirates. The biological sample can be concentrated prior to use.

In embodiments, the subject is human. In some embodiment, the subject is a non-human mammal. In some embodiments, the subject is a cow, buffalo, lion. In some embodiment, the subject is an animal suitable for use in research, including, but not limited to, mouse, rat, rabbit, guinea pig, sheep, goat, and nonhuman primate. In some embodiments, the antibodies and antigen-binding fragments thereof disclosed herein bind to one or more strains of the MTC group, which comprises *Mycobacterium tuberculosis, M. africanum, M. canettii, M. bovis, M. microti, M. orygis, M. caprae, M. pinnipedii, M. suricattae*, and *M. mungi*. In some embodiments, the antibodies and antigen-binding fragments thereof disclosed herein bind to *M. bovis*.

"And/or" as used herein, for example, with option A and/or option B, encompasses the separate embodiments of (i) option A, (ii) option B, and (iii) option A plus option B.

All combinations of the various elements described herein are within the scope of the disclosure unless otherwise indicated herein or otherwise clearly contradicted by context.

All references cited herein are incorporated herein in their entireties.

The following non-limiting example serves to further illustrate embodiments of the disclosure.

EXAMPLES

Material and Methods for the Examples Below

Donor Information

Sera and peripheral blood mononuclear cells (PBMC) were collected from subjects enrolled in a cross-sectional TB immunodiagnostic study approved from the institution review board of the Albert Einstein College of Medicine (AECOM). All study subjects gave written informed consent prior to their enrollment.

Culturing of Mycobacteria and Generation of Mycobacterial Capsular Arabinomannan (AM)

Various strains of the *Mycobacterium tuberculosis* (Mtb) complex group comprised of laboratory strains (H37Rv, H37Ra, Erdman), clinical strains (CDC1551, Beijing) and the TB vaccine strain *M. bovis Bacillus* Calmette-Guerin (BCG) were pre-cultured in Middlebrook 7H9 broth supplemented with 0.05% (v/v) tyloxapol and 10% (v/v) oleic albumin dextrose catalase enrichment to reach stationary growth phase (OD600 of 0.5-1.0). Similarly, non-tuberculous mycobacterial strains (M abscesses and *M. avium*) were cultured. To allow for mycobacterial capsule formation, the pre-culture strains were inoculated in minimal medium without detergent at 37° C. for 3 weeks. Capsular polysaccharides were isolated by physical disruption of cells using glass beads, followed by clarification, and lyophylization. AM was separated from the other capsular components using chloroform:methanol:water extraction (1:1:0.9) and was isolated and purified as previously described. Collected fractions were assayed for carbohydrate content by the phenol-sulfuric acid assay. AM-positive fractions were tested using a standard ELISA and positive control antibody (murine mAb CS-35, BEI NR-13811). The concentrations of AM and LAM were confirmed by GC-MS calculating the ratio of arabinose to mannose.

Isolation of AM-Specific B Cells

To identify arabinomannan (AM)-positive B cells by standard B cell immunophenotyping and fluorescence activated cell sorting (FACS), AM was activated by 1-cyano-4-dimethylaminopyridinium tetrafluoroborat (CDAP) and conjugated to biotin (1:20). The AM-probe was then used with the antibody cocktail for cell staining. Lymphocytes were first identified, then live B-cells were further enriched based on $CD19^+$ $CD27^+$. Secondary staining using streptavidin labeled with phycoerythrin (PE) was used to detect the AM-positive population. Fluorescence minus one (FMO) controls were used to set the sorting gates for double positive ($AM^+$, $IgG^+$) B cells. Double positive cells were sorted into a 96-well plate into RNAse-inhibiting lysis buffer.

Recombinant Generation of mAbs from Isolated Single B Cells

Reverse transcription PCR (RT-PCR) of lysed single B cells was used to synthesize complementary DNA (cDNA). Immunoglobulin genes for the heavy and light chains of the variable (V) region (Ig VH VK and $V_L$) were amplified using random hexamer primers and sequenced. Then nested PCR was used to clone Ig genes into IgG heavy- and light-chain expression vectors and co-expressed by transfection of 293 HEK cells.

Bio Laver Interferometry

Initially, binding of the anti-AM mAbs to the biotinylated probe was tested with the OctetRed™ system (ForteBio, Pall LLC). Briefly, biotinylated AM was loaded on to streptavidin biosensor tips at 0.5 μg/ml. The loaded antigen was dipped into serially diluted mAb. Binding curves were generated and used to calculate dissociation constants. To estimate values for the $k_{on}$ (association rate constant), $k_{off}$ (dissociation rate constant), and $K_D$ (equilibrium dissociation constant), a global data fitting 2:1 binding model was used. The 2:1 heterogenous ligand model assumes analyte binding at two independent ligand sites. Each ligand site binds the analyte independently and with a different rate constant. Epitope binning is a term used to describe segmentation of a panel of monoclonal antibodies (mAbs) into bins based upon the antigen region, or epitope, bound by each antibody. This grouping is performed using cross competition assays, in which the competitive binding of antibody pairs to a specific antigen is characterized. For epitope binning experiments, a double-phase binding set-up was used; the antigen was first immobilized on a streptavidin sensor and then allowed to equilibrate in a solution containing the first mAb. The sensor was then transferred to a second solution containing the second mAb. Briefly, after AM is loaded on the biosensor tip, it is incubated with the first mAb and an association curve is observed. After the binding plateaus, the biosensor is dipped into another well containing the competitor mAb or isotype matched control mAb. The observation of a second association curve suggests that there are available binding sites on AM to the competitor mAb, but not the mAb itself.

Antibody Binding Assays

ELISA experiments were used to determine binding and estimate affinity of mAbs to isolated capsular AM, cell wall LAM, as well whole cells from different mycobacteria strains. Immunofluorescence microcopy was used to visualize the binding of mAbs to fixed Mtb with an intact capsule. Mtb was cultured in conditions to preserve the capsule and was fixed with 2% PFA before use. Poly-L-lysine slides were coated with the fixed Mtb. MAbs were incubated at 10 μg/ml for screening. Then, human mAbs were detected with tetramethylrhodamine (TRITC)-labeled goat-anti human IgG and viewed with a Zeiss observer microscope.

Synthetic AM Glycan Microarray

A novel glycan microarray comprised of 63 synthetically generated AM oligosaccharide fragments was used to determine mAb reactivity to glycan epitopes. This protocol was previously described for polyclonal sera binding and was adapted for mAb binding characterization. Briefly, microarray slides were blocked with 3% BSA in PBS at 4 C overnight, then mAbs were incubated at 5 μg/ml for 4 hrs at 37° C. After washing with PBST, the slides were first incubated with goat anti-human biotin-labeled IgG (Southern Biotech, AL) and then followed with a streptavidin probe tagged with SureLight® P3 Cy5 (Cayman Chemicals, MI) at 37° C. for 2 hrs. The GenePix 4000 Microarray scanner system (Molecular Devices, CA) was used for scanning. Images were analyzed by using GenePix Pro 7.3.0.0 to measure median pixel intensity (MPI) and neighboring background pixel intensity (BPI) of individual spots. The median fluorescence intensity (MFI), representing AM-epitope specific mAb reactivity, was calculated using the MPI minus the BPI and averaged from the triplicate spots. The median fluorescent intensity (MFI), representing AM-epitope specific mAb reactivity, was the MPI minus the BPI. The final MFI was averaged from the triplicates.

Urinary LAM Sandwich ELISA mAbs were tested for their use as capture or detection antibodies in the urinary LAM capture sandwich ELISA. The pair of anti-LAM mAbs CS-35 (murine) and A194 (human) were used as a positive control to assess capture and detection of serially diluted LAM in urine. Capture antibodies (CS-35 and L1AM04) were used at 10 μg/mL in PBS and incubated at 4° C. overnight. Urine was spiked with known amounts of LAM and incubated with the capture antibody at 4° C. overnight. Following overnight incubation, the plate was brought to room temperature and blocked for 1 hr. After blocking, the plates were vigorously washed with the wash buffer (200 μL×10) and were incubated for 2 hr at room temperature with the biotinylated detection antibodies (A194 or T1AM09) at a final concentration of 250 ng/mL in wash buffer. Following a second wash, 100 μL of 1:200 dilution of Streptavidin-Horseradish Peroxidase (HRP) was added to the plates and incubated as per the kit protocol. After the final wash, 100 μL Ultra TMB-ELISA chromogenic substrate was added to the plates and incubated for 30 min. The reaction was stopped by addition of sulphuric acid and the optical density was read at 450 nm.

Example 1: Generation of Antibody L1AM04

Monoclonal mAbs were generated using a targeted, flow cytometry-based strategy. Initially, subjects from a range of Mtb exposure and infection along the clinical spectrum were tested for their serum anti-AM IgG responses. Donor L1 was selected for B cell sorting and antibody generation based on having available PBMCs and anti-AM IgG titers.

Donor L1 was an asymptomatic healthcare provider, tuberculin skin test positive (>15 mm), whole blood interferon-gamma release assay (IGRA; Quantiferon TB Gold) positive.

Analysis of serial sera obtained from subject L over a period of seven years revealed persistently detectable high anti-AM IgG titers. Using PBMCs isolated from L1, AM-positive, IgG-positive memory B cells were sorted. Of the around 300 AM-positive B-cells (CD19+, CD27+), around 80 were $IgG^+$ and sorted into individual wells. The variable heavy and light chains of the B cell receptors were recovered by nested RT-PCR and an initial panel of recombinant human mAbs were expressed in an IgG1 vector in HEK293 cells. RT-PCR sequences revealed that mAbs came from distinct germline lineages. From the about 80 AM-positive, IgG-positive B-cells, eight expressed adequate quantities of protein.

The CDR and variable chain sequences of L1AM04 are provided in Tables 2 and 3.

TABLE 2

CDR sequences of antibody L1AM04.

| CDR | Kabat numbering SEQ ID NO: | Kabat numbering Amino acid sequence | IMGT numbering SEQ ID NO: | IMGT numbering Amino acid sequence |
|---|---|---|---|---|
| CDRH1 | 1 | SYAMS | 11 | GFTFASYA |
| CDRH2 | 2 | TLSDSGGATHYAD SVQG | 12 | LSDSGGAT |
| CDRH3 | 3 | DVPPKTAGPMFDY | 13 | ARDVPPKTAGPMFDYW |
| CRDL1 | 4 | RSSESLVHSNGNTYLS | 14 | ESLVHSNGNTY |
| CDRL2 | 5 | EISKRYSG | 15 | EIXXXXXXS Wherein X can be any amino acid |
| CDRL3 | 6 | AQVSHFPRT | 16 | AQVSHFP |

TABLE 3

Heavy and light variable chains sequences of LIAM04. CDRs are indicated (Kabat numbering).

| Sequence | SEQ ID NO: | Sequence |
|---|---|---|
| VH | 7 | EVQLLESGGGLVQPGGSQRLFCEASGFTFA**SYAMS**WVRLAPGKG LEWVS**TLSDSGGATHYADSVQG**RFTISRDNSNNVVYLQMNSLR AEDTAVYYCAR**DVPPKTAGPMFDY**WGLGTLVTVSS |
| VH | 9 | GAGGTGCAGCTGTTGGAGTCTGGGGGAGGCTTGGTACAGCCTG GGGGGTCCCAGAGACTCTTCTGTGAAGCCTCTGGATTCACCTTT GCCAGCTATGCCATGAGTTGGGTCCGCCTGGCCCCAGGGAAGG GGCTGGAGTGGGTCTCAACTCTTAGTGATAGTGGTGGTGCCAC ACACTACGCGGACTCCGTGCAGGGCCGGTTCACCATCTCCAGA GACAATTCCAACAATGTGGTGTATTTGCAAATGAACAGCCTGA GAGCCGAGGACACGGCCGTTTATTATTGTGCGAGAGATGTCCC CCCCAAGACGGCAGGCCCCATGTTTGACTACTGGGGCCTGGGA ACCCTGGTCACCGTCTCCTCA |
| VL (kappa) | 8 | DIVMTQTPLSSPVSLGQPASISC**RSSESLVHSNGNTYLS**WLHQRPG QPPRLLIY**EISKRYSG**VSDRFSGSGAGTDFTLKISRVEAEDVGIYFC **AQVSHFPRT**FGQGTKVEIK |
| VL (kappa) | 10 | GATATTGTGATGACCCAGACTCCACTCTCTTCCCCTGTCAGCCT TGGACAGCCGGCCTCCATCTCCTGCAGGTCGAGTGAAAGCCTC GTACACAGTAATGGAAACACCTACTTGAGTTGGCTTCACCAGA GGCCAGGCCAGCCTCCAAGGCTCCTAATTTATGAAATCTCTAA GCGGTACTCTGGGGTCTCAGACAGATTCAGTGGCAGTGGGGCA GGGACAGATTTCACACTAAAAATCAGCAGGGTGGAAGCTGAG GATGTCGGAATTTACTTCTGCGCGCAAGTTTCACACTTCCCCCG GACGTTCGGCCAAGGGACCAAGGTGGAAATCAAA |

Consistent with antibodies to polysaccharide antigens, it was found that most of the mAbs had low mutation frequency and were less than 10% mutated from the germline sequence. For most mAbs, high concentrations were required to detect reactivity to capsular AM suggesting low binding affinities (FIG. 1). Such low affinities are consistent with other glycan-specific mAbs. One mAb, L1AM04, showed much stronger binding to AM than the other mAbs by ELISA (FIG. 1); this antibody was chosen for more in-depth characterization.

Figures 2A, 2B, 2C, 2D:
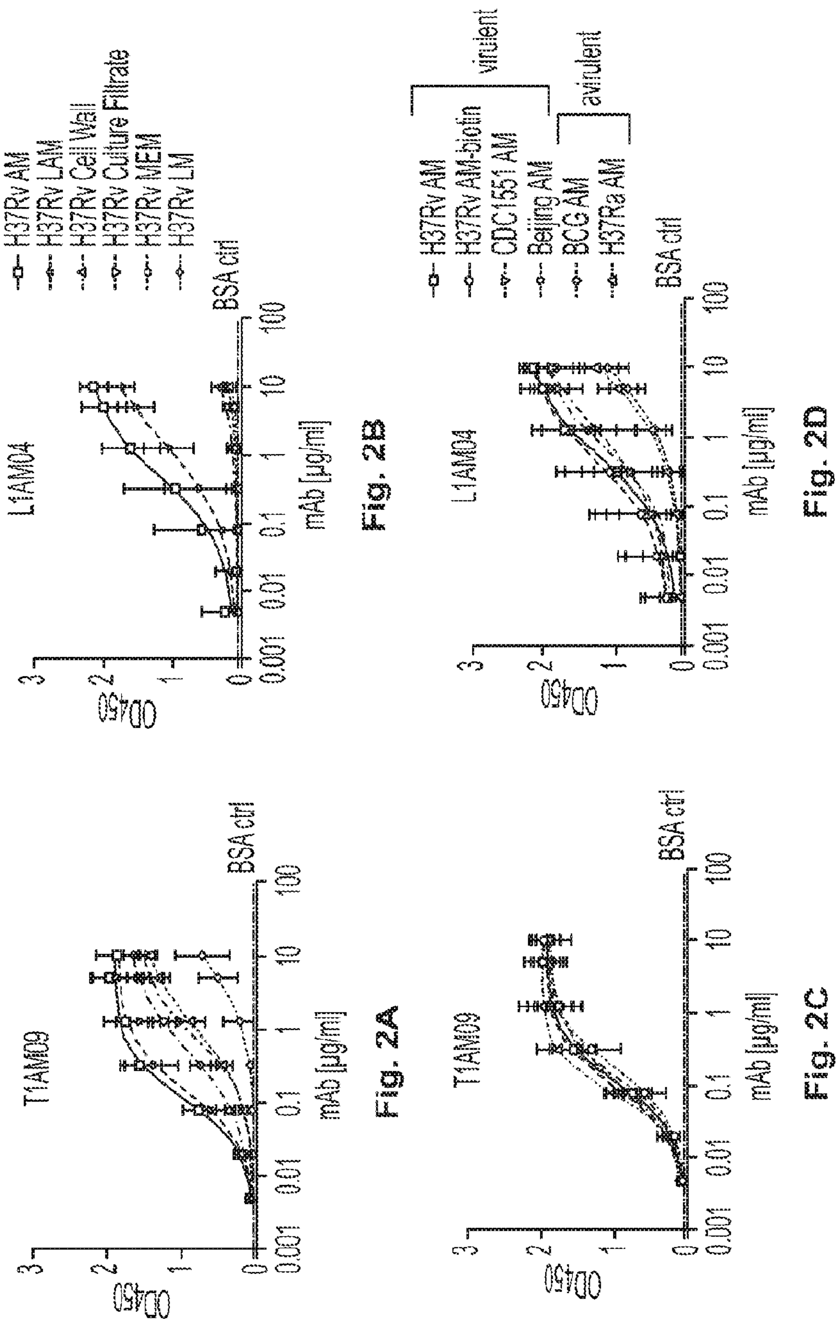
FIGS. 2A, 2B, 2C, and 2D illustrate the characterization of anti-AM mAb cross-reactivity to Mtb components. Binding of T1AM09 (FIGS. 2A and 2C) and L1AM04 (FIGS. 2B and 2D) assessed by ELISA to antigens and fractions isolated from H37Rv (FIGS. 2A and 2B) and to AM isolated from different Mtb strains (FIGS. 2C and 2D). Each data point represents the mean and standard deviation from two or more replicates. Dashed line represents the BSA control.

Example 2: L1AM04 has Distinct Binding Characteristics and Reactivities to Glycan Epitopes Both L1AM04 as well as control antibody T1AM09 (disclosed in PCT application publication WO2019/200255, which is herein incorporated by reference in its entirety) bound strongest to Mtb capsular AM, followed by LAM, and weaker binding to Mtb cell wall, membrane and culture filtrate fractions (FIG. 2). The sequences of T1AM09 are shown in Table 4. The control antibody T1AM09 cross-reacted with AM isolated from various virulent and avirulent strains of the Mtb complex group (FIGS. 2A and 2C). By contrast, L1AM04 barely bound to AM from avirulent strains, indicating reactivity to different glycan epitopes than control antibody T1AM09 (FIG. 2D). Both mAbs had limited binding to the Mtb cell wall glycolipid lipomannan (LM), indicating that reactivity of these mAb was specific to the arabinose component of AM and LAM (FIGS. 2A and 2B). Although T1AM09 and L1AM04 have comparable binding to the biotinylated H37Rv probe (used for sorting) and AM from virulent strains of Mtb, L1AM04 binds significantly less to AM from avirulent strains, indicating L1AM04's recognition is more specific for glycan epitopes of virulent Mtb strains (FIGS. 2C and 2D).

TABLE 4

CDR sequences of antibody T1AM09. CDRs are labeled according to Kabat.

| Sequence | SEQ ID NO: | Sequence |
|---|---|---|
| CDRH1 | 17 | TYWIH |
| CDRH2 | 18 | WIIPKSGGTNYAQKFQG |
| CDRH3 | 19 | GILLNGIGAFDY |
| CRDL1 | 20 | RTSQTVSSNLN |
| CDRL2 | 21 | GISDLHS |
| CDRL3 | 22 | QQSYSLPRT |
| VH-1 | 23 | QVQLVESGAEVKKPGASVKVSCKASGYTF S**TYWIH**WMRQAPGQGPEWMG**WIIPKSGGT** **NYAQKFQG**RVAMTRDTSLNTVYMELSRLT SDDTAVYYCAR**GILLNGIGAFDY**WGQGTL VTVSS |
| VH-2 | 24 | QVQLVESGAEVKKPGASVKVSCKASGYTF A**TYWIH**WMRQAPGQGPEWMG**WIIPKSGGT** **NYAQKFQG**RVAMTRDTSLNTVYMELSRLT SDDTAVYYCAR**GILLNGIGAFDY**WGQGTL VTVSS |
| VL | 25 | DIVMTQSPSSLSASVGDRVTITC**RTSQTV** **SSNLN**WYQQRPGKAPKLLIS**GISDLHS**GV PSRFSGSGSGTDFTLTISSLQPEDSATYY C**QQSYSLPRT**FGQGTKVEIK |

Figure 3:
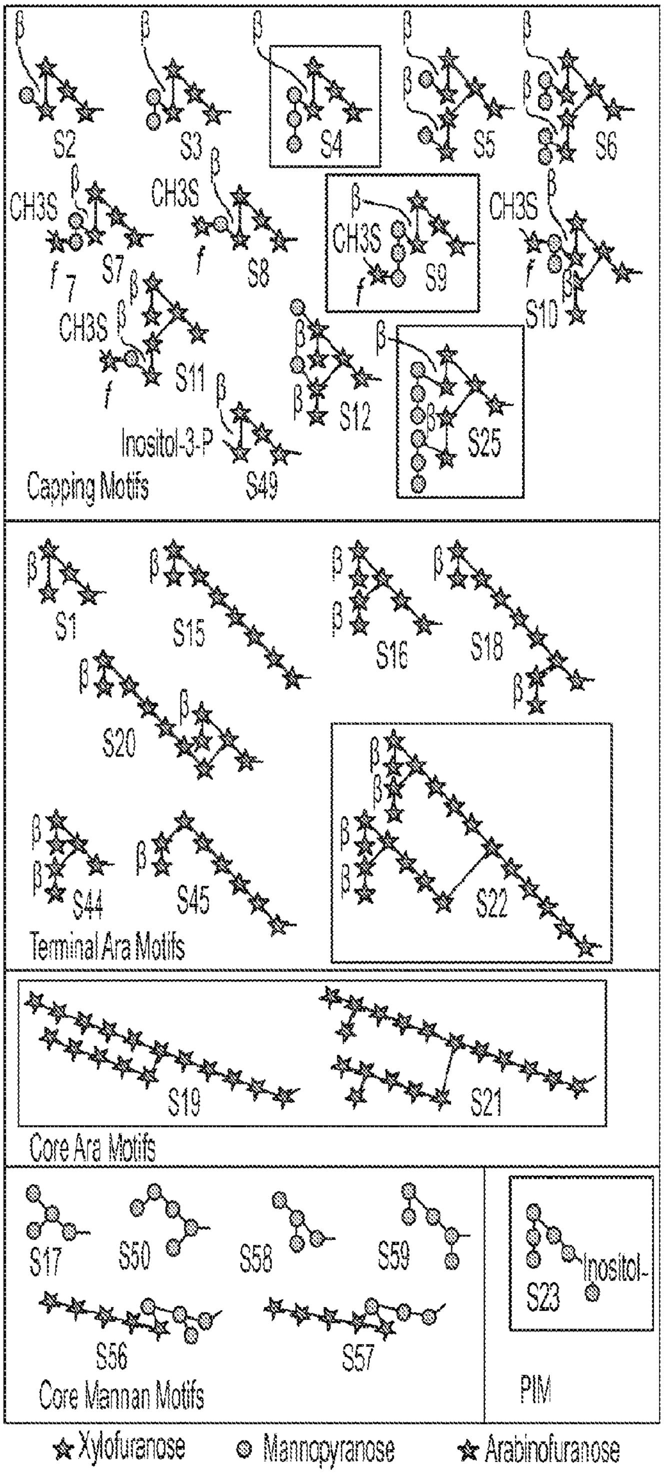
FIG. 3 shows the AM/LAM and PIM motifs with those most strongly recognized by L1AM04 (S4, S9, S23, and S25) and T1AM09 (S19, S21, and S22). Arabinomannan/lipoarabinomannan (AM/LAM) specific fragments (S #1-12, 15-22, 25, 44, 45, 49, 50, 56-59) are marked by the side bar.
Figure 10A:
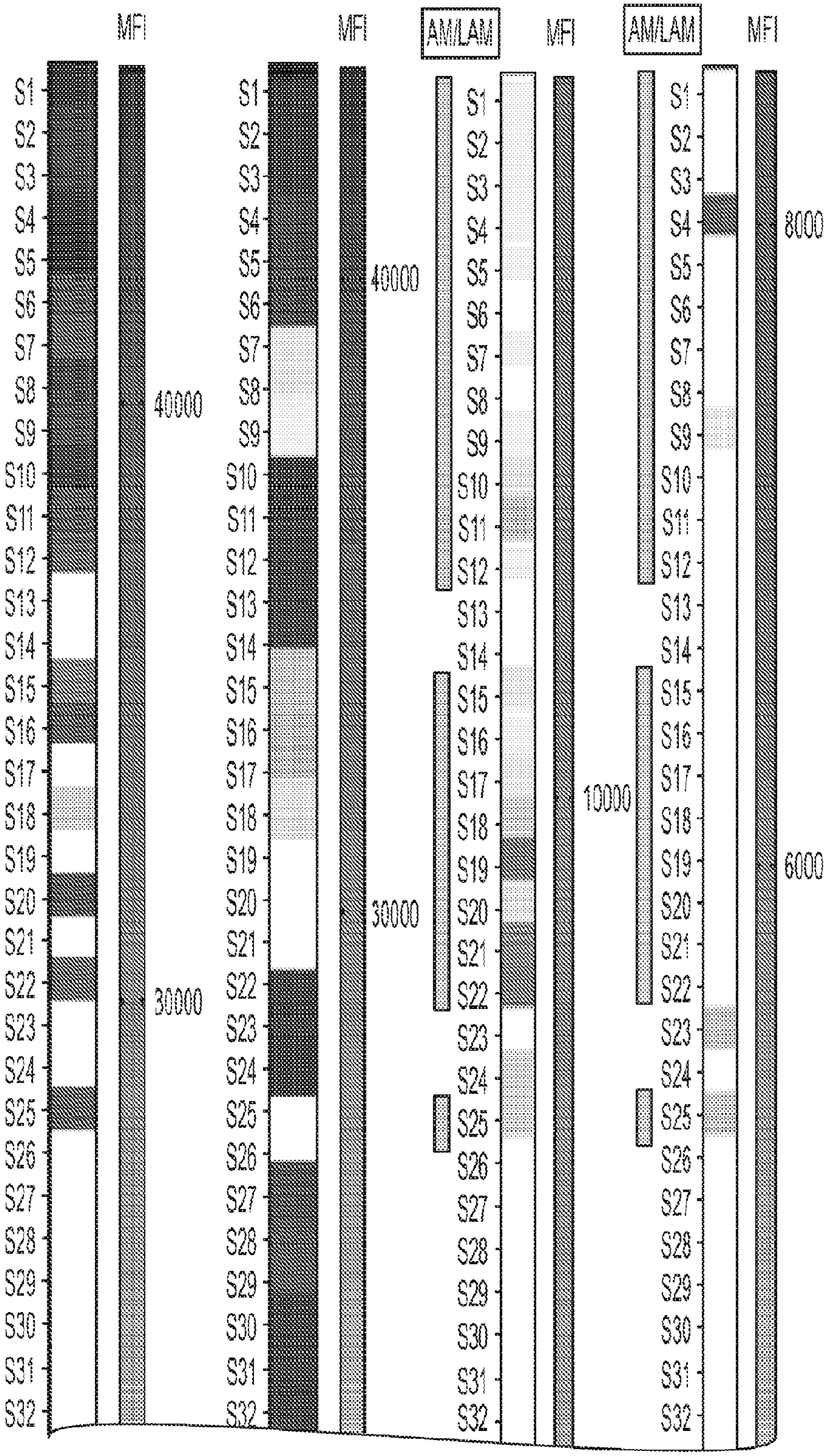
FIGS. 10A and 10B illustrate the binding of mAbs P1AM25, T1AM09, and L1AM04 to synthetic mycobacterial glycans.
Figure 10A:
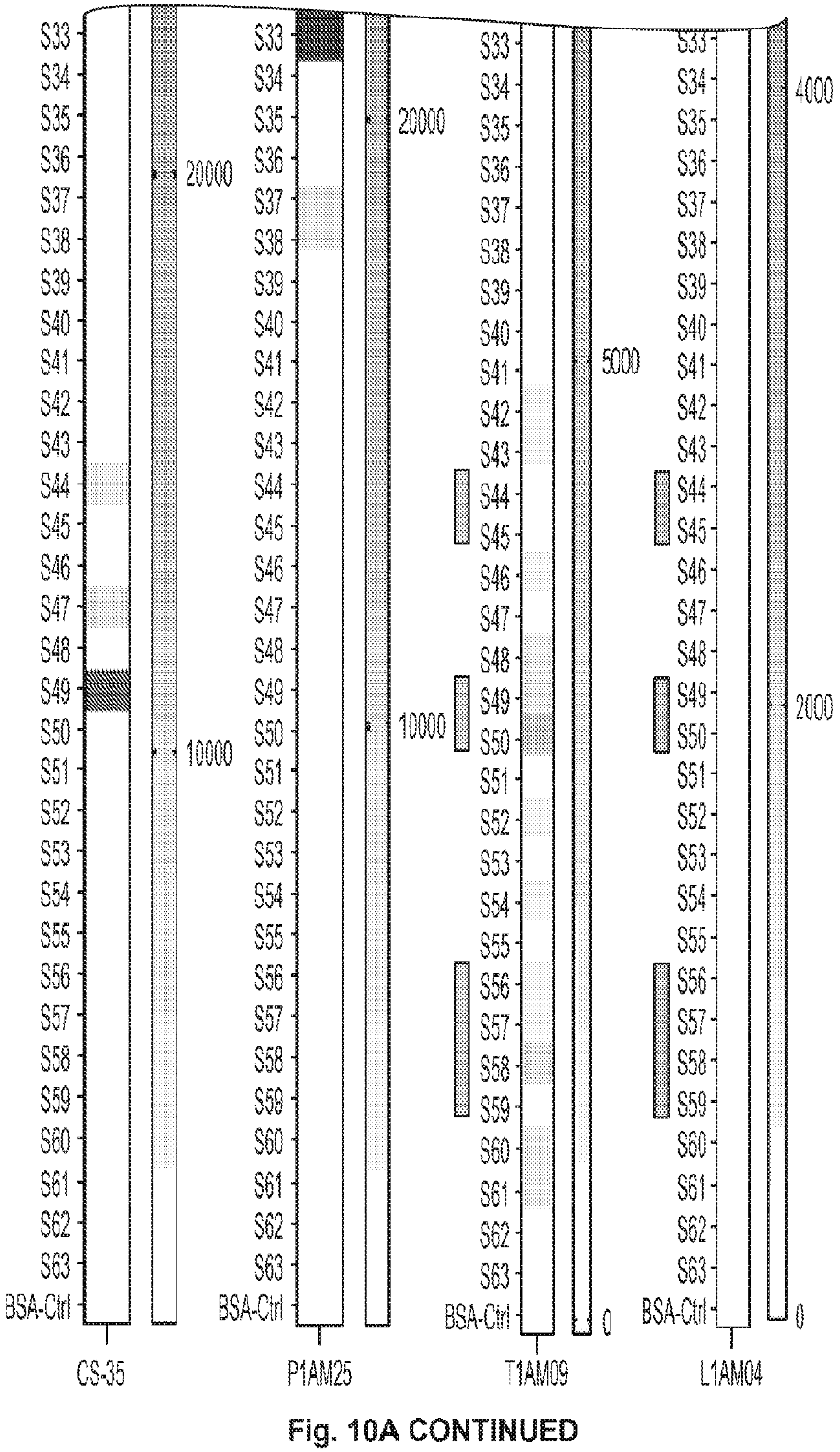

To determine the AM epitopes recognized by L1AM04 and control antibody T1AM09, antibody binding to a broader panel of 63 synthetically generated oligosaccharides was tested. These synthetically generated oligosaccharides were derived from mycobacterial surface glycans which, in addition to the 30 fragments from AM and LAM, included fragments from six other glycan classes (α-glucan, trehalose mycolates, lipooligosachharides (LOSs), phenolic glycolipids (PGLs), phosphatidyl-myo-inositol mannosides (PIMs) and glycopepitdolipids (GPLs). L1AM04 reacted with AM fragments S4, S9, S25, sharing a specific mannose capped arabinan motif (FIGS. 3 and 10A). The reactivity of L1AM04 with one PIM oligosaccharide (S23, also referred to as PIM6) is likely based on cross-reactivity to the shared three-mannose residue motif. Control antibody T1AM09 had the highest reactivity to the AM fragments S19, S21, and S22, which are terminal and core ara motifs sharing long chains of arabinose residues (FIG. 3).

Example 3: L1AM04 is a High-Affinity Binder

The binding affinity of L1AM04 to a biotinylated AM probe was determined using Biolayer Interferometry (BLI). Biotinylated AM was immobilized onto streptavidin sensors and then dipped into solutions of L1AM04 or control antibody T1AM09 at various concentrations. Given the bivalent nature of the IgGs, this measurement does not provide an unambiguous determination of binding kinetics without the potential for avidity but nonetheless can afford some insight into comparative affinities. Hence, the reported dissociation constants are referred to as apparent $K_D$ ($K_{D, app}$).

Figure 4A:
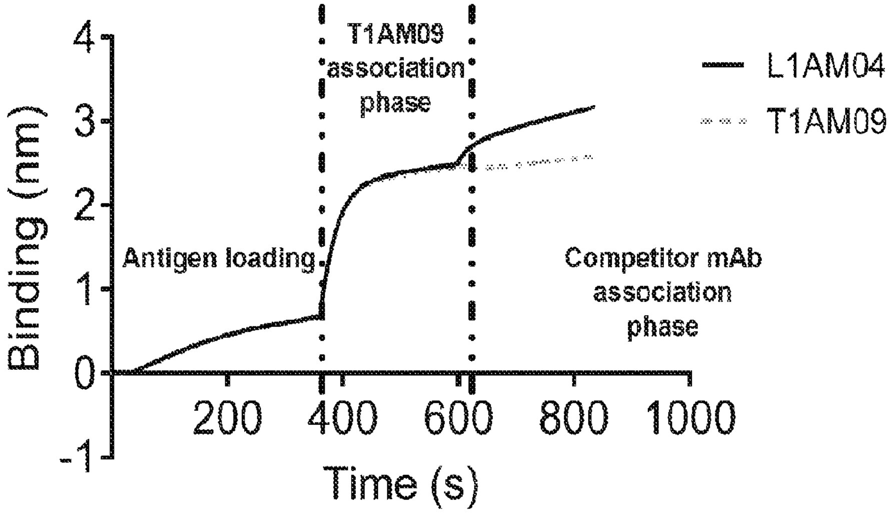
FIGS. 4A and 4B illustrate that T1AM09 and L1AM04 bind to different AM glycan epitopes and do not compete for binding AM. Briefly, to assess epitope binding in a two-phase binding experiment by BLI, biotinylated AM was first immobilized on a streptavidin sensor and then allowed to equilibrate in a solution containing the first mAb. After the binding plateaus, the biosensor was dipped into a second well containing equimolar amounts of the first mAb and test mAb to determine whether the mAbs bind distinct or shared epitopes. For both L1AM04 and control antibody T1AM09, the observed second association curve indicates that these mAbs bind different AM epitopes.

L1AM04 bound to AM with sub-micromolar affinity and rapid association rates (Table 5). Further, cross-competition experiments by BLI indicated binding of T1AM09 and L1AM04 to different glycan epitopes within AM (FIGS. 4A and B). Furthermore, T1AM09 does not target the CS-35 epitope (data not shown). These characteristics are of importance because pairs of high affinity non-competing mAbs that bind to the same antigen, but to a different epitope have significant value for diagnostic and research applications.

TABLE 5

Binding kinetics of monoclonal antibodies analyzed by Bio Layer Interferometry.

| Antibody | $K_{D, app}$ (M) | $K_D$ Error | $K_{on}$ (1/Ms) | $K_{on}$ Error | $K_{off}$ (1/s) | $K_{off}$ Error |
|---|---|---|---|---|---|---|
| T1AM09 | 2.6E−08 | 3.5E−10 | 2.6E+05 | 3.1E+03 | 6.9E−03 | 4.0E−05 |
| L1AM04 | 9.6E−08 | 5.6E−09 | 2.5E+05 | 1.8E+04 | 1.9E−02 | 3.3E−04 |
| CS-35 | <1.0E−12 | <1.0E−12 | 3.1E+04 | 2.8E+02 | <1.0E−07 | NA |

Example 4: Antibodies L1AM04 can be Used in a Urinary LAM ELISA

Figure 4B:
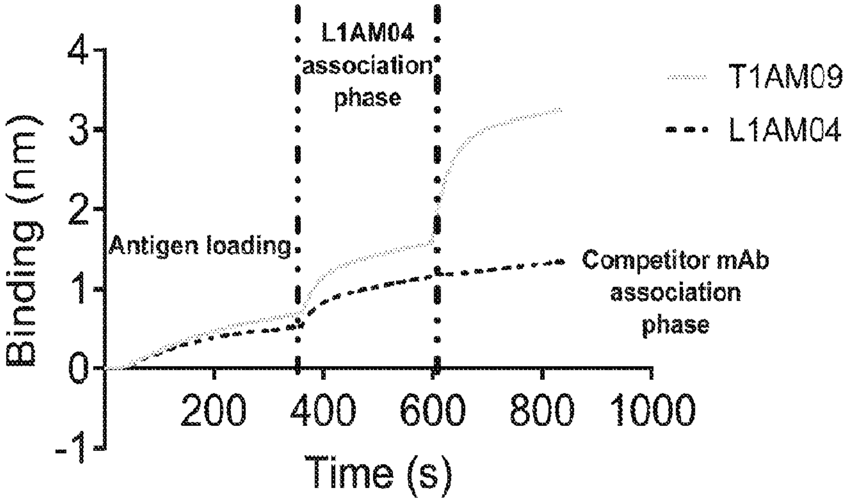
Figure 5A:
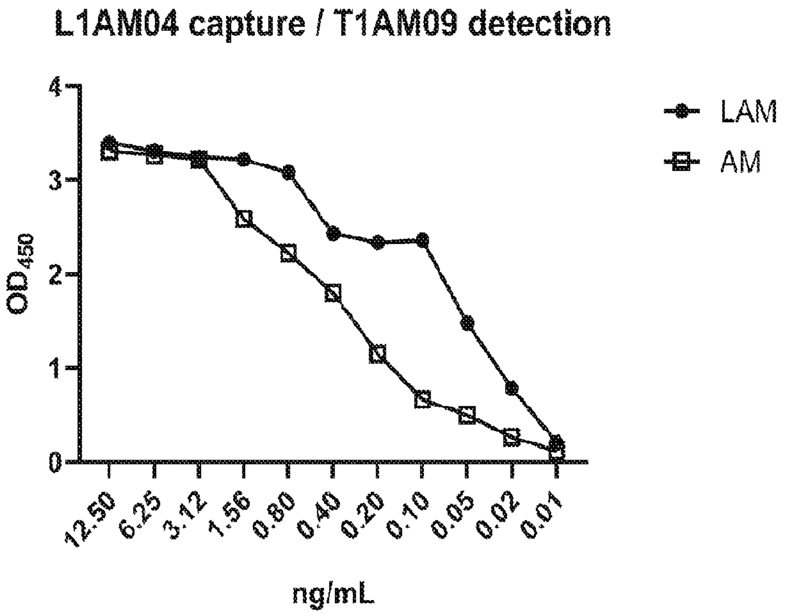
FIGS. 5A and 5B illustrate that a combination of high affinity human mAbs to distinct AM epitopes can detect low levels of LAM and AM in urine.
Figure 5B:
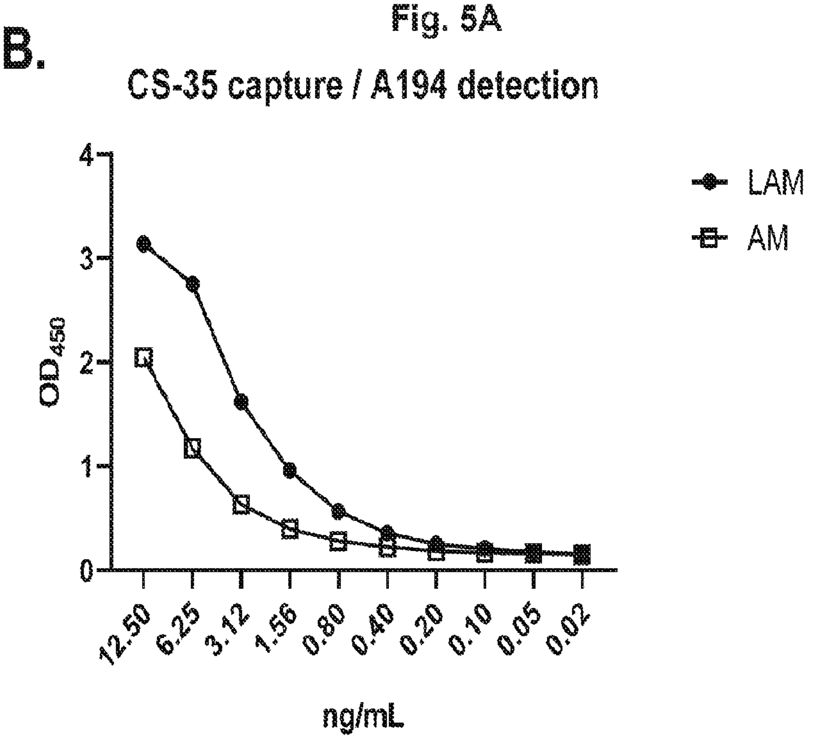

Detection of LAM in the urine of TB patients is based on the use of a capture mAb in combination with a detection mAb for LAM. These mAbs should recognize different AM/LAM epitopes. The AM OS glycan microarray and epitope binning data indicated that T1AM09, L1AM04, and CS-35 could be used as different pairs in a urinary LAM (U-LAM) sandwich ELISA (FIGS. 3 and 4). To assess the potential of the mAbs for diagnostic assays, the binding properties of T1AM09's and L1AM04's to LAM spiked into urine from a healthy volunteer was characterized (FIG. 5). The mAb pair CS-35 and A194 was used as a reference. The combination of L1AM04 as a capture mAb and biotinylated T1AM09 as a detection mAb was highly sensitive for the detection of urinary LAM in low concentrations (limit of detection 20 μg/ml, FIG. 5A). These data show that including high-affinity human anti-AM mAbs generated through single B cell sorting and recognizing distinct glycan epitopes can contribute to the improvement of currently available urinary LAM detection tests.

Example 5: Binding of Antibody L1AM04 to Mtb Strains

Figures 6A, 6B, 6C:
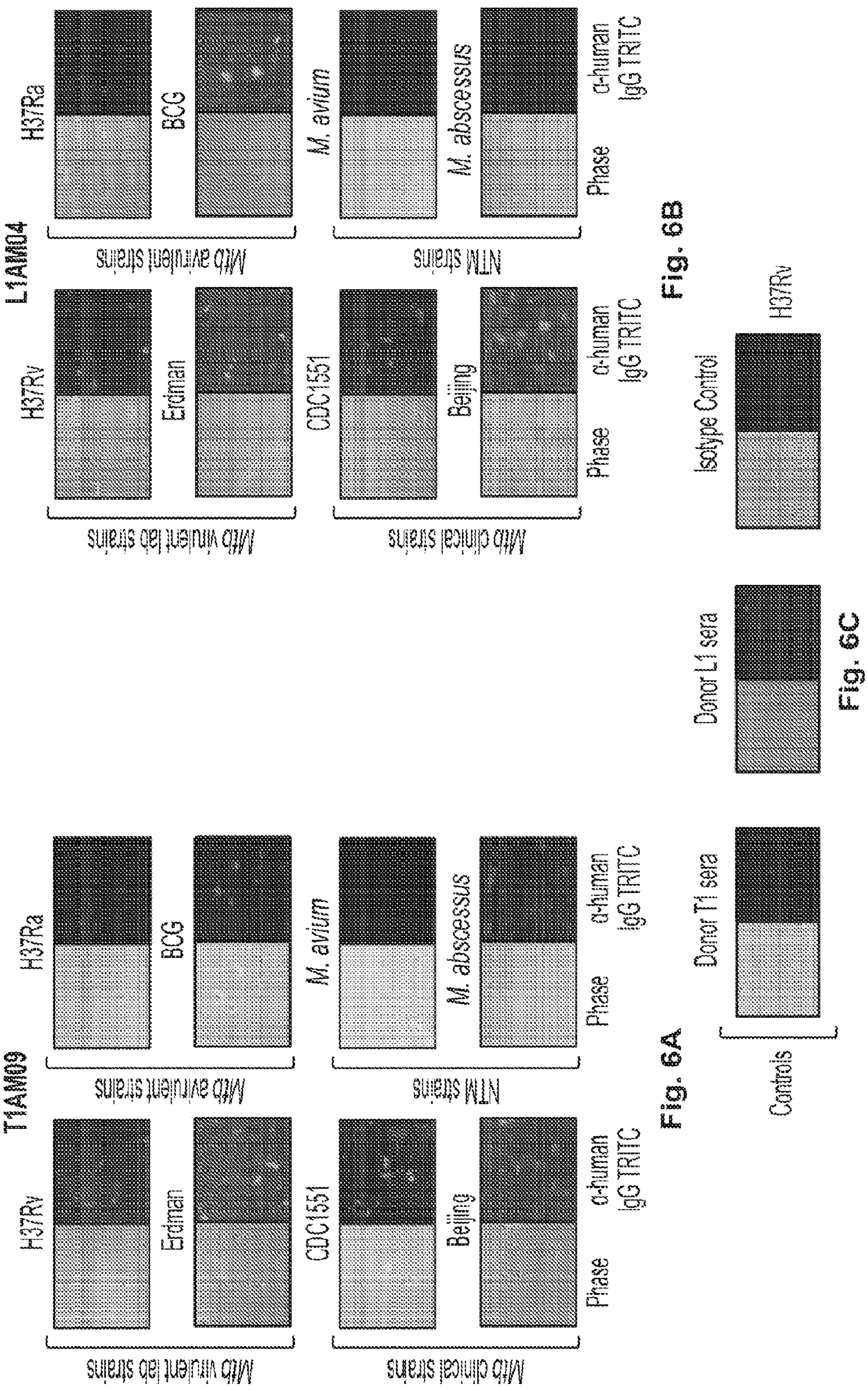
FIGS. 6A, 6B, and 6C illustrate that T1AM09 and L1AM04 show distinct binding to mycobacterial strains by immunofluorescence (mycobacteria were grown without detergent to preserve the capsule). T1AM09 (FIG. 6A) and L1AM04 (FIG. 6B) binding to virulent laboratory (H37Rv and Erdman) and clinical strains (CDC1551 and Beijing) of Mtb, avirulent strains of the Mtb complex group (H37Ra and BCG Pasteur) and non-tuberculosis mycobacteria (*M. avium* and *M. abscessus*).
Figure 7A:
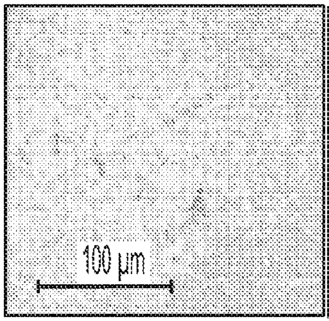
FIGS. 7A, 7B, 7C, 7D, 7E, 7F, 7G, 7H, and 7I show that T1AM09 and L1AM04 detect extra- and intracellular Mtb and LAM in lung tissues of Mtb-infected mice. Histology and immunohistochemistry of Mtb infected murine lung (scale bar 60 μm) showing intra- and extracellular staining of Mtb CDC1551 by T1AM09 (FIG. 7A) and L1AM04 (FIG. 7B).
Figure 7B:
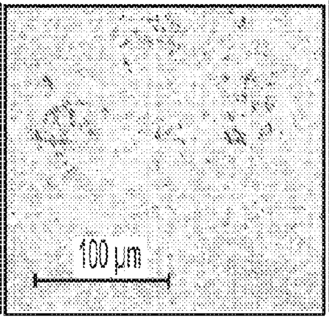
Figure 7C:
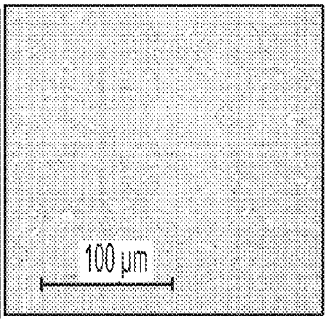
Figure 7D:
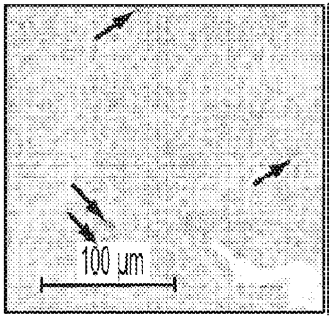
Figure 7E:
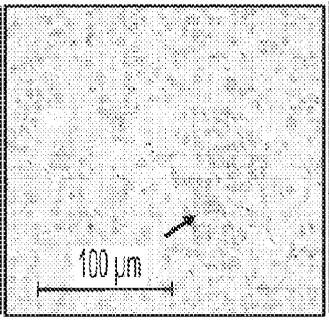
Figure 7F:
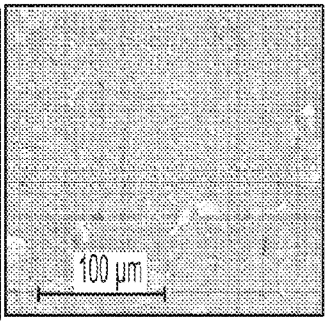
Figure 7G:
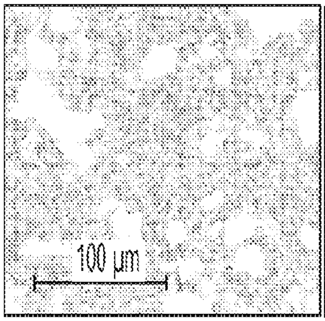
Figure 7H:
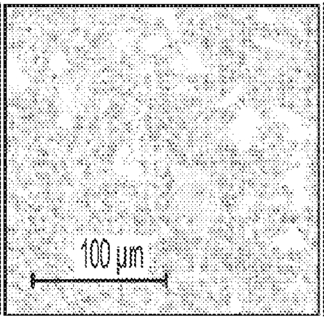
Figure 7I:
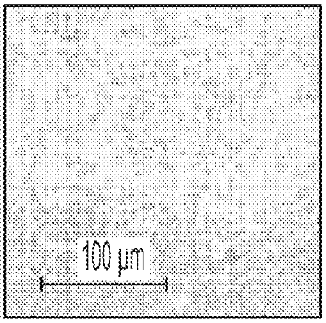

The binding of antibody L1AM04 as well as control antibody T1AM09 to different Mtb strains (grown without detergent to preserve the capsule) was determined. Using fluorescent microscopy, it was shown that at concentrations of 10 μg/ml mAbs L1AM04 binds to both avirulent (H37Ra, BCG) and virulent laboratory (H37Rv and Erdman) as well as clinical strains (CDC1551 and Beijing) of the Mtb complex group (FIG. 6B). Of the non-tuberculous mycobacteria, T1AM09 bound to *M. abscessus* but not to *M. avium*, and L1AM04 bound to neither, supporting their differences glycan epitope recognition (FIG. 6).

Example 6: Binding of Antibody L1AM04 to Mtb Strains and Mtb LAM

To demonstrate the utility of L1AM04 for the detection of Mtb and LAM in the tissue of CDC1551 and Erdman infected mice, mAbs binding was evaluated by immunohistochemistry (IHC) staining, using Acid-Fast Bacilli (AFB) staining (Ziehl-Neelsen) as a positive control. Both L1AM04 and control antibody T1AM09 detected extracellular and intracellular bacilli and AM/LAM throughout infected lungs with minimal off-target effects (FIG. 7), with L1AM04 showing significantly lower background staining. By contrast, AFB staining showed weaker positivity for bacilli, was only positive in highly inflammatory regions and did not improve when the alternative (Fite's method) was used. These data demonstrate the utility of L1AM04 for the in situ detection of LAM in infected tissues and show that both mAbs could improve the sensitivity for Mtb detection in infected tissue.

Example 7: Generation of Antibody P1AM25

Monoclonal antibody P1AM25 was generated using the targeted, flow cytometry-based strategy described in Example 1. Donor P1 was selected for B cell sorting and antibody generation. Donor P1 was an asymptomatic, Mantoux tuberculin skin test (TST)+ and interferon-gamma release assay (IGRA; QuantiFERON-TB Gold In-Tube) positive foreign-born adult with a reported history of childhood TB.

The CDR and variable chain sequences of P1AM25 are provided in Tables 6 and 7.

TABLE 6

CDR sequences of antibody P1AM25.

| | Kabat numbering | |
|---|---|---|
| CDR | SEQ ID NO: | Amino acid sequence |
| CDRH1 | 26 | SYYLS |
| CDRH2 | 27 | YMFHRGSTNRNPSLRS |
| CDRH3 | 28 | HLGIVGVTNAAFDI |
| CRDL1 | 29 | SGSSSNIGNNYVS |
| CDRL2 | 30 | QNDKRPS |
| CDRL3 | 31 | GTWDRSLNADV |

TABLE 7

Heavy and light variable chains sequences of P1AM25. CDRs are indicated (Kabat numbering).

| Sequence | SEQ ID NO: | Sequence |
|---|---|---|
| VH | 32 | QVQLQESGPGLVEPSETLSLTCTVSGGSIR**SYYLS**WIRQSPKKG LEWIG**YMFHRGSTNRNPSLRS**RVTMSLDTSKNQFSLKLTSVT AADTAVYYCAT**HLGIVGVTNAAFDI**WGQGTMVTVSS |
| VH | 33 | CAGGTGCAGCTGCAGGAGTCGGGCCCAGGACTGGTGGAGC CTTCGGAGACCCTGTCCCTCACGTGCACTGTCTCTGGTGGCT CCATCAGAAGTTACTACTTGAGCTGGATCCGGCAGTCCCCG AAGAAGGGACTGGAGTGGATTGGATATATGTTTCACCGTGG GAGCACCAACCGCAACCCCTCCCTCAGGAGTCGGGTCACCA TGTCACTGGACACGTCCAAGAACCAGTTCTCCCTGAAACTG ACCTCTGTGACCGCCGCAGACACGGCCGTCTATTATTGTGC GACACATCTCGGAATAGTGGGGGTTACTAACGCTGCTTTTG ATATCTGGGGCCAAGGGACAATGGTCACCGTCTCTTCAG |
| VL | 34 | QSVLTQPPSVSAAPGQKVTISC**SGSSSNIGNNYVS**WYQLLPGT APKLLIY**QNDKRPS**DIPDRFSGSKSGTSATLGITGLQTGDEADY YC**GTWDRSLNADV**FGGGTKLTVL |

TABLE 7-continued

Heavy and light variable chains sequences of P1AM25. CDRs are indicated (Kabat numbering).

| Sequence | SEQ ID NO: | Sequence |
|---|---|---|
| VL | 35 | CAGTCTGTGCTGACGCAGCCGCCCTCAGTGTCTGCGGCCCC AGGACAGAAGGTCACCATCTCCTGCTCTGGAAGCAGCTCCA ACATTGGAAATAATTATGTATCCTGGTATCAGTTACTCCCAG GAACAGCCCCCAAACTCCTCATCTATCAAAATGATAAGCGA CCCTCAGACATTCCTGACCGATTCTCTGGCTCCAAGTCTGGC ACGTCAGCCACCCTGGGCATCACCGGACTCCAGACTGGGGA CGAGGCCGATTATTACTGCGGAACATGGGATAGAAGCCTGA ATGCTGACGTTTTCGGCGGGGGGACCAAGCTGACCGTCCTA G |

Example 8: Binding of Antibody P1AM25 to Capsular AM

The binding of antibody P1AM25 to capsular AMV was assessed using an ELISA. For this, AM isolated from H37Rv was coated on a 96-well Maxisorp plate at 10 μg/mL. Anti-Mtb AM mAbs P1AM25, T1AM09, and L1AM04 were applied as primary antibodies and the binding was detected using an HRP-conjugated anti-human IgG-Fc.

Figure 8:
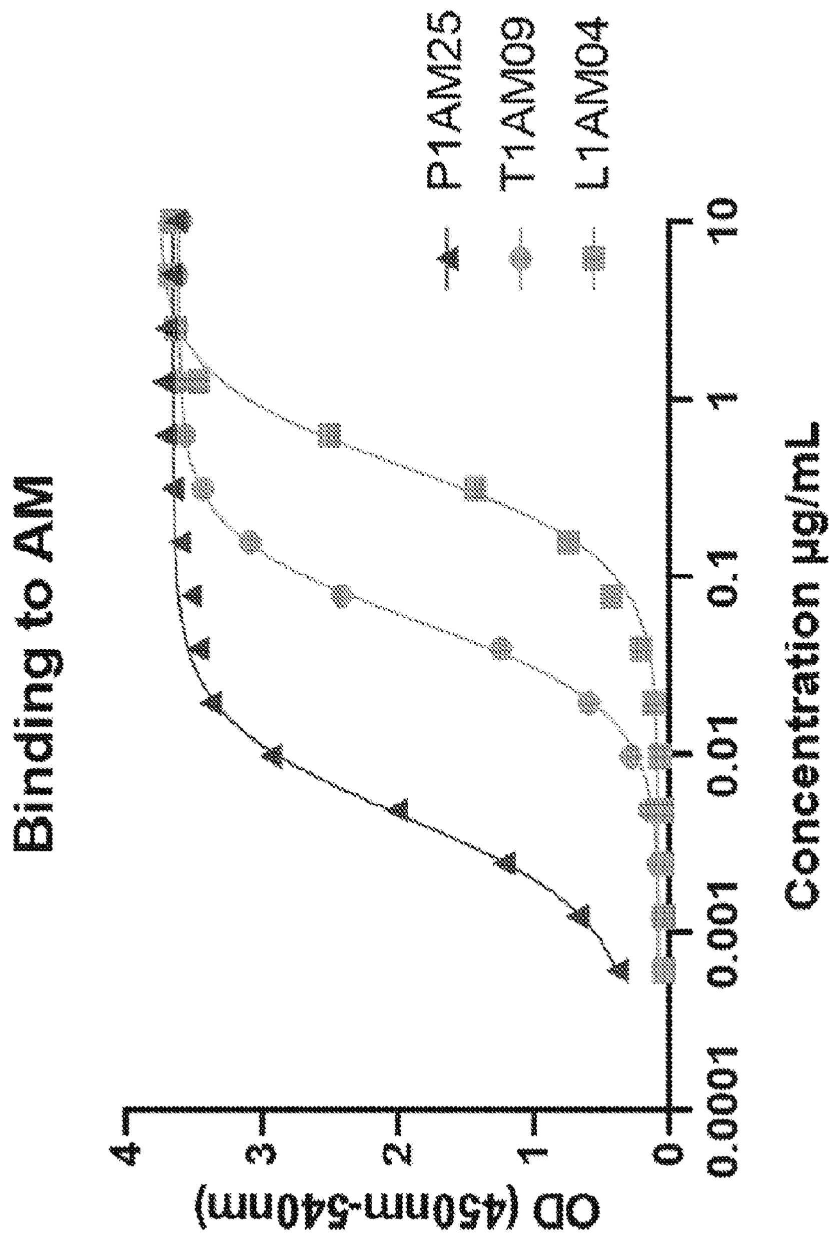
FIG. 8 shows binding of human monoclonal antibodies P1AM25, T1AM09, and L1AM04 to H37Rv AM as determined by ELISA.

Human monoclonal antibody P1AM25 showed an exceptionally high affinity compared to high affinity anti-AM monoclonal antibodies T1AM109 and L1AM04 (FIG. 8).

Example 9: Effect of Antibody P1AM25 on the Phagocytosis of Mtb by Macrophages To determine *M. tuberculosis* phagocytosis by U937R3a cells or THP1 cells (both human monocyte cell lines), respectively, in presence of anti-AM mAbs, phorbol-12-myristate-13-acetate (PMA)-differentiated U937R3a cells or THP1 cells, respectively, were seeded at $5\times10^4$ (U937R3a cells) or $1\times10^5$ (THP1 cells) per well in a 96-well plate. The cells were infected with H37Ra-FITC at MOI of 20 in the presence of different anti-AM mAbs at for 3 hours.

Figure 9A:
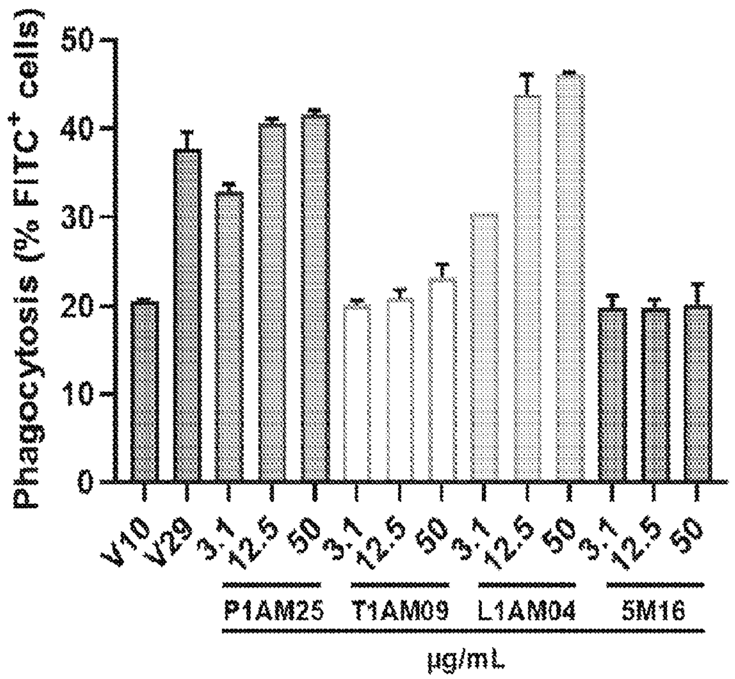
Figure 9B:
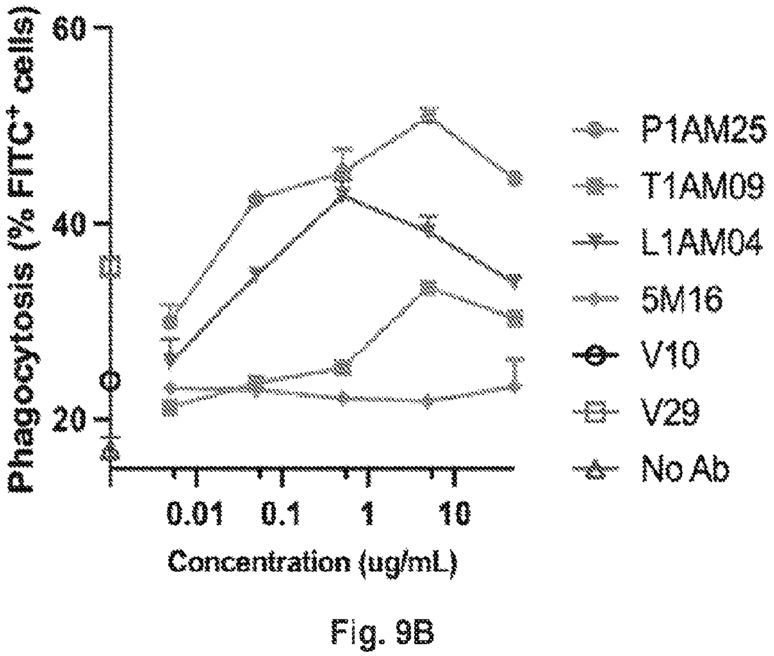

Enhanced *M. tuberculosis* phagocytosis by U937R3a cells (FIG. 9A) and THP1 cells (FIG. 9B) was found in the presence of antibody P1AM25 and L1AM04.

Example 10: Determination of the Glycan Epitope for Antibody P1AM25

Figure 10B:
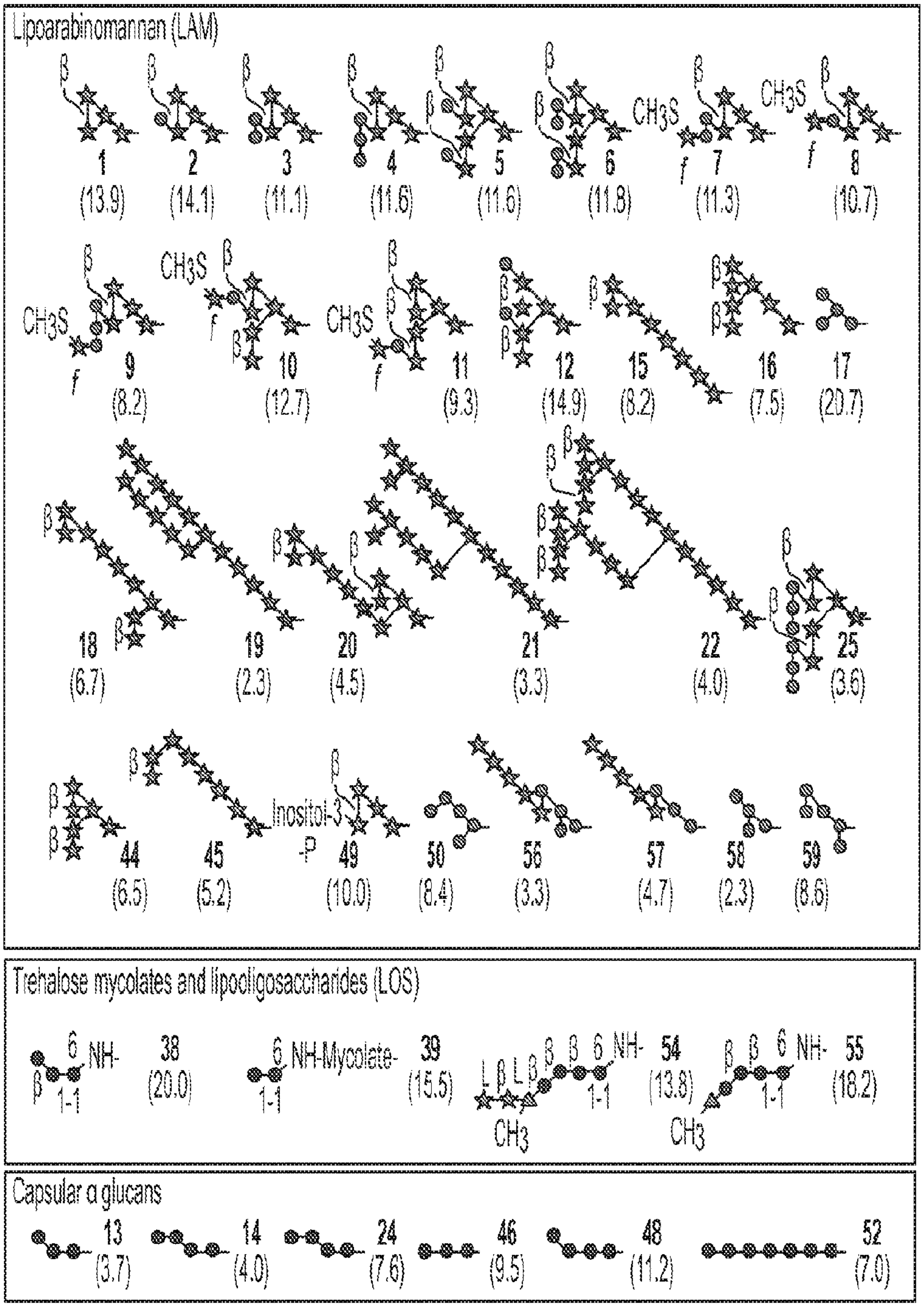
Figure 10B:
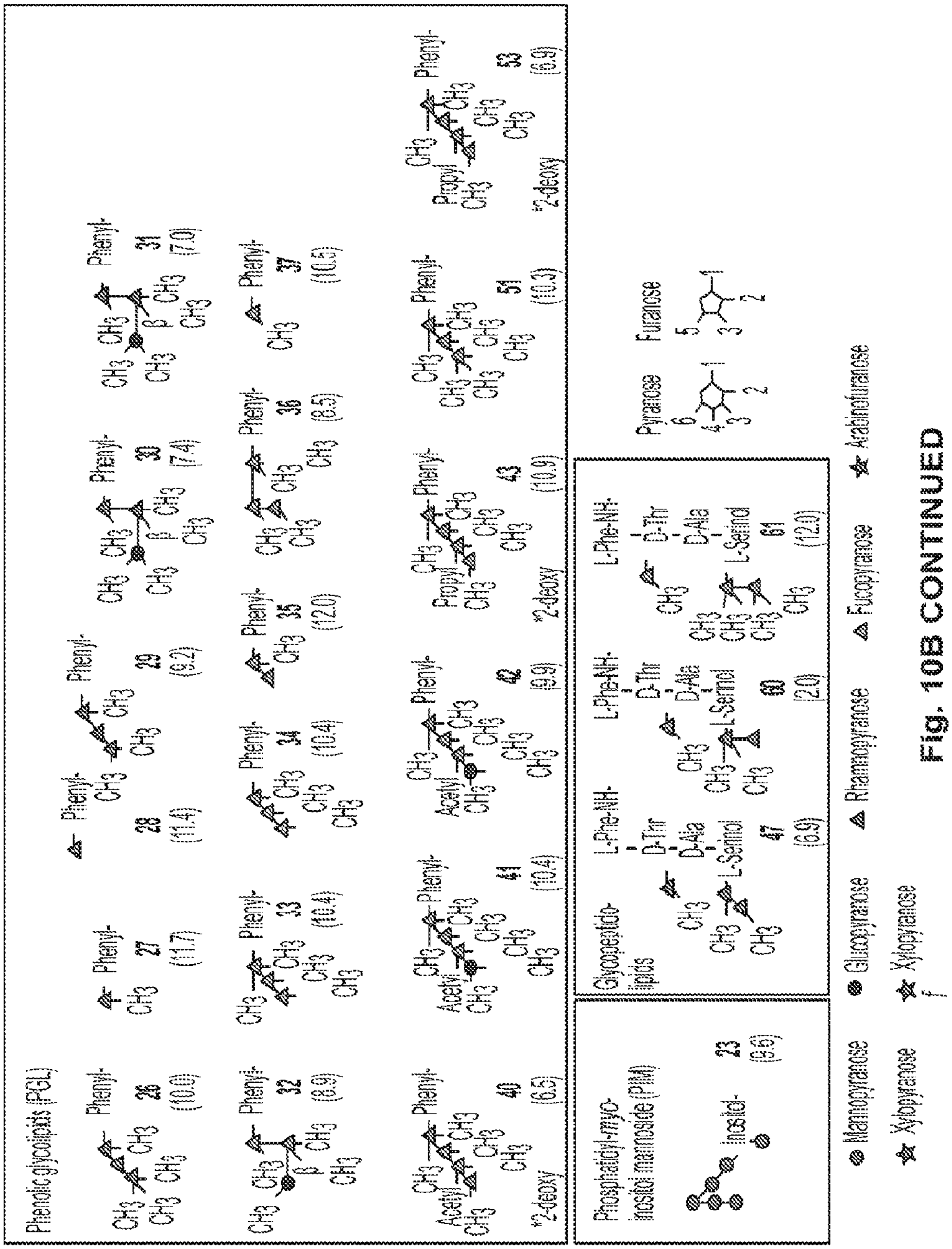

The reactivity of P1AM25 to mycobacterial envelope glycan epitopes was compared to murine mAb CS35 and human mAbs T1AM09 and L1AM04 using a panel of 63 synthetically generated oligosaccharides (FIG. 10B). The Median Fluorescence Intensity (MFI) of P1AM25 (5 μg/mL) binding 63 mycobacterial oligosaccharide fragments was compared to the MFI for T1AM09 (5 μg/mL), L1AM04 (5 μg/mL), and CS-35 (1:100 dilution) (FIG. 10A).

Example 11: Affinity of P1AM25 to AM as Analyzed by Bio-Layer Interferometry (BLI)

The binding affinity of antibody P1AM25 was determined with BLI (biotinylated AM: 0.5 μg/mL; antibody 2.3 nM-37.5 nM). The $K_D$ was determined to be 3.38 $10^{-9}$ M.

Example 12: Epitope Binning of P1AM25 to AM as Determined by BLI

Figure 11A:
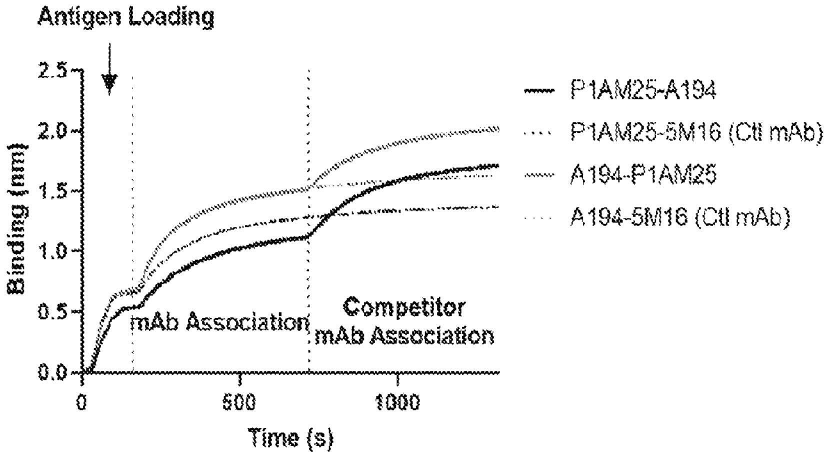
FIGS. 11A and 11B illustrate epitope binning experiments for P1AM25. Performed were two-phase binding experiment detecting P1AM25 and reference antibodies A194 (FIG. 11A) or CS-35 (FIG. 11B), respectively, competing with each other. Solid lines show association curve with competitor monoclonal antibodies (mAbs). Dashed lines show the association curve with an irrelevant control mAb. Biotinylated AM: 0.5 μg/mL. Antibody concentration 37.5 nM.
Figure 11B:
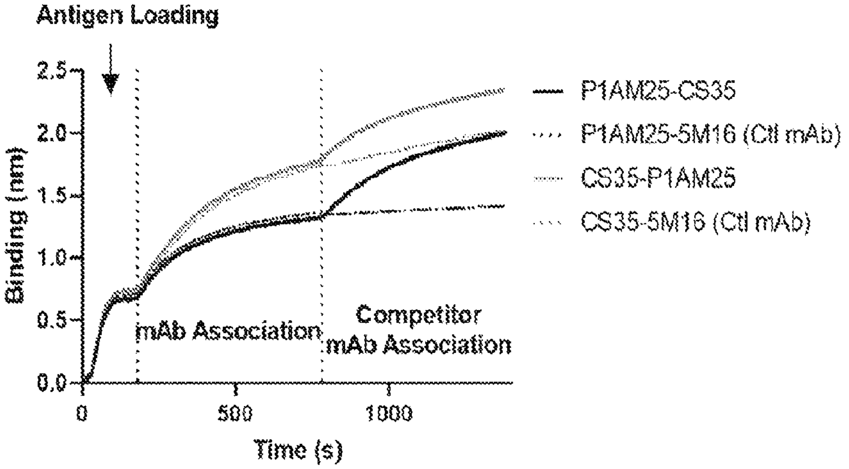

Epitope binning experiments for P1AM25 were performed using BLI. Performed were two-phase binding experiment detecting P1AM25 and A194 (FIG. 11A) or CS35 (FIG. 11B), respectively, showing that P1AM25 does neither compete with A194 nor with CS35.

Figure 12:
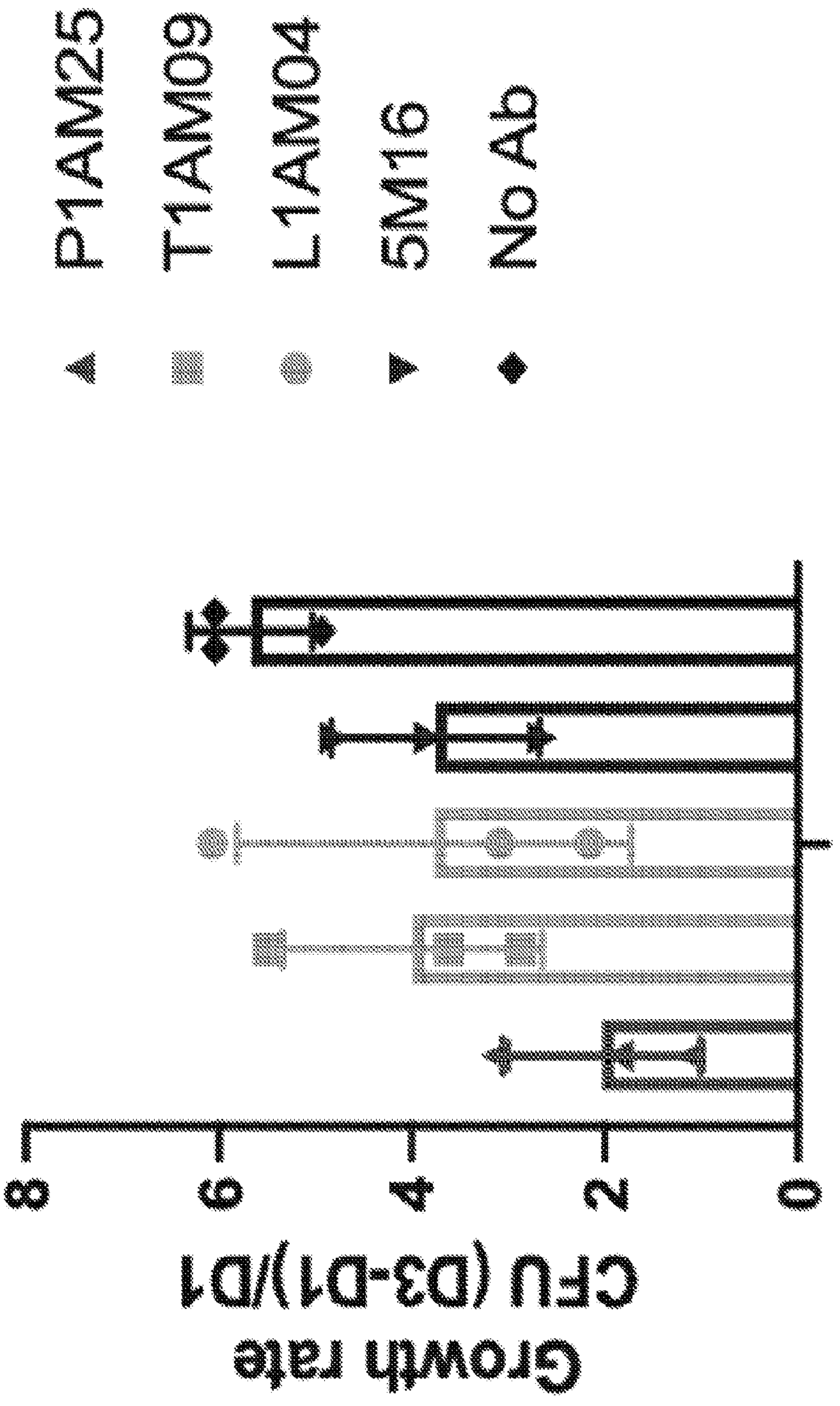
FIG. 12 shows intracellular growth reduction of Mtb (H37Rv) in THP-1 cell in the presence of P1AM25 and L1AM04. Shown is a decrease in Mtb intracellular growth in THP-1 cell in the presence of 5 μg/mL P1AM25.

Example 13: Effect of Antibody P1AM25 on Intracellular Mtb Growth in THP-1 Differentiated Macrophages To determine the effect of antibody P1AM25 on intracellular Mtb growth in PMA-differentiated THP-1 cells, the cells seeded at $0.5\times10^5$ per well in a 96-well plate. The cells were infected with H37Rv at MOI of 1 in the presence of different AM mAbs at 5 μg/mL for 2 hours (D1). Wells were washed and cell lysates were plated on 7H10 agar plate after infection to determine the uptake of bacteria on D1. Wells for D3 were washed, refilled with fresh media containing mAbs, and incubated for 48 hours. Supernatant and cell lysates were plated on 7H10 agar plate on D3. An intracellular growth reduction of Mtb in THP-1 cell in the presence of P1AM25 was observed (FIG. 12).

TABLE 8

Overview of amino acid sequences.

| Type of sequence | SEQ ID NO: L1AM04 Kabat | L1AM04 IMGT | T1AM09 | P1AM25 |
|---|---|---|---|---|
| CDRH1 | 1 | 11 | 17 | 26 |
| CDRH2 | 2 | 12 | 18 | 27 |
| CDRH3 | 3 | 13 | 19 | 28 |
| CRDL1 | 4 | 14 | 20 | 29 |
| CDRL2 | 5 | 15 | 21 | 30 |
| CDRL3 | 6 | 16 | 22 | 31 |
| VH-1 | 7 | | 23 | 32 |
| VH-2 | | | 24 | |
| VL | 8 | | 25 | 34 |

TABLE 9

Overview of nucleic acid sequences.

| Type of sequence | SEQ ID NO: L1AM04 | SEQ ID NO: P1AM25 |
|---|---|---|
| VH | 9 | 33 |
| VL | 10 | 35 |

What is claimed is:

1. A method of reducing activity of *Mycobacterium tuberculosis* (Mtb) arabinomannan (AM) in a subject in need thereof, the method comprising administering to said subject an anti-Mtb AM antibody or Mtb AM-binding fragment thereof, wherein the anti-Mtb AM antibody or Mtb AM-binding fragment thereof comprises a heavy chain variable region and a light chain variable region, wherein each of the heavy chain and the light chain variable regions comprises a CDR1, CDR2, and CDR3, and wherein:

(a) CDR1H comprises SEQ ID NO:1, CDR2H comprises SEQ ID NO:2, CDR3H comprises SEQ ID NO:3, CDR1L comprises SEQ ID NO:4, CDR2L comprises SEQ ID NO:5, and CDR3L comprises SEQ ID NO:6; or (b) CDR1H comprises SEQ ID NO:26, CDR2H comprises SEQ ID NO:27, CDR3H comprises SEQ ID NO:28, CDR1L comprises SEQ ID NO:29, CDR2L comprises SEQ ID NO:30, and CDR3L comprises SEQ ID NO:31.

2. A method of treating an Mtb infection in a subject in need thereof, the method comprising administering to the subject an amount of an anti-Mtb AM antibody or Mtb AM-binding fragment thereof, wherein the anti-Mtb AM antibody or Mtb AM-binding fragment thereof comprises a heavy chain variable region and a light chain variable region, wherein each of the heavy chain and the light chain variable regions comprises a CDR1, CDR2, and CDR3, and wherein:

(a) CDR1H comprises SEQ ID NO:1, CDR2H comprises SEQ ID NO:2, CDR3H comprises SEQ ID NO:3, CDR1L comprises SEQ ID NO:4, CDR2L comprises SEQ ID NO:5, and CDR3L comprises SEQ ID NO:6; or (b) CDR1H comprises SEQ ID NO:26, CDR2H comprises SEQ ID NO:27, CDR3H comprises SEQ ID NO:28, CDR1L comprises SEQ ID NO:29, CDR2L comprises SEQ ID NO:30, and CDR3L comprises SEQ ID NO:31.

3. A method of treating a disease, disorder, or condition mediated by, or related to increased activity of Mtb in a subject in need thereof, the method comprising administering to said subject an anti-Mtb AM antibody or Mtb AM-binding fragment thereof, wherein the anti-Mtb AM antibody or Mtb AM-binding fragment thereof comprises a heavy chain variable region and a light chain variable region, wherein each of the heavy chain and the light chain variable regions comprises a CDR1, CDR2, and CDR3, and wherein:

(a) CDR1H comprises SEQ ID NO:1, CDR2H comprises SEQ ID NO:2, CDR3H comprises SEQ ID NO:3, CDR1L comprises SEQ ID NO:4, CDR2L comprises SEQ ID NO:5, and CDR3L comprises SEQ ID NO:6; or (b) CDR1H comprises SEQ ID NO:26, CDR2H comprises SEQ ID NO:27, CDR3H comprises SEQ ID NO:28, CDR1L comprises SEQ ID NO:29, CDR2L comprises SEQ ID NO:30, and CDR3L comprises SEQ ID NO:31.

4. An assay device for selectively detecting one or more bacteria from the *Mycobacterium tuberculosis* complex (MTC) group in a biological sample, the assay device comprising:

(a) a first portion comprising a first plurality of anti-Mtb AM antibodies or Mtb AM-binding fragments thereof, wherein the anti-Mtb AM antibodies or Mtb AM-binding fragments thereof are attached to a reporting entity, wherein the anti-Mtb AM antibodies or Mtb AM-binding fragments thereof each comprise a heavy chain variable region and a light chain variable region, wherein each of the heavy chain and the light chain variable regions comprises a CDR1, CDR2, and CDR3, and wherein:

(i) CDR1H comprises SEQ ID NO:1, CDR2H comprises SEQ ID NO:2, CDR3H comprises SEQ ID NO:3, CDR1L comprises SEQ ID NO:4, CDR2L comprises SEQ ID NO:5, and CDR3L comprises SEQ ID NO:6; or (ii) CDR1H comprises SEQ ID NO:26, CDR2H comprises SEQ ID NO:27, CDR3H comprises SEQ ID NO:28, CDR1L comprises SEQ ID NO:29, CDR2L comprises SEQ ID NO:30, and CDR3L comprises SEQ ID NO:31; and (b) a second portion comprising a second plurality of anti-Mtb AM antibodies or Mtb AM-binding fragments thereof or anti-mycobacterial AM antibodies.

5. The assay device of claim 4, wherein each of the anti-Mtb AM antibodies or Mtb AM-binding fragments thereof or anti-mycobacterial AM antibodies in the second plurality of anti-Mtb AM antibodies or Mtb AM-binding fragments thereof or anti-mycobacterial AM antibodies comprises antib a heavy chain variable region and a light chain variable region, wherein each of the heavy chain and the light chain variable regions comprises a CDR1, CDR2, and CDR3, and wherein CDR1H comprises SEQ ID NO:17, CDR2H comprises SEQ ID NO:18, CDR3H comprises SEQ ID NO:19, CDR1L comprises SEQ ID NO:20, CDR2L comprises SEQ ID NO: 21, and CDR3L comprises SEQ ID NO:22.

6. An assay device for selectively detecting one or more bacteria from the MTC group in a biological sample, the assay device comprising:

(a) a first portion comprising a first plurality of anti-Mtb AM antibodies or Mtb AM-binding fragments thereof, wherein the anti-Mtb AM antibodies or Mtb AM-binding fragments thereof are attached to a reporting entity, wherein anti-Mtb AM antibodies or Mtb AM-binding fragments thereof comprise a heavy chain variable region and a light chain variable region, wherein each of the heavy chain and the light chain variable regions comprises a CDR1, CDR2, and CDR3; and wherein CDR1H comprises SEQ ID NO:17, CDR2H comprises SEQ ID NO:18, CDR3H comprises SEQ ID NO:19, CDR1L comprises SEQ ID NO:20, CDR2L comprises SEQ ID NO:21, and CDR3L comprises SEQ ID NO:22; and (b) a second portion comprising a second plurality of anti-Mtb AM antibodies or Mtb AM-binding fragments thereof, wherein the second plurality of anti-Mtb AM antibodies or Mtb AM-binding fragments thereof each comprise a heavy chain variable region and a light chain variable region, wherein each of the heavy chain and the light chain variable regions comprises a CDR1, CDR2, and CDR3, and wherein:

(i) CDR1H comprises SEQ ID NO:1, CDR2H comprises SEQ ID NO:2, CDR3H comprises SEQ ID NO:3, CDR1L comprises SEQ ID NO:4, CDR2L comprises SEQ ID NO:5, and CDR3L comprises SEQ ID NO:6; or (ii) CDR1H comprises SEQ ID NO:26, CDR2H comprises SEQ ID NO:27, CDR3H comprises SEQ ID NO:28, CDR1L comprises SEQ ID NO:29, CDR2L comprises SEQ ID NO:30, and CDR3L comprises SEQ ID NO:31.

7. The assay device of claim 4, wherein the reporting entity comprises a gold nanoparticle.

8. The assay device of claim 4, wherein the reporting entity comprises an enzyme.

9. The assay device of any of claim 8, wherein the enzyme is horseradish peroxidase (HRP) or alkaline phosphatase (AP).

10. The assay device of claim 4, wherein the second plurality of anti-Mtb AM antibodies or Mtb AM-binding fragments thereof or anti-mycobacterial AM antibodies is affixed to a solid support of the assay device.

11. The assay device of claim 4, wherein the first plurality of anti-Mtb AM antibodies or Mtb AM-binding fragments thereof is not affixed to a solid support of the assay device.

12. The assay device of claim 10, wherein the solid support comprises nitrocellulose.

13. The assay device of claim 4, further comprising a fluid sample pad.

14. The assay device of claim 4, further comprising a control portion.

15. The assay device of claim 14, wherein the control portion comprises a third plurality of antibodies, immobilized on a solid support of the assay device, and which third plurality of antibodies are capable of binding the first plurality of anti-Mtb AM antibodies or Mtb AM-binding fragments thereof each attached to their own reporting molecule.

16. The assay device of claim 4, wherein the assay device is a lateral flow assay device.

17. A method of detecting one or more bacteria from the MTC group in a biological sample, the method comprising:

(a) contacting the assay device of claim 4 with the biological sample; and (b) observing if one or more bacteria from the MTC group bind to the second plurality of anti-Mtb AM antibodies or Mtb AM-binding fragments thereof or anti-mycobacterial AM antibodies;

wherein if one or more bacteria from the MTC group bind to the second plurality of anti-Mtb AM antibodies or Mtb AM-binding fragments thereof or anti-mycobacterial AM antibodies, then one or more bacteria from the MTC group have been detected in the biological sample; and wherein if no bacteria from the MTC group bind to the second plurality of anti-Mtb AM antibodies or Mtb AM-binding fragments thereof or anti-mycobacterial AM antibodies, then bacteria from the MTC group have not been detected in the biological sample.

18. The method of claim 17, wherein the biological sample is urine, cerebrospinal fluid, pleural fluid, peritoneal fluid, sputum, saliva, a tissue sample, or a fine-needle aspirate.

19. A method of reducing intracellular Mtb AM in a human cell, the method comprising contacting said human cell with an anti-Mtb AM antibody or Mtb AM-binding fragment thereof, wherein the anti-Mtb AM antibodies or Mtb AM-binding fragments thereof each comprise a heavy chain variable region and a light chain variable region, wherein each of the heavy chain and the light chain variable regions comprises a CDR1, CDR2, and CDR3, and wherein:

(a) CDR1H comprises SEQ ID NO:1, CDR2H comprises SEQ ID NO:2, CDR3H comprises SEQ ID NO:3, CDR1L comprises SEQ ID NO:4, CDR2L comprises SEQ ID NO:5, and CDR3L comprises SEQ ID NO:6; or (b) CDR1H comprises SEQ ID NO:26, CDR2H comprises SEQ ID NO:27, CDR3H comprises SEQ ID NO:28, CDR1L comprises SEQ ID NO:29, CDR2L comprises SEQ ID NO:30, and CDR3L comprises SEQ ID NO:31.

* * * * *

SEQUENCE LISTING

<160> NUMBER OF SEQ ID NOS: 35

<210> SEQ ID NO 1
<211> LENGTH: 5
<212> TYPE: PRT
<213> ORGANISM: Homo sapiens

<400> SEQUENCE: 1

Ser Tyr Ala Met Ser
1 5

<210> SEQ ID NO 2
<211> LENGTH: 17
<212> TYPE: PRT
<213> ORGANISM: Homo sapiens

<400> SEQUENCE: 2

Thr Leu Ser Asp Ser Gly Gly Ala Thr His Tyr Ala Asp Ser Val Gln
1 5 10 15

Gly

<210> SEQ ID NO 3
<211> LENGTH: 13
<212> TYPE: PRT
<213> ORGANISM: Homo sapiens

<400> SEQUENCE: 3

Asp Val Pro Pro Lys Thr Ala Gly Pro Met Phe Asp Tyr
1 5 10

<210> SEQ ID NO 4
<211> LENGTH: 16
<212> TYPE: PRT
<213> ORGANISM: Homo sapiens

<400> SEQUENCE: 4

Arg Ser Ser Glu Ser Leu Val His Ser Asn Gly Asn Thr Tyr Leu Ser
1 5 10 15

<210> SEQ ID NO 5
<211> LENGTH: 8
<212> TYPE: PRT
<213> ORGANISM: Homo sapiens

<400> SEQUENCE: 5

Glu Ile Ser Lys Arg Tyr Ser Gly
1 5

<210> SEQ ID NO 6
<211> LENGTH: 9
<212> TYPE: PRT
<213> ORGANISM: Homo sapiens

<400> SEQUENCE: 6

Ala Gln Val Ser His Phe Pro Arg Thr
1 5

<210> SEQ ID NO 7
<211> LENGTH: 122
<212> TYPE: PRT
<213> ORGANISM: Homo sapiens

<400> SEQUENCE: 7

Glu Val Gln Leu Leu Glu Ser Gly Gly Gly Leu Val Gln Pro Gly Gly

-continued

```
1               5                   10                  15

Ser Gln Arg Leu Phe Cys Glu Ala Ser Gly Phe Thr Phe Ala Ser Tyr
            20                  25                  30

Ala Met Ser Trp Val Arg Leu Ala Pro Gly Lys Gly Leu Glu Trp Val
        35                  40                  45

Ser Thr Leu Ser Asp Ser Gly Gly Ala Thr His Tyr Ala Asp Ser Val
    50                  55                  60

Gln Gly Arg Phe Thr Ile Ser Arg Asp Asn Ser Asn Asn Val Val Tyr
65                  70                  75                  80

Leu Gln Met Asn Ser Leu Arg Ala Glu Asp Thr Ala Val Tyr Tyr Cys
                85                  90                  95

Ala Arg Asp Val Pro Pro Lys Thr Ala Gly Pro Met Phe Asp Tyr Trp
            100                 105                 110

Gly Leu Gly Thr Leu Val Thr Val Ser Ser
        115                 120
```

<210> SEQ ID NO 8
<211> LENGTH: 112
<212> TYPE: PRT
<213> ORGANISM: Homo sapiens

<400> SEQUENCE: 8

```
Asp Ile Val Met Thr Gln Thr Pro Leu Ser Ser Pro Val Ser Leu Gly
1               5                   10                  15

Gln Pro Ala Ser Ile Ser Cys Arg Ser Ser Glu Ser Leu Val His Ser
            20                  25                  30

Asn Gly Asn Thr Tyr Leu Ser Trp Leu His Gln Arg Pro Gly Gln Pro
        35                  40                  45

Pro Arg Leu Leu Ile Tyr Glu Ile Ser Lys Arg Tyr Ser Gly Val Ser
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Ile Tyr Phe Cys Ala Gln Val
                85                  90                  95

Ser His Phe Pro Arg Thr Phe Gly Gln Gly Thr Lys Val Glu Ile Lys
            100                 105                 110
```

<210> SEQ ID NO 9
<211> LENGTH: 366
<212> TYPE: DNA
<213> ORGANISM: Homo sapiens

<400> SEQUENCE: 9

```
gaggtgcagc tgttggagtc tgggggaggc ttggtacagc ctggggggtc ccagagactc      60

ttctgtgaag cctctggatt cacctttgcc agctatgcca tgagttgggt ccgcctggcc     120

ccagggaagg ggctggagtg ggtctcaact cttagtgata gtggtggtgc cacacactac     180

gcggactccg tgcagggccg gttcaccatc tccagagaca attccaacaa tgtggtgtat     240

ttgcaaatga acagcctgag agccgaggac acggccgttt attattgtgc gagagatgtc     300

ccccccaaga cggcaggccc catgtttgac tactggggcc tgggaaccct ggtcaccgtc     360

tcctca                                                                366
```

<210> SEQ ID NO 10
<211> LENGTH: 336
<212> TYPE: DNA
<213> ORGANISM: Homo sapiens

<400> SEQUENCE: 10
gatattgtga tgacccagac tccactctct tcccctgtca gccttggaca gccggcctcc 60
atctcctgca ggtcgagtga aagcctcgta cacagtaatg gaaacaccta cttgagttgg 120
cttcaccaga ggccaggcca gcctccaagg ctcctaattt atgaaatctc taagcggtac 180
tctggggtct cagacagatt cagtggcagt ggggcaggga cagatttcac actaaaaatc 240
agcagggtgg aagctgagga tgtcggaatt tacttctgcg cgcaagtttc acacttcccc 300
cggacgttcg gccaagggac caaggtggaa atcaaa 336

<210> SEQ ID NO 11
<211> LENGTH: 8
<212> TYPE: PRT
<213> ORGANISM: Homo sapiens

<400> SEQUENCE: 11

Gly Phe Thr Phe Ala Ser Tyr Ala
1 5

<210> SEQ ID NO 12
<211> LENGTH: 8
<212> TYPE: PRT
<213> ORGANISM: Homo sapiens

<400> SEQUENCE: 12

Leu Ser Asp Ser Gly Gly Ala Thr
1 5

<210> SEQ ID NO 13
<211> LENGTH: 16
<212> TYPE: PRT
<213> ORGANISM: Homo sapiens

<400> SEQUENCE: 13

Ala Arg Asp Val Pro Pro Lys Thr Ala Gly Pro Met Phe Asp Tyr Trp
1 5 10 15

<210> SEQ ID NO 14
<211> LENGTH: 11
<212> TYPE: PRT
<213> ORGANISM: Homo sapiens

<400> SEQUENCE: 14

Glu Ser Leu Val His Ser Asn Gly Asn Thr Tyr
1 5 10

<210> SEQ ID NO 15
<211> LENGTH: 10
<212> TYPE: PRT
<213> ORGANISM: Homo sapiens
<220> FEATURE:
<221> NAME/KEY: MISC_FEATURE
<222> LOCATION: (3)..(9)
<223> OTHER INFORMATION: Xaa is any amino acid

<400> SEQUENCE: 15

Glu Ile Xaa Xaa Xaa Xaa Xaa Xaa Xaa Ser
1 5 10

<210> SEQ ID NO 16

<400> SEQUENCE: 16

000

<210> SEQ ID NO 17
<211> LENGTH: 5
<212> TYPE: PRT
<213> ORGANISM: Homo sapiens

<400> SEQUENCE: 17

Thr Tyr Trp Ile His
1 5

<210> SEQ ID NO 18
<211> LENGTH: 17
<212> TYPE: PRT
<213> ORGANISM: Homo sapiens

<400> SEQUENCE: 18

Trp Ile Ile Pro Lys Ser Gly Gly Thr Asn Tyr Ala Gln Lys Phe Gln
1 5 10 15

Gly

<210> SEQ ID NO 19
<211> LENGTH: 12
<212> TYPE: PRT
<213> ORGANISM: Homo sapiens

<400> SEQUENCE: 19

Gly Ile Leu Leu Asn Gly Ile Gly Ala Phe Asp Tyr
1 5 10

<210> SEQ ID NO 20
<211> LENGTH: 11
<212> TYPE: PRT
<213> ORGANISM: Homo sapiens

<400> SEQUENCE: 20

Arg Thr Ser Gln Thr Val Ser Ser Asn Leu Asn
1 5 10

<210> SEQ ID NO 21
<211> LENGTH: 7
<212> TYPE: PRT
<213> ORGANISM: Homo sapiens

<400> SEQUENCE: 21

Gly Ile Ser Asp Leu His Ser
1 5

<210> SEQ ID NO 22
<211> LENGTH: 9
<212> TYPE: PRT
<213> ORGANISM: Homo sapiens

<400> SEQUENCE: 22

Gln Gln Ser Tyr Ser Leu Pro Arg Thr
1 5

<210> SEQ ID NO 23
<211> LENGTH: 121
<212> TYPE: PRT
<213> ORGANISM: Homo sapiens

<400> SEQUENCE: 23

Gln Val Gln Leu Val Glu Ser Gly Ala Glu Val Lys Lys Pro Gly Ala

```
1               5                   10                  15

Ser Val Lys Val Ser Cys Lys Ala Ser Gly Tyr Thr Phe Ser Thr Tyr
            20                  25                  30

Trp Ile His Trp Met Arg Gln Ala Pro Gly Gln Gly Pro Glu Trp Met
        35                  40                  45

Gly Trp Ile Ile Pro Lys Ser Gly Gly Thr Asn Tyr Ala Gln Lys Phe
    50                  55                  60

Gln Gly Arg Val Ala Met Thr Arg Asp Thr Ser Leu Asn Thr Val Tyr
65                  70                  75                  80

Met Glu Leu Ser Arg Leu Thr Ser Asp Asp Thr Ala Val Tyr Tyr Cys
                85                  90                  95

Ala Arg Gly Ile Leu Leu Asn Gly Ile Gly Ala Phe Asp Tyr Trp Gly
            100                 105                 110

Gln Gly Thr Leu Val Thr Val Ser Ser
        115                 120


<210> SEQ ID NO 24
<211> LENGTH: 121
<212> TYPE: PRT
<213> ORGANISM: Homo sapiens

<400> SEQUENCE: 24

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Ala Thr Tyr
            20                  25                  30

Trp Ile His Trp Met Arg Gln Ala Pro Gly Gln Gly Pro Glu Trp Met
        35                  40                  45

Gly Trp Ile Ile Pro Lys Ser Gly Gly Thr Asn Tyr Ala Gln Lys Phe
    50                  55                  60

Gln Gly Arg Val Ala Met Thr Arg Asp Thr Ser Leu Asn Thr Val Tyr
65                  70                  75                  80

Met Glu Leu Ser Arg Leu Thr Ser Asp Asp Thr Ala Val Tyr Tyr Cys
                85                  90                  95

Ala Arg Gly Ile Leu Leu Asn Gly Ile Gly Ala Phe Asp Tyr Trp Gly
            100                 105                 110

Gln Gly Thr Leu Val Thr Val Ser Ser
        115                 120


<210> SEQ ID NO 25
<211> LENGTH: 107
<212> TYPE: PRT
<213> ORGANISM: Homo sapiens

<400> SEQUENCE: 25

Asp Ile Val Met Thr Gln Ser Pro Ser Ser Leu Ser Ala Ser Val Gly
1               5                   10                  15

Asp Arg Val Thr Ile Thr Cys Arg Thr Ser Gln Thr Val Ser Ser Asn
            20                  25                  30

Leu Asn Trp Tyr Gln Gln Arg Pro Gly Lys Ala Pro Lys Leu Leu Ile
        35                  40                  45

Ser Gly Ile Ser Asp Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser Tyr Ser Leu Pro Arg
```

```
                85                  90                  95

Thr Phe Gly Gln Gly Thr Lys Val Glu Ile Lys
            100                 105


<210> SEQ ID NO 26
<211> LENGTH: 5
<212> TYPE: PRT
<213> ORGANISM: Homo sapiens

<400> SEQUENCE: 26

Ser Tyr Tyr Leu Ser
1               5


<210> SEQ ID NO 27
<211> LENGTH: 16
<212> TYPE: PRT
<213> ORGANISM: Homo sapiens

<400> SEQUENCE: 27

Tyr Met Phe His Arg Gly Ser Thr Asn Arg Asn Pro Ser Leu Arg Ser
1               5                   10                  15


<210> SEQ ID NO 28
<211> LENGTH: 14
<212> TYPE: PRT
<213> ORGANISM: Homo sapiens

<400> SEQUENCE: 28

His Leu Gly Ile Val Gly Val Thr Asn Ala Ala Phe Asp Ile
1               5                   10


<210> SEQ ID NO 29
<211> LENGTH: 13
<212> TYPE: PRT
<213> ORGANISM: Homo sapiens

<400> SEQUENCE: 29

Ser Gly Ser Ser Ser Asn Ile Gly Asn Asn Tyr Val Ser
1               5                   10


<210> SEQ ID NO 30
<211> LENGTH: 7
<212> TYPE: PRT
<213> ORGANISM: Homo sapiens

<400> SEQUENCE: 30

Gln Asn Asp Lys Arg Pro Ser
1               5


<210> SEQ ID NO 31
<211> LENGTH: 11
<212> TYPE: PRT
<213> ORGANISM: Homo sapiens

<400> SEQUENCE: 31

Gly Thr Trp Asp Arg Ser Leu Asn Ala Asp Val
1               5                   10


<210> SEQ ID NO 32
<211> LENGTH: 122
<212> TYPE: PRT
<213> ORGANISM: Homo sapiens

<400> SEQUENCE: 32
```

```
Gln Val Gln Leu Gln Glu Ser Gly Pro Gly Leu Val Glu Pro Ser Glu
1               5                   10                  15

Thr Leu Ser Leu Thr Cys Thr Val Ser Gly Gly Ser Ile Arg Ser Tyr
            20                  25                  30

Tyr Leu Ser Trp Ile Arg Gln Ser Pro Lys Lys Gly Leu Glu Trp Ile
        35                  40                  45

Gly Tyr Met Phe His Arg Gly Ser Thr Asn Arg Asn Pro Ser Leu Arg
    50                  55                  60

Ser Arg Val Thr Met Ser Leu Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Thr His Leu Gly Ile Val Gly Val Thr Asn Ala Ala Phe Asp Ile Trp
            100                 105                 110

Gly Gln Gly Thr Met Val Thr Val Ser Ser
        115                 120


<210> SEQ ID NO 33
<211> LENGTH: 367
<212> TYPE: DNA
<213> ORGANISM: Homo sapiens

<400> SEQUENCE: 33

caggtgcagc tgcaggagtc gggcccagga ctggtggagc cttcggagac cctgtccctc      60

acgtgcactg tctctggtgg ctccatcaga agttactact tgagctggat ccggcagtcc     120

ccgaagaagg gactggagtg gattggatat atgtttcacc gtgggagcac caaccgcaac     180

ccctccctca ggagtcgggt caccatgtca ctggacacgt ccaagaacca gttctccctg     240

aaactgacct ctgtgaccgc cgcagacacg gccgtctatt attgtgcgac acatctcgga     300

atagtggggg ttactaacgc tgcttttgat atctggggcc aagggacaat ggtcaccgtc     360

tcttcag                                                               367


<210> SEQ ID NO 34
<211> LENGTH: 110
<212> TYPE: PRT
<213> ORGANISM: Homo sapiens

<400> SEQUENCE: 34

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Leu Leu Pro Gly Thr Ala Pro Lys Leu Leu
        35                  40                  45

Ile Tyr Gln Asn Asp Lys Arg Pro Ser Asp Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Arg Ser Leu
                85                  90                  95

Asn Ala Asp Val Phe Gly Gly Gly Thr Lys Leu Thr Val Leu
            100                 105                 110


<210> SEQ ID NO 35
<211> LENGTH: 331
<212> TYPE: DNA
```

-continued

```
<213> ORGANISM: Homo sapiens

<400> SEQUENCE: 35

cagtctgtgc tgacgcagcc gccctcagtg tctgcggccc caggacagaa ggtcaccatc     60

tcctgctctg gaagcagctc caacattgga aataattatg tatcctggta tcagttactc    120

ccaggaacag cccccaaact cctcatctat caaaatgata agcgaccctc agacattcct    180

gaccgattct ctggctccaa gtctggcacg tcagccaccc tgggcatcac cggactccag    240

actggggacg aggccgatta ttactgcgga acatgggata gaagcctgaa tgctgacgtt    300

ttcggcgggg ggaccaagct gaccgtccta g                                   331
```